(12) United States Patent
Annapragada et al.

(10) Patent No.: US 11,141,495 B2
(45) Date of Patent: *Oct. 12, 2021

(54) MRI IMAGING OF AMYLOID PLAQUE USING LIPOSOMES

(71) Applicant: Texas Children's Hospital, Houston, TX (US)

(72) Inventors: Ananth V. Annapragada, Manvel, TX (US); Eric A. Tanifum, Katy, TX (US); Mayank Srivastava, Pearland, TX (US)

(73) Assignee: Texas Children's Hospital, Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 16/791,068

(22) Filed: Feb. 14, 2020

(65) Prior Publication Data

US 2020/0179540 A1 Jun. 11, 2020

Related U.S. Application Data

(63) Continuation of application No. 16/677,751, filed on Nov. 8, 2019, which is a continuation of application
(Continued)

(51) Int. Cl.
*A61K 9/00* (2006.01)
*A61K 49/18* (2006.01)
(Continued)

(52) U.S. Cl.
CPC ...... *A61K 49/1812* (2013.01); *A61K 49/0034* (2013.01); *A61K 49/0084* (2013.01); *A61K 49/10* (2013.01); *A61K 49/126* (2013.01)

(58) Field of Classification Search
CPC .................................................. A61K 49/1812
See application file for complete search history.

(56) References Cited

U.S. PATENT DOCUMENTS 5,204,085 A 4/1993 Vanderipe
5,676,928 A 10/1997 Klaveness et al.
(Continued)

FOREIGN PATENT DOCUMENTS

EP 1982733 10/2008
EP 2694116 2/2014
(Continued)

OTHER PUBLICATIONS

Winter, et al., "Improved Molecular Imaging Contrast Agent for Detection of Human Thrombus" Mag. Res. Med. 2003, 50, 411-416.
(Continued)

*Primary Examiner* — Paul W Dickinson
(74) *Attorney, Agent, or Firm* — Kern Kendrick, LLC; Benjamen E. Kern

(57) ABSTRACT

Provided are aromatic compounds, phospholipid-polymer-aromatic conjugates comprising the aromatic compounds, and liposome compositions including the phospholipid-polymer-aromatic conjugates. The liposomal compositions may be useful for imaging of Alzheimer's Disease, for example, imaging of the amyloid-β plaque deposits characteristic of Alzheimer's Disease.

20 Claims, 26 Drawing Sheets
(10 of 26 Drawing Sheet(s) Filed in Color)

CLogP values 3.12

3.52

Florbetapir 6.11

MeXO4

1.56

Compound i 1.80

Compound ii 1.06

Compound iii

Related U.S. Application Data

No. 15/366,667, filed on Dec. 1, 2016, now Pat. No. 10,537,649, which is a continuation of application No. 14/878,745, filed on Oct. 8, 2015, now Pat. No. 9,744,251.

(60) Provisional application No. 62/111,057, filed on Feb. 2, 2015, provisional application No. 62/061,514, filed on Oct. 8, 2014.

(51) Int. Cl.
*A61K 49/00* (2006.01)
*A61K 49/10* (2006.01)
*A61K 49/12* (2006.01)

(56) References Cited

U.S. PATENT DOCUMENTS

| | | |
|---|---|---|
| 6,171,614 B1 | 1/2001 | Chaikof et al. |
| 6,821,504 B2 | 11/2004 | Wisniewski et al. |
| 7,138,136 B2 | 11/2006 | Annapragada et al. |
| 7,208,174 B2 | 4/2007 | Huwyler et al. |
| 7,713,517 B2 | 5/2010 | Annapragada et al. |
| 7,785,568 B2 | 8/2010 | Annapragada et al. |
| 8,357,351 B2 | 1/2013 | Karathanasis et al. |
| 8,642,013 B2 | 2/2014 | Annapragada et al. |
| 8,679,531 B2 | 3/2014 | Annapragada et al. |
| 8,911,708 B2 | 12/2014 | Annapragada et al. |
| 2003/0190284 A1 | 10/2003 | Annapragada et al. |
| 2006/0099141 A1 | 5/2006 | O'Brien et al. |
| 2007/0031326 A1 | 2/2007 | Shirvan et al. |
| 2007/0160658 A1 | 7/2007 | Connor et al. |
| 2007/0292354 A1 | 12/2007 | Port |
| 2008/0131369 A1 | 6/2008 | Annapragada et al. |
| 2009/0123047 A1 | 5/2009 | Yfantis |
| 2009/0311191 A1 | 12/2009 | Annapragada et al. |
| 2010/0105631 A1 | 4/2010 | Curz et al. |
| 2010/0190831 A1 | 7/2010 | Shi et al. |
| 2010/0286067 A1 | 10/2010 | Defrees |
| 2011/0093960 A1 | 4/2011 | Edwards et al. |
| 2011/0311457 A1 | 12/2011 | Skerrett et al. |
| 2012/0003159 A1 | 1/2012 | Annapragada et al. |
| 2012/0258044 A1 | 10/2012 | Annapragada et al. |
| 2013/0289140 A1 | 10/2013 | Mbebi-Liegeois et al. |
| 2014/0161875 A1 | 6/2014 | Winderickx et al. |

FOREIGN PATENT DOCUMENTS

| | | |
|---|---|---|
| EP | 2756459 A1 | 7/2014 |
| WO | 2002028441 | 4/2002 |
| WO | 2005107820 | 11/2005 |
| WO | 2008134618 A2 | 11/2008 |
| WO | 2009073236 | 6/2009 |
| WO | 2009073896 | 6/2009 |
| WO | 2009150686 | 12/2009 |
| WO | 2010017094 | 2/2010 |
| WO | 2010107990 | 9/2010 |
| WO | 2011045415 | 4/2011 |
| WO | 2011159297 | 12/2011 |
| WO | 2012119117 | 9/2012 |
| WO | 2012139080 | 10/2012 |
| WO | 2013110013 | 8/2013 |
| WO | 2014152229 | 9/2014 |
| WO | 2016057812 | 4/2016 |

OTHER PUBLICATIONS

Thompson, et al., "Cortical Variability and Asymmetry in Normal Aging and Alzheimer's Disease" Cerebral Cortex 1998, 8, 492-509.

Mcneely, et al. "Decreased Circulation Time Offsets Increased Efficacy of PEGylated Nanocarriers Targeting Folate Receptors of Glioma" Nanotechnology 2007, 18, 1-11.

Burke, et al., "Imaging of Pulmonary Embolism and t-PA Therapy Effects Using MDCT and Liposomal Iohexol Blood Pool Agent: Preliminary Results in a Rabbit Model" Academic Radiol. 2007, 14, 355-362.

Kao, et al., "Long-Residence-Time Nano-Scale Liposomal Iohexol for X-ray-Based Blood Pool Imaging" Acad. Radiol. 2003, 10, 475-483.

Ding, et al., "Folate Receptor-Targeted Fluorescent Paramagnetic Bimodal Liposomes for Tumor Imaging" Int. J. Nanomed. 2011, 6, 2513-2520.

European Search Report issued in EP2756459, dated Jul. 29, 2014.

Skaat, et al., "Synthesis of Fluorescent-Maghemite Nanoparticles as Multimodal Imaging Agents for Amyloid-Beta Fibrils Detection and Removal by a Magnetic Field" Biochem. Biophys. Res. Commun. 2009, 386, 645-649.

Van Groen, el al., "Reduction of Alzheimer's Disease Amyloid Plaque Load in Transgenic Mice by D3, a D-Enantiomeric Peptide Identified by Mirror IMage Phage Display" Chem. Med. Chem. 2008, 3, 1848-1852.

Written Opinion and International Search Report from PCT Application No. PCT/US12/032649 dated Jun. 20, 2012.

Mukundan, et al., "A Liposomal Nanoscale Contrast Agent for Preclinical CT in Mice" AJR Am. J. Roentgenol. 2006, 186, 300-307.

Karathanasis, et al., "Multifunctional Nanocarriers for Mammographic Quantification of Tumor Dosing and Prognosis of Breast Cancer Therapy" Biomaterials 2008, 29, 4815-4822.

Karathanasis, et al., "Imaging Nanoprobe for Prediction of Outcome of Nanoparticle Chemotherapy by Using Mammography" Radiology 2009, 250, 398-406.

Karathanasis, et al., "Tumor Vascular Permeability to a Nanoprobe Correlates to Tumor-Specific Expression Levels of Angiogenic Markers" PLoS One 2009, 4, 5843.

Samei, et al., "Micro-CT Imaging of Breast Tumors in Rodents Using a Liposomal, Nanoparticle Contrast Agent" Int. J. Nanomedicine 2009, 4, 277-282.

Klunk, et al., Imaging AB Plaques in Living Transgenic Mice with Multiphoton Microscopy and Methoxy-XO4, a Systemically Administered Congo Red Derivative J. Neuropath. Exp. Neurol. 2002, 61, 797-805.

European Search Report in European Application No. EP12767275, dated Apr. 29, 2015.

Napadow, et al., "Quantitative Analysis of Three-Dimensional-Resolved Fiber Architecture in Heterogeneous Skeletal Muscle Tissue Using NMR and Optical Imaging Methods" Biophys. J. 2001, 80, 2968-2975.

Fosshein, et al., "Paramagnetic Liposomes as MRI Contrast Agents: Influence of Liposomal Physicochemical Properties on the in Vitro Relaxivity" Mag. Res. Imag. 1999, 17, 83-89.

Montez, et al., "Altered temporal correlations in parietal alpha and prefrontal theta oscillations in early-stage Alzheimer Disease" Proceed. Nat. Acad. Sci. 2009, 1-6.

Written Opinion and International Search Report from PCT Application No. PCT/US15/54732 dated Jan. 11, 2016.

Wald et al., "Spatial Autocorrelation and Mean Intercept Length Analysis of Trabecular Bone Anisotropy Applied to in vivo Magnetic Resonance Imaging" Med. Phys. 2007, 34, 1110-1120.

Written Opinion and International Search Report from PCT Application No. PCT/US13/22336 dated Apr. 1, 2013.

Sellers, "Why Derivatize?", downloaded from http://www.restek.com/pdfs/adv_2007_03_07.

Supplementary European Search Report issued in EP15849750, dated May 23, 2018.

Tanifum, et al., "Intravenous Delivery of Targeted Liposomes to Amyloid-[beta] Pathology in APP/PSEN1 Transgenic Mice", PLOS ONE, vol. 7, No. 10, Oct. 31, 2012 p. e48515.

Tanifum, et al., "A Novel Liposomal Nanoparticle for the Imaging of Amyloid Plaque by Magnetic Resonance Imaging", Journal of Alzeimers Dosease, vol. 52, No. 2, May 10, 2016, pp. 731-745.

Communication pursuant to Article 94(3) EPC issued in European Application No. 15849750.3, dated Sep. 5, 2018.

Office Action issued in Japanese Patent Application No. 2017-538918, dated Nov. 20, 2018.

(56) References Cited

OTHER PUBLICATIONS

Extended European Search Report and Written Opinion issued in European patent application No. 19172751.0, dated Jul. 26, 2019.
Non-Final Office Action issued in U.S. Appl. No. 16/677,751, dated Feb. 20, 2020.
Office Action issued in Mexican patent application No. MX/a/2017/004695, dated Aug. 26, 2019.
Non-Final Office Action issued in U.S. Appl. No. 15/366,667, dated Feb. 21, 2019.
Final Office Action issued in U.S. Appl. No. 15/366,667, dated Jun. 14, 2019.

CLogP values
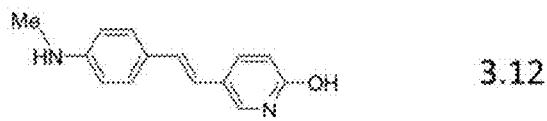
3.12
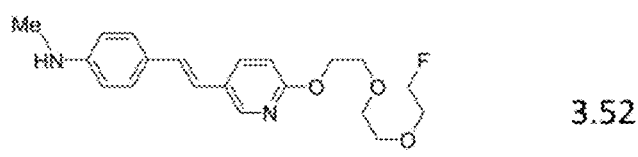
3.52
Florbetapir
6.11
MeXO4
1.56
Compound i
1.80
Compound ii
1.06
Compound iii
FIG. 1A

| | CLogP values |
|---|---|
| SB-13 | 3.67 |
| Compound iv | 3.46 |
| Compound x | 2.99 |
| Compound xi | 2.95 |
| Compound xii | 2.63 |
| Compound xiii | 2.01 |

FIG. 1C

| Bilayer Formulation | Mean Diameter, nm | Polydispersity index |
|---|---|---|
| DPPC, Cholesterol, DSPE-PEG, BSA-DTPA-Gd, DSPE-PEG-MeXO4 | 231.6 | 0.08 |
| DPPC, Cholesterol, BSA-DTPA-Gd, DSPE-PEG-MeXO4 | 246.1 | 0.21 |
| DPPC, Cholesterol, DSPE-PEG, BSA-DTPA-Gd | 100.8 | 0.05 |
| DPPC, Cholesterol, DSPE-PEG, BSA-DTPA-Gd, DSPE-PEG-Compound iii | 122.5 | 0.07 |
| DPPC, Cholesterol, DSPE-PEG, BSA-DTPA-Gd, DSPE-PEG-MeXO4 | 223.5±12.6 | 0.08 |
| DPPC, Cholesterol, DSPE-PEG, BSA-DTPA-Gd | 131.9±5.8 | 0.13±0.05 |
| DPPC, Cholesterol, DSPE-PEG, BSA-DTPA-Gd, DSPE-PEG-Compound iii | 148.9±19.5 | 0.05±0.05 |

FIG. 8

| Mouse Model | APP+ Genotype | Treatment | Pathology | ICG | Ligand | MRI |
|---|---|---|---|---|---|---|
| TetO/APP$_{swe}$ | Positive | Targeted | 3 | X | X | X |
| TetO/APP$_{swe}$ | Negative | Targeted | 0 | - | - | - |
| TetO/APP$_{swe}$ | Positive | Targeted | 3 | X | X | X |
| TetO/APP$_{swe}$ | Positive | Targeted | 3 | X | X | X |
| TetO/APP$_{swe}$ | Positive | Targeted | 3 | X | X | X |
| TetO/APP$_{swe}$ | Positive | Targeted | 3 | X | X | X |
| TetO/APP$_{swe}$ | Positive | Targeted | 3 | X | X | X |
| TetO/APP$_{swe}$ | Negative | Targeted | 0 | - | - | - |
| Tg2576 | Positive | Targeted | 1 | X | X | X |
| Tg2576 | Positive | Targeted | 1 | X | X | X |
| Tg2576 | Positive | Targeted | 0 | - | - | - |
| Tg2576 | Positive | Targeted | 0 | - | - | - |
| TG2576 | Positive | Untargeted | 0 | - | - | - |
| Tg2576 | Positive | Untargeted | 0 | - | - | - |
| Tg2576 | Positive | Targeted | 0 | - | - | - |
| Tg2576 | Negative | Targeted | 0 | - | - | - |
| Tg2576 | Negative | Untargeted | 0 | - | - | - |
| Tg2576 | Negative | Targeted | 0 | - | - | - |
| Tg2576 | Negative | Targeted | 0 | - | - | - |
| Tg2576 | Negative | Targeted | 0 | - | - | - |

FIG. 12

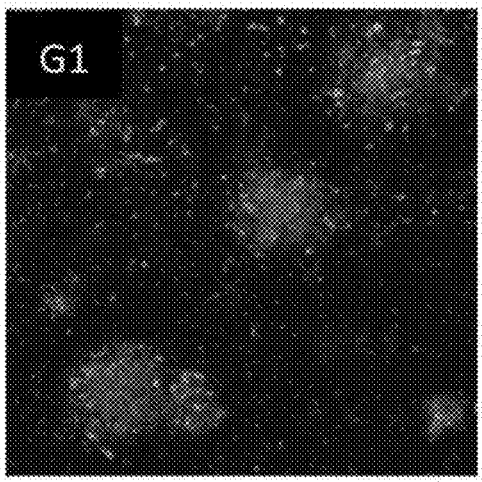
FIG. 14G1
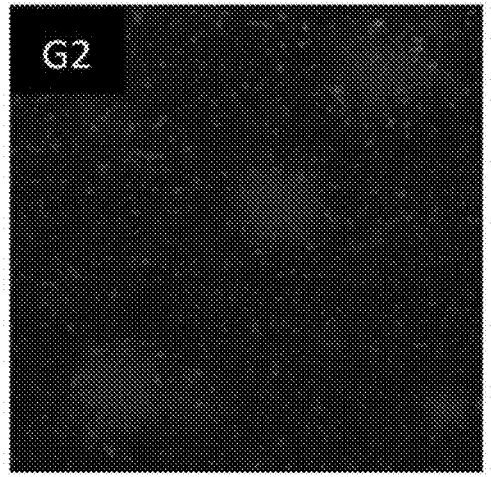
FIG. 14G2
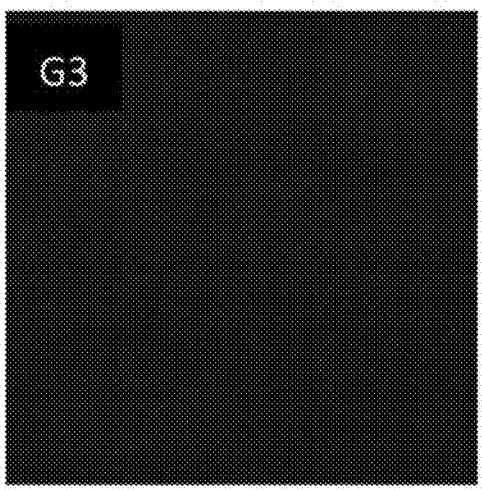
FIG. 14G3
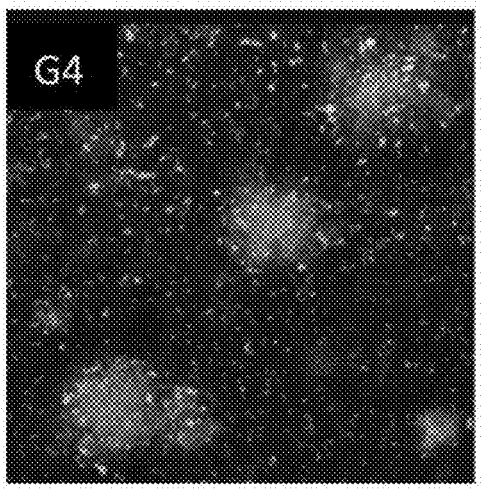
FIG. 14G4

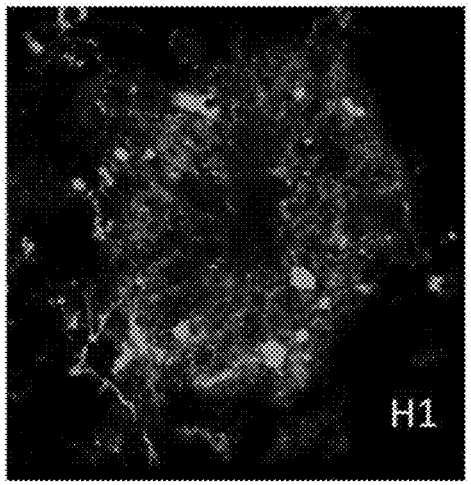
FIG. 14H1
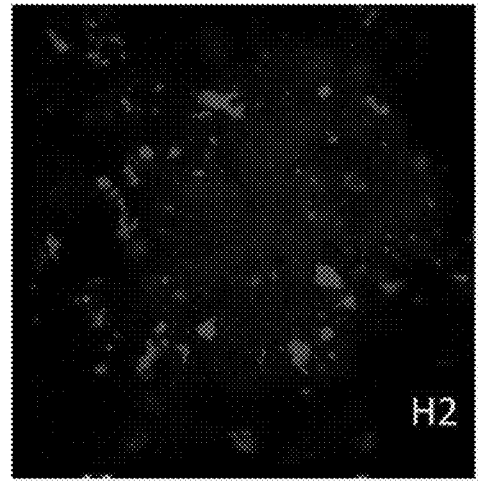
FIG. 14H2
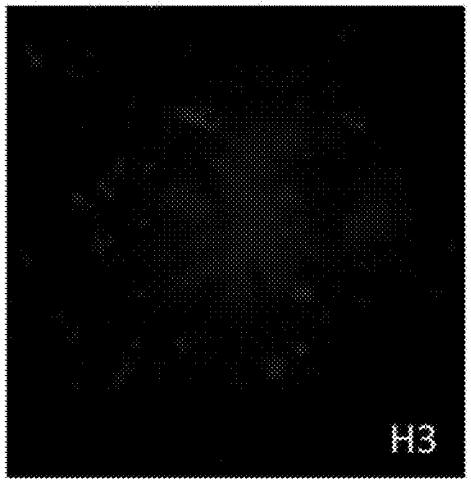
FIG. 14H3
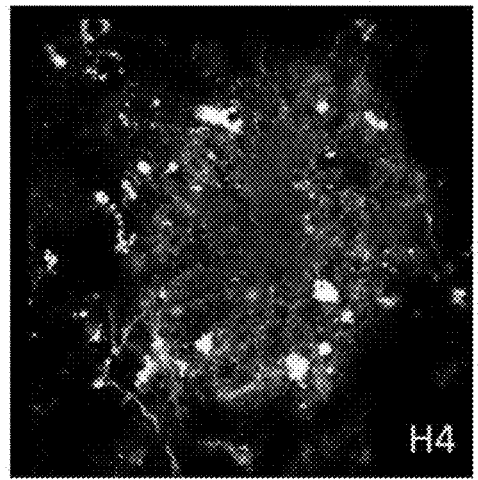
FIG. 14H4

MRI IMAGING OF AMYLOID PLAQUE USING LIPOSOMES

CROSS-REFERENCE TO RELATED APPLICATIONS

This application is a continuation of U.S. patent application Ser. No. 16/677,751, filed on Nov. 8, 2019, which is a continuation of U.S. patent application Ser. No. 15/366,667, filed on Dec. 1, 2016 and issued as U.S. Pat. No. 10,537,649, which is a continuation of U.S. patent application Ser. No. 14/878,745, filed on Oct. 8, 2015 and issued as U.S. Pat. No. 9,744,251, which claims priority from U.S. Provisional Patent Application Nos. 62/061,514, filed on Oct. 8, 2014, and 62/111,057, filed Feb. 2, 2015, both of which are entirely incorporated by reference herein.

BACKGROUND

Alzheimer's disease ("AD") is a neurodegenerative illness characterized by memory loss and other cognitive deficits. AD is the most common form of dementia and affects one in every eight people over the age of 65 and one in every two over the age of 85. AD is the sixth leading cause of death in the United States. Over 5.5 million Americans suffer from AD, with an estimated annual cost of $200 billion USD. By 2050, it is projected that AD will affect over 20 million Americans at an annual price tag of $1.1 Trillion USD (in 2011 dollars). Around the world, the estimated figures for the year 2011 were over 37 million sufferers, at an associated cost of over $600 billion (USD).

Effective diagnostic tests for AD are needed in the field. At present, AD is typically only conclusively diagnosed by post-mortem histopathological analysis. Diagnosis in living subjects relies primarily on psychiatric testing to detect cognitive impairment. However, the major neuropathological hallmarks of AD—extracellular amyloid-β ("Aβ") plaque deposits and intracellular neurofibrillary tangles—manifest long before clinical symptoms are discernable. Aβ deposits also represent a major risk factor for hemorrhagic stroke.

Two positron emission tomography (PET) imaging agents that bind specifically to amyloid plaques have recently been approved by the FDA, and can be used for the detection of amyloid plaques. However, their spatial resolution is limited by that of the PET modality, and is on the order of 5-10 mm, limiting any anatomy-specific information available in the image. PET imaging also requires the use of radio-isotopes, and carries the risk of significant radiation: an amyloid scan is estimated to expose the patient to about 7 mSv of radiation dose, roughly equivalent to several CT scans, as a typical head CT may be about 2 mSv. Availability of radioactive PET agents also remains a challenge, due to their short half-life. Simultaneous detection of a cognate factor such as tau tangles could improve the specificity of a diagnostic test, and a number of PET imaging agents for tau detection are currently in development. A non-radioactive amyloid imaging agent would be of significant interest, addressing both the distribution challenges and the radiation dose concerns with current PET imaging agents, and in combination with a tan imaging agent, possibly constituting a diagnostic for AD.

Some previous efforts on developing non-radioactive amyloid-targeting MRI agent have primarily focused on either proton T2 (using the T2 relaxivities of iron oxide nanoparticles), or $^{19}$F imaging (using high signal-to-noise ratios achievable due to the absence of endogenous signal). High T2 relaxivities lead to the suppression of overall signal, making detection and differentiation from inherent hypo-intense regions challenging, and quantitation of the images unreliable. Further, the absence of endogenous MR-visible fluorine also means there is no anatomical landmark in the $^{19}$F image.

Other previous work demonstrated that liposomes targeted to amyloid plaque by the thioflavine analog Methoxy-XO4, penetrated the blood-brain barrier (BBB), and successfully bound the majority of amyloid plaques in the APP/PSEN1 mouse model of AD. Existing amyloid binding ligands, including methoxy-XO4 are, however, hydrophobic. In liposomal formulations, they interfere with the lipid bilayer. When loaded with Gd chelates for MRI T1 contrast, methoxy-XO4 targeted liposomes were unstable to the osmotic gradient created by the high Gd chelate internal concentration, and were destabilized.

The present application appreciates that detecting amyloid deposits may be a challenging endeavor.

SUMMARY

In one embodiment, a liposomal composition is provided. The liposomal composition may include a membrane. The membrane may include a phospholipid-polymer-aromatic conjugate. The aromatic moiety in the phospholipid-polymer-aromatic conjugate may be represented by Structural Formula I:

(I)

or a pharmaceutically acceptable salt thereof. In the aromatic moiety in the phospholipid-polymer-aromatic conjugate represented by Structural Formula I, X may be —$R^2$—O— or —$R^2$—N($R^3$)—. $R^1$ may be $C_2$-$C_6$ alkyl or alkenyl. $R^2$ may be a linking group including 1 to 6 carbon atoms. $R^2$ may include one of: alkylene or alkoxyalkylene. $R^3$ may be hydrogen, $C_1$-$C_6$ alkyl, or $C_1$-$C_6$ alkoxyalkyl. Ar may be a monocyclic or polycyclic group. Ar may include at least one aromatic or heteroaromatic ring. Het may be a monocyclic or polycyclic group. Het may include at least one heteroaromatic ring. The aromatic moiety in the phospholipid-polymer-aromatic conjugate represented by Formula I may further be substituted. For example, $R^2$ may be substituted with zero, one or more of: hydroxyl, $C_1$-$C_6$ alkyl, and $C_1$-$C_6$ hydroxyalkyl. Ar, Het, $R^1$, and $R^3$ other than hydrogen may be independently substituted with zero, one or more of: halogen; —OH; alkyl, —O-alkyl, aryl, —O-aryl or —(O-alkylene)$_{1-6}$ optionally substituted with —OH or halogen; —$NH_2$; —NH-alkyl; —N-dialkyl; carboxyl; sulfonyl; carbamoyl; and glycosyl.

In another embodiment, a method for imaging amyloid deposits in a subject is provided. The method may include introducing into the subject a detectable quantity of a liposomal composition. The method may include allowing sufficient time for the liposomal composition to be associated with one or more amyloid deposits. The method may include detecting the liposomal composition associated with the one or more amyloid deposits. The liposomal composition of the method may include a membrane. A nonradioactive magnetic resonance imaging (MRI) contrast enhancing agent may be at least one of encapsulated by or bound to the membrane. The membrane may include a phospholipid-polymer-aromatic conjugate. The aromatic moiety in the phospholipid-polymer-aromatic conjugate may be represented by Structural Formula I:

(I)

or a pharmaceutically acceptable salt thereof. In the aromatic moiety in the phospholipid-polymer-aromatic conjugate represented by Structural Formula I, X may be —R—O— or —R$^2$—N(R$^3$)—. R$^1$ may be C$_2$-C$_6$ alkyl or alkenyl. R$^2$ may be a linking group including 1 to 6 carbon atoms. R$^2$ may include one of: alkylene or alkoxyalkylene. R$^3$ may be hydrogen, C$_1$-C$_6$ alkyl, or C$_1$-C$_6$ alkoxyalkyl. Ar may be a monocyclic or polycyclic group. Ar may include at least one aromatic or heteroaromatic ring. Het may be a monocyclic or polycyclic group. Het may include at least one heteroaromatic ring. The aromatic moiety in the phospholipid-polymer-aromatic conjugate represented by Formula I may further be substituted. For example, R$^2$ may be substituted with zero, one or more of: hydroxyl, C$_1$-C$_6$ alkyl, and C$_1$-C$_6$ hydroxyalkyl. Ar, Het, R$^1$, and R$^3$ other than hydrogen may be independently substituted with zero, one or more of: halogen; —OH; alkyl, —O-alkyl, aryl, —O-aryl or —(O-alkylene)$_{1-6}$ optionally substituted with —OH or halogen; —NH$_2$; —NH-alkyl; —N-dialkyl; carboxyl; sulfonyl; carbamoyl; and glycosyl.

In one embodiment, a phospholipid-polymer-aromatic conjugate is provided. The aromatic moiety in the phospholipid-polymer-aromatic conjugate may be represented by Structural Formula I:

—X—Ar—R$^1$-Het    (I)

or a pharmaceutically acceptable salt thereof. In the aromatic moiety in the phospholipid-polymer-aromatic conjugate represented by Structural Formula I, X may be or —R$^2$—O— or —R$^2$—N(R$^3$)—. R$^1$ may be C$_2$-C$_6$ alkyl or alkenyl. R$^2$ may be a linking group including 1 to 6 carbon atoms. R$^2$ may include one of: alkylene or alkoxyalkylene. R$^3$ may be hydrogen, C$_1$-C$_6$ alkyl, or C$_1$-C$_6$ alkoxyalkyl. Ar may be a monocyclic or polycyclic group. Ar may include at least one aromatic or heteroaromatic ring. Het may be a monocyclic or polycyclic group. Het may include at least one heteroaromatic ring. The aromatic moiety in the phospholipid-polymer-aromatic conjugate represented by Formula I may further be substituted. For example, R$^2$ may be substituted with zero, one or more of: hydroxyl, C$_1$-C$_6$ alkyl, and C$_1$-C$_6$ hydroxyalkyl. Ar, Het, R$^1$, and R$^3$ other than hydrogen may be independently substituted with zero, one or more of: halogen; —OH; alkyl, —O-alkyl, aryl, —O-aryl or —(O-alkylene)$_{1-6}$ optionally substituted with —OH or halogen; —NH$_2$; —NH-alkyl; —N-dialkyl; carboxyl; sulfonyl; carbamoyl; and glycosyl.

In another embodiment, a compound represented by Structural Formula II is provided:

R$^5$—Ar—R$^1$-Het    (II)

or a pharmaceutically acceptable salt thereof. In the compound represented by Formula II, R$^1$ may be C$_2$-C$_6$ alkyl or alkenyl. R$^5$ may be hydrogen, hydroxyl, H—R$^2$, HO—R$^2$—, H—R$^2$—N(R$^3$)—, or HO—R$^2$—N(R$^3$)—. R$^2$ may be a linking group including 1 to 6 carbon atoms. R$^2$ may include one of: alkylene, or alkoxyalkylene. R$^3$ may be hydrogen, C$_1$-C$_6$ alkyl, or C$_1$-C$_6$ alkoxyalkyl. Ar may be a monocyclic or polycyclic group, Ar may include at least one aromatic or heteroaromatic ring. Het may be a monocyclic or polycyclic group. Het may include at least one heteroaromatic ring. The compound represented by Structural Formula II may further be substituted. For example, R$^2$ may be substituted with zero, one or more of, hydroxyl, C$_1$-C$_6$ alkyl, and C$_1$-C$_6$ hydroxy alkyl. Ar, Het, R$^1$, and R$^3$ other than hydrogen may be independently substituted with zero, one or more of: halogen; —OH; alkyl, —O-alkyl, aryl, —O-aryl or —(O-alkylene)$_{1-6}$ optionally substituted with —OH or halogen; —NH$_2$; —NH-alkyl; —N-dialkyl; carboxyl; sulfonyl; carbamoyl; and glycosyl.

In another embodiment, a kit for imaging amyloid deposits in a subject is provided. The kit may include instructions and a liposomal composition. The instructions may direct a user to introduce into the subject a detectable quantity of the liposomal composition. The instructions may direct the user to allow sufficient time for the liposomal composition to be associated with one or more amyloid deposits. The instructions may direct the user to detect the liposomal composition associated with the one or more amyloid deposits. The liposomal composition of the kit may include a membrane. A nonradioactive magnetic resonance imaging (MRI) contrast enhancing agent may be at least one of encapsulated by or bound to the membrane. The membrane may include a phospholipid-polymer-aromatic conjugate. The aromatic moiety in the phospholipid-polymer-aromatic conjugate may be represented by Structural Formula I:

—X—Ar—R$^1$-Het    (I)

or a pharmaceutically acceptable salt thereof. In the aromatic moiety in the phospholipid-polymer-aromatic conjugate represented by Structural Formula I, X may be —R$^2$—O— or —R$^2$—N(R$^3$)—, R$^1$ may be C$_2$-C$_6$ alkyl or alkenyl. R$^2$ may be a linking group including 1 to 6 carbon atoms. R$^2$ may include one of: alkylene or alkoxyalkylene. R$^3$ may be hydrogen, C$_1$-C$_6$ alkyl, or C$_1$-C$_6$ alkoxyalkyl. Ar may be a monocyclic or polycyclic group. Ar may include at least one aromatic or heteroaromatic ring. Het may be a monocyclic or polycyclic group. Het may include at least one heteroaromatic ring. The aromatic moiety in the phospholipid-polymer-aromatic conjugate represented by Formula I may further be substituted. For example, R$^2$ may be substituted with zero, one or more of: hydroxyl, C$_1$-C$_6$ alkyl, and C$_1$-C$_6$ hydroxyalkyl. Ar, Het, R$^1$, and R$^3$ other than hydrogen may be independently substituted with zero, one or more of: halogen; —OH; alkyl, —O-alkyl, aryl, —O-aryl or —(O-alkylene)$_{1-6}$ optionally substituted with —OH or halogen; —NH$_2$; —NH-alkyl; —N-diallyl; carboxyl; sulfonyl, carbamoyl; and glycosyl.

BRIEF DESCRIPTION OF TH DRAWINGS

In the accompanying figures, chemical formulas, chemical structures, and experimental data are given that, together with the detailed description provided below, describe example embodiments of the claimed invention. The patent or application file contains at least one drawing executed in color. Copies of this patent or patent application publication with color drawing(s) will be provided by the Office upon request and payment of the necessary fee.

FIG. 1A is a table showing C Log P values and structures for various compounds.

FIG. 1C is a table showing C Log P values and structures for various compounds.

FIG. 8 is a table showing the mean diameters and polydispersity indices of liposomes prepared with the MeXO4 targeting ligand, Compound iii, and PEGylated liposomes with no ligand.

FIGS. 11A-F are images showing various exemplary amyloid imaging results in mouse models.

Figure 11C:
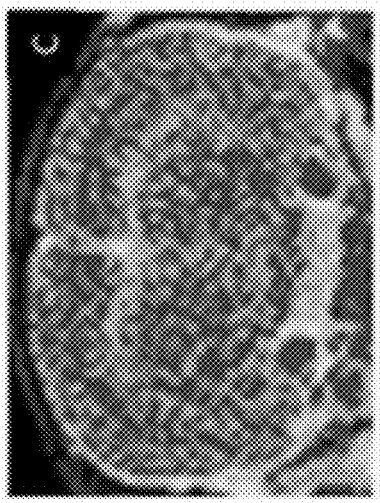
Figure 11F:
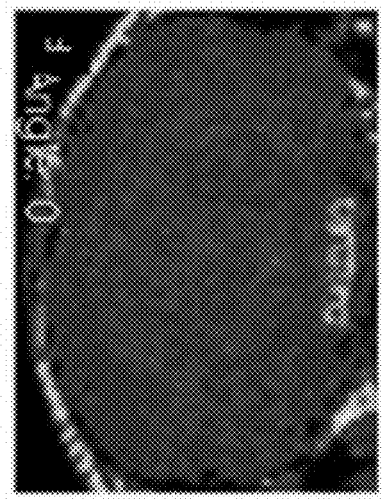
Figure 11B:
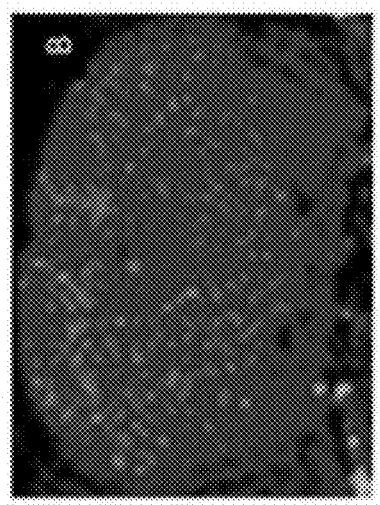
Figure 11E:
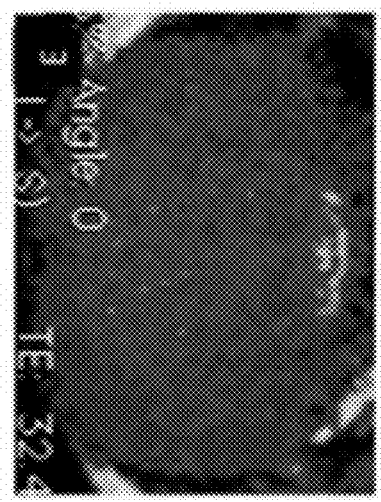
Figure 11A:
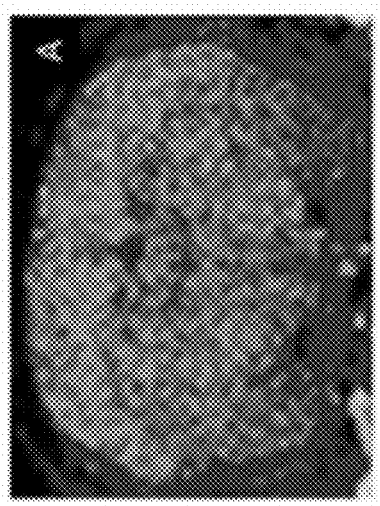

FIG. 11A depicts results for a TetO/APPswe-ind mouse, 15 months old.

FIG. 11B depicts results for a pre-injection scan of the mouse of FIG. 11A.

FIG. 11C depicts results for a Tg2576 mouse (APPswe), 9 months old.

Figure 11D:
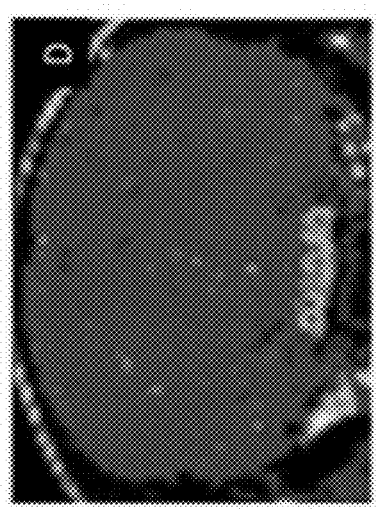

FIG. 11D depicts results for a pre-injection scan of the mouse of FIG. 11C.

FIG. 11E depicts results for a Tg2576 mouse injected with untargeted (non amyloid-binding) particles.

FIG. 11F depicts results for a non transgenic sibling of the mouse of FIG. 11E, injected with amyloid-targeted particles.

FIG. 12 is a table showing amyloid pathology score by immunohistochemistry using the 4G8 antibody, imaging agent used (Compound iii targeted or control untargeted) and individual measures of nanoparticle presence in mouse brain.

Figure 13A:
Figure 13B:
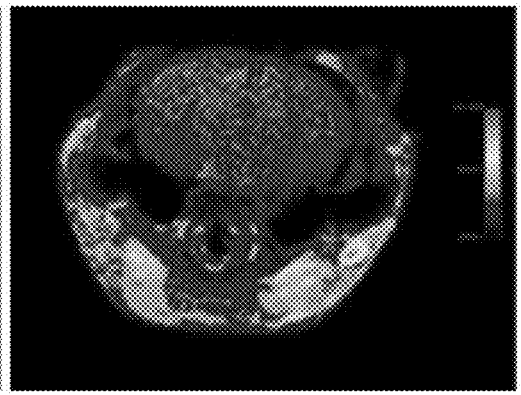
Figure 13C:
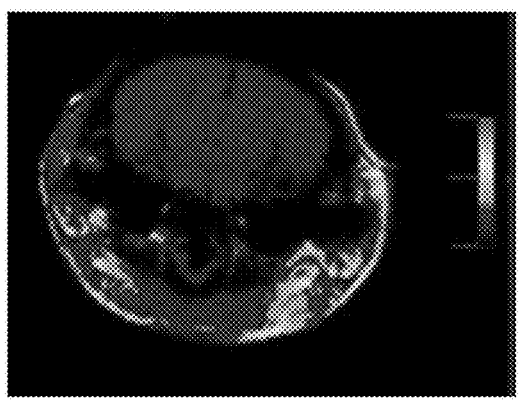
Figure 13D:
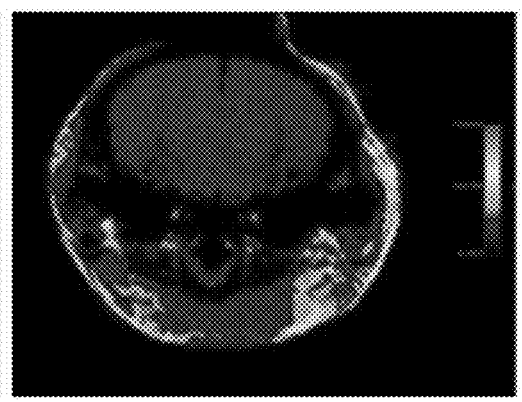
Figure 13E:
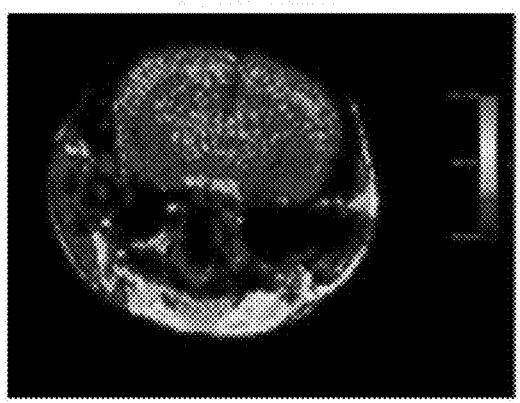
Figure 13F:
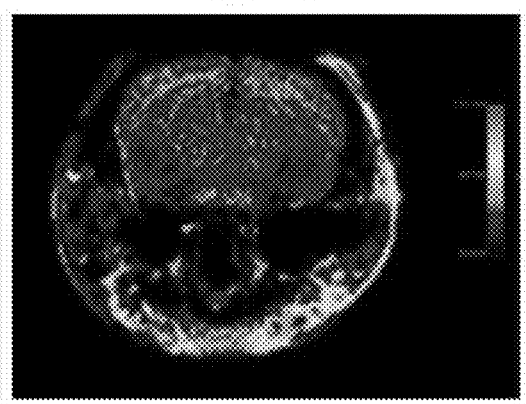
Figure 13G:
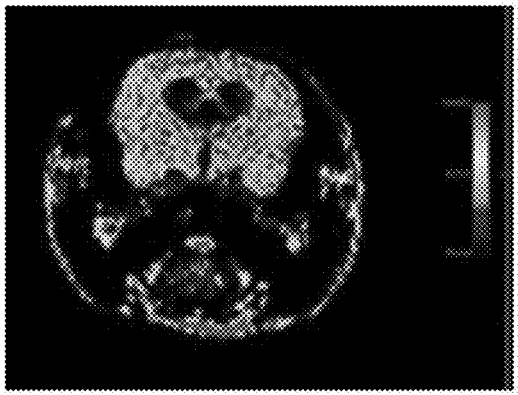
Figure 13H:
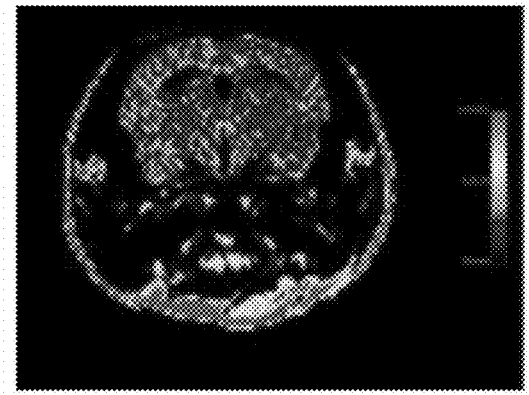
Figure 13I:
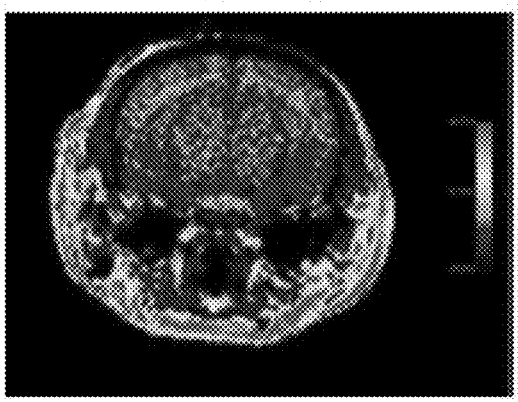
Figure 13J:
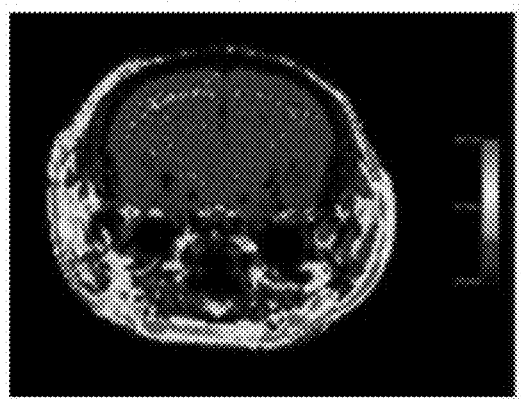
Figure 13K:
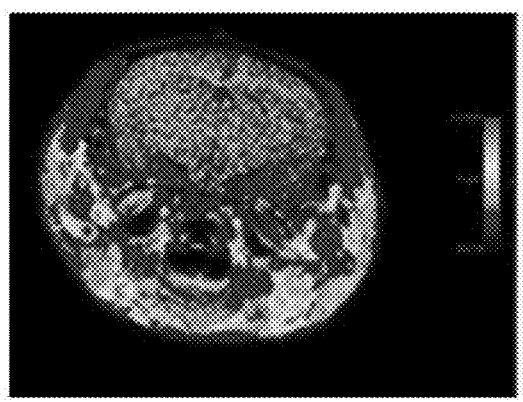
Figure 13L:
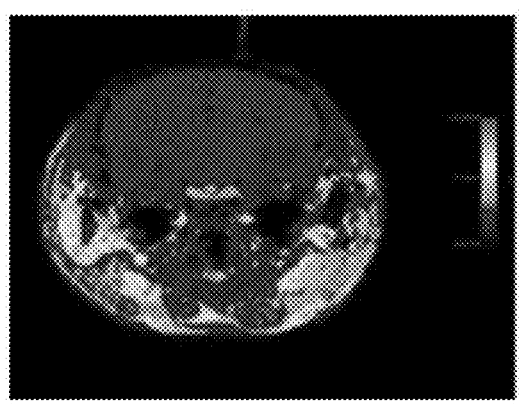
Figure 13M:
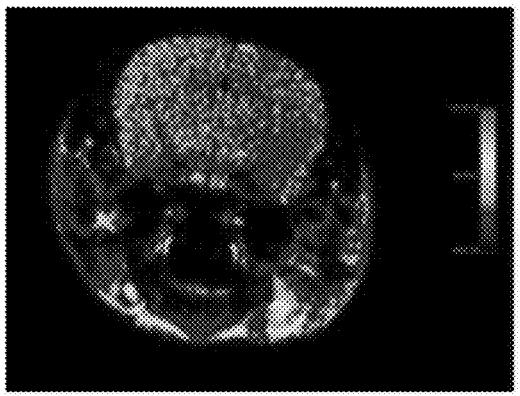
Figure 13N:
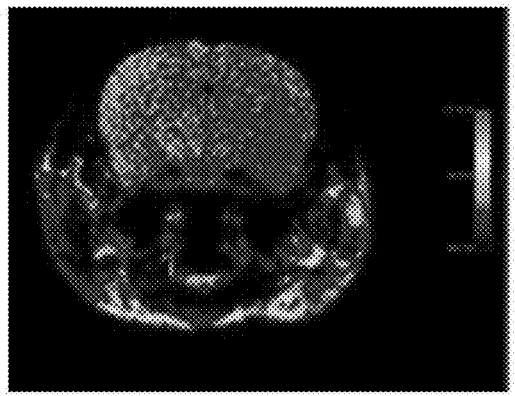
Figure 13O:
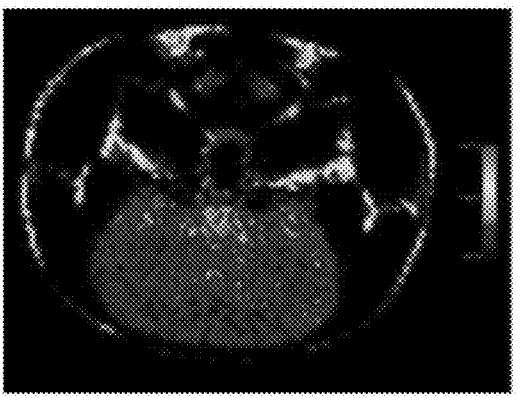
Figure 13P:
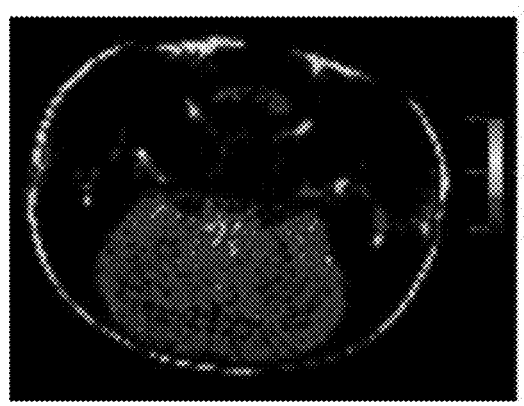
Figure 13Q:
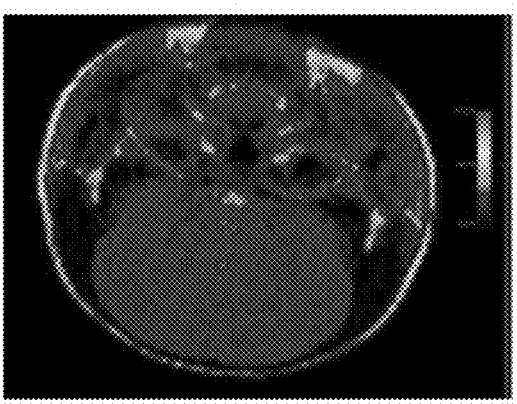
Figure 13R:
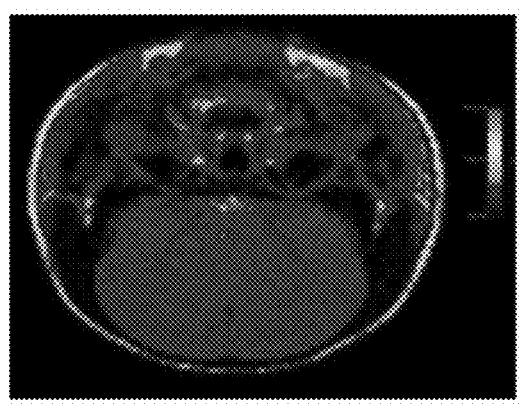
Figure 13S:
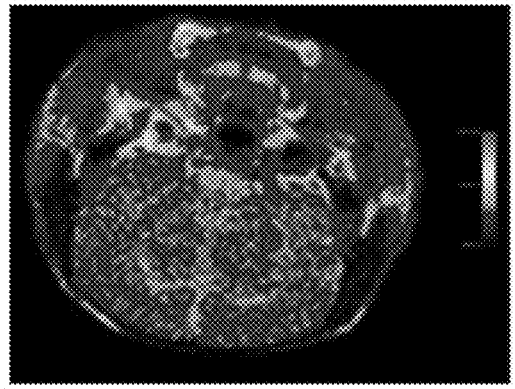
Figure 13T:
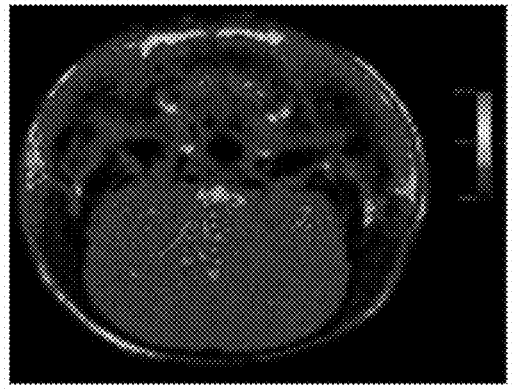
Figure 13U:
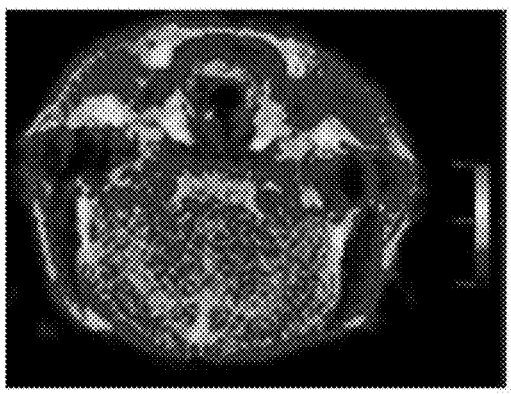
Figure 13V:
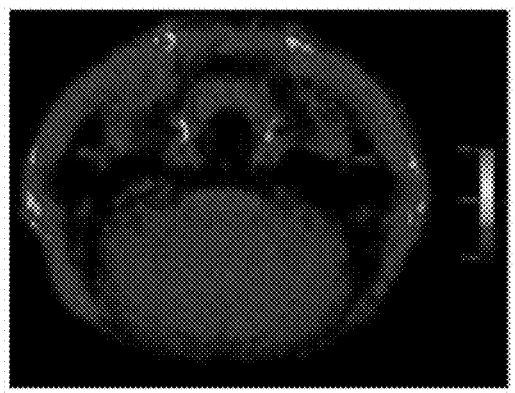
Figure 13W:
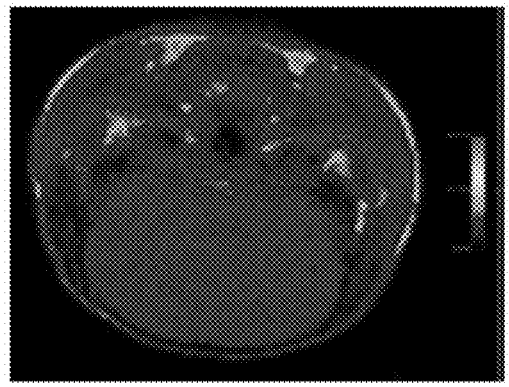
Figure 13X:
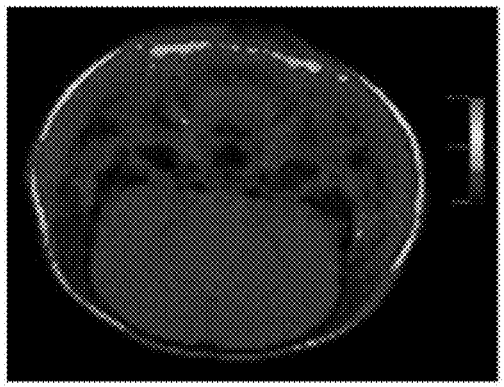
Figure 13Y:
Figure 13Z:
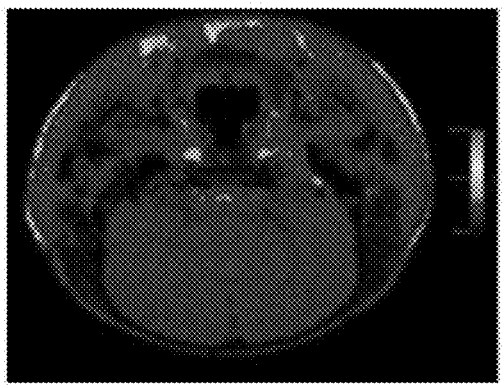

FIGS. 13A-13Z represent 13 pairs of MRI images representative of the data summarized in FIG. 12.

FIGS. 13A and 13B are 3-4 days post contrast and pre-contrast images, respectively, fin mice of strain TetO/APP 5756, genotype APP+, and Compound iii-targeted particles.

FIGS. 13C and 13D are 3-4 days post contrast and pre-contrast images, respectively, for mice of strain. TetO/APP 7110, genotype APP−, and Compound iii-targeted particles.

FIGS. 13E and 13F are 3-4 days post contrast and pre-contrast images, respectively, for mice of strain TetO/APP 5785, genotype APP+, and Compound iii-targeted particles.

FIGS. 13G and 13H are 3-4 days post contrast and pre-contrast images, respectively, for mice of strain TetO/APP 5633, genotype APP+, and Compound iii-targeted particles.

FIGS. 13I and 13J are 3-4 days post contrast and pre-contrast images, respectively, for mice of strain TetO/APP 6949, genotype APP+, and Compound iii-targeted particles.

FIGS. 13K and 13L are 3-4 days post contrast and pre-contrast images, respectively, for mice of strain TetO/APP XX21, genotype APP+, and Compound iii-targeted particles.

FIGS. 13M and 13N are 3-4 days post contrast and pre-contrast images, respectively, for mice of strain TetO/APP XXXX, genotype APP−, and Compound iii-targeted particles.

FIGS. 13O and 13P are 3-4 days post contrast and pre-contrast images, respectively, for mice of strain Tg2576 (Control 1), genotype APP−, and Compound iii-targeted particles.

FIGS. 13Q and 13R are 3-4 days post contrast and pre-contrast images, respectively, for mice of strain Tg2576 (Control 2), genotype APP−, and Compound iii-targeted, particles.

FIGS. 13S and 13T are 3-4 days post contrast and pre-contrast images, respectively, for mice of strain Tg2576 TG1, genotype APP+, and Compound iii-targeted particles.

FIGS. 13U and 13V are 3-4 days post contrast and pre-contrast images, respectively, for mice of strain Tg2576 TG2, genotype APP+, and Compound iii-targeted particles.

FIGS. 13W and 13X are 3-4 days post contrast and pre-contrast images, respectively, for mice of strain Tg2576 TG3, genotype APP+, and untargeted particles.

FIGS. 13Y and 13Z are 3-4 days post contrast and pre-contrast images, respectively, for mice of strain Tg2576 TG4, genotype APP+, and untargeted particles.

Figure 14E:
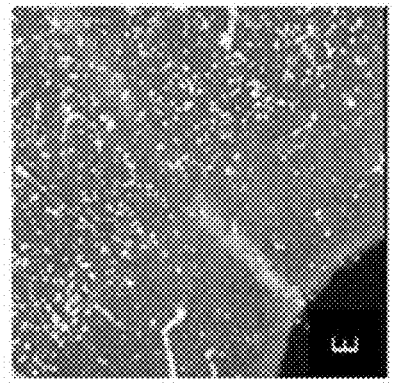
Figure 14F:
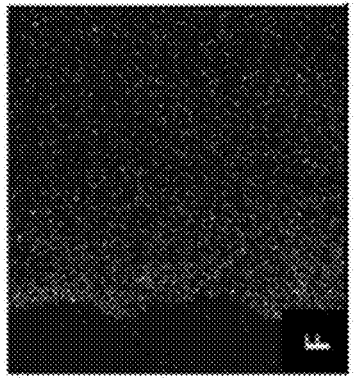
Figure 14C:
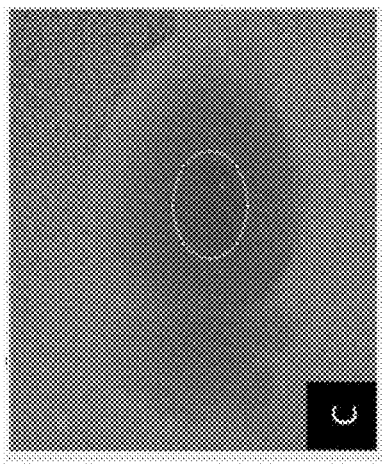
Figure 14D:
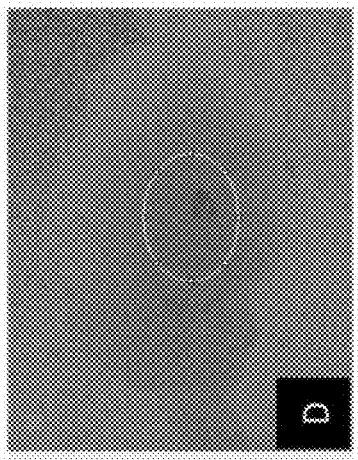
Figure 14A:

FIGS. 14A-H4 show results from near infrared imaging of mouse brains post mortem.

Figure 14B:

FIG. 14A shows confocal imaging of brain sections from Tg2576 mice with enhanced ICG signal in the cortex and hippocampus of the transgenic mice, demonstrating greater localization in the APP+ brain when compared to the non-transgenic controls (see FIG. 14B).

FIG. 14B shows confocal imaging of brain sections from non-transgenic controls under the same treatment and measurement conditions as FIG. 14A.

FIG. 14C is an image showing that the whole brains of TetO/APP+ mice demonstrated greater near infrared fluorescence than their APP− sibling controls (see FIG. 14D).

FIG. 14D are images showing that the whole brains of TetO/APP+ mice showed greater near infrared fluorescence than their APP− siblings (see FIG. 14C).

FIG. 14E is a high magnification version of FIG. 14A showing the characteristic punctuate structure of amyloid deposits.

FIG. 14F is a high magnification version of FIG. 14B.

FIG. 14G1-G4 are fluorescence colocalization images for a cluster of 3 plaques.

FIG. 14G1 (green) shows a fluorescently labeled 4G8 antibody bound to the cluster of 3 amyloid plaques.

Figure 2:
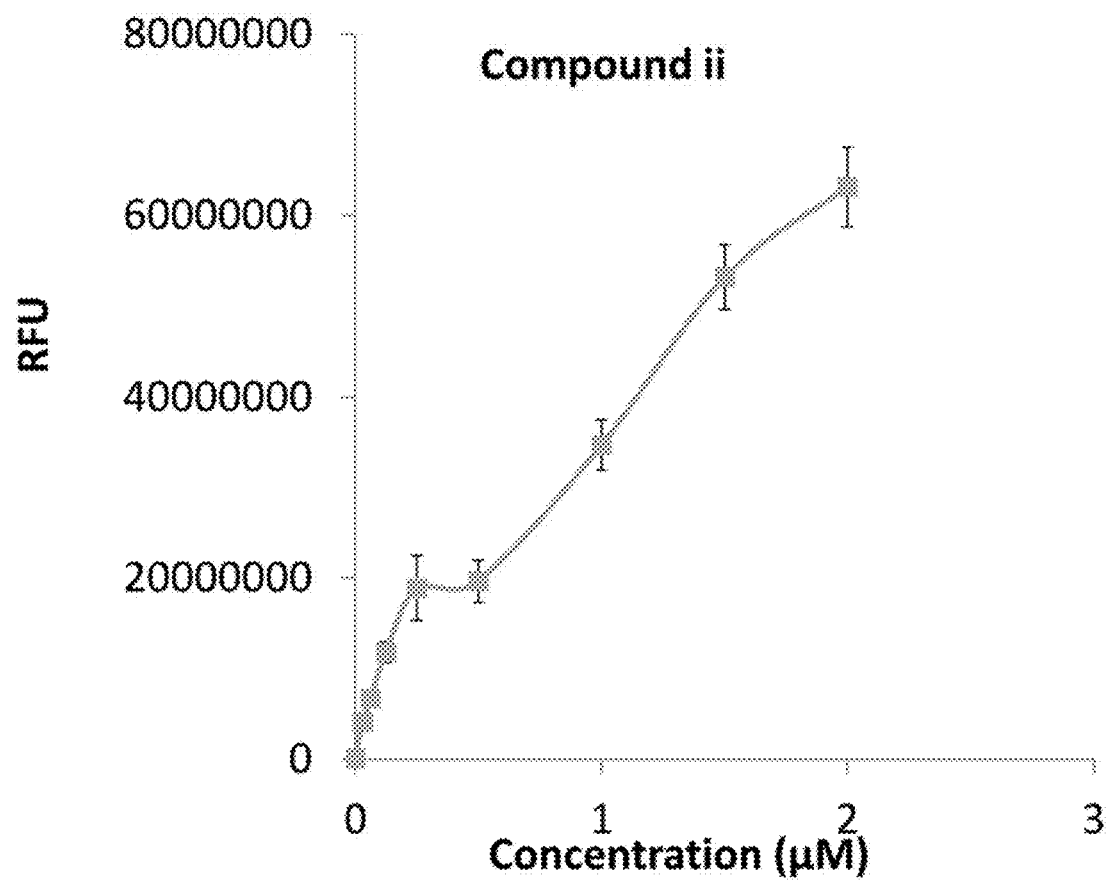
FIG. 2 is a binding profile showing the binding of Compound ii to fibrils, plotted as relative fluorescence unit (RFU) versus concentration in μM.

FIG. 14G2 (red) shows ICG bound, to the cluster of 3 amyloid plaques.

Figure 3:
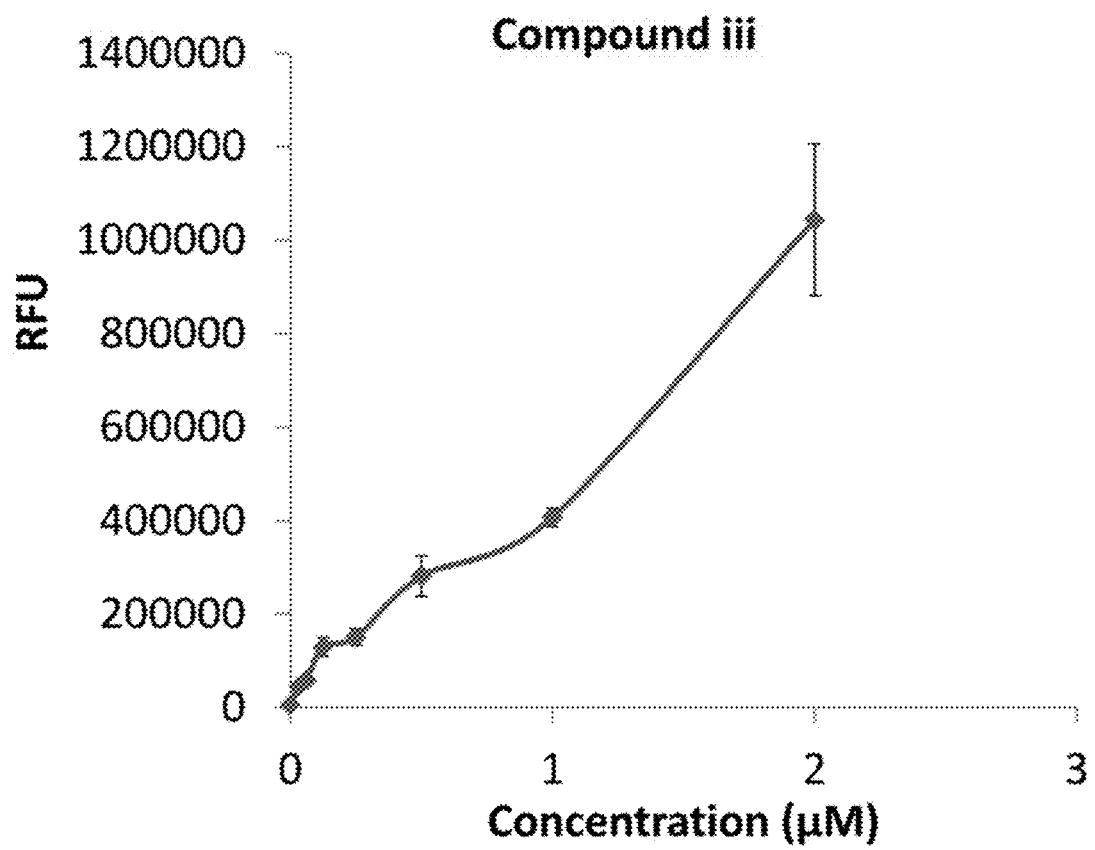
FIG. 3 is a binding profile showing the binding of Compound iii to fibrils, plotted as relative fluorescence unit (RFU) versus concentration in μM.

FIG. 14G3 (blue) shows Compound iii bound to the cluster of 3 amyloid plaques.

Figure 4:
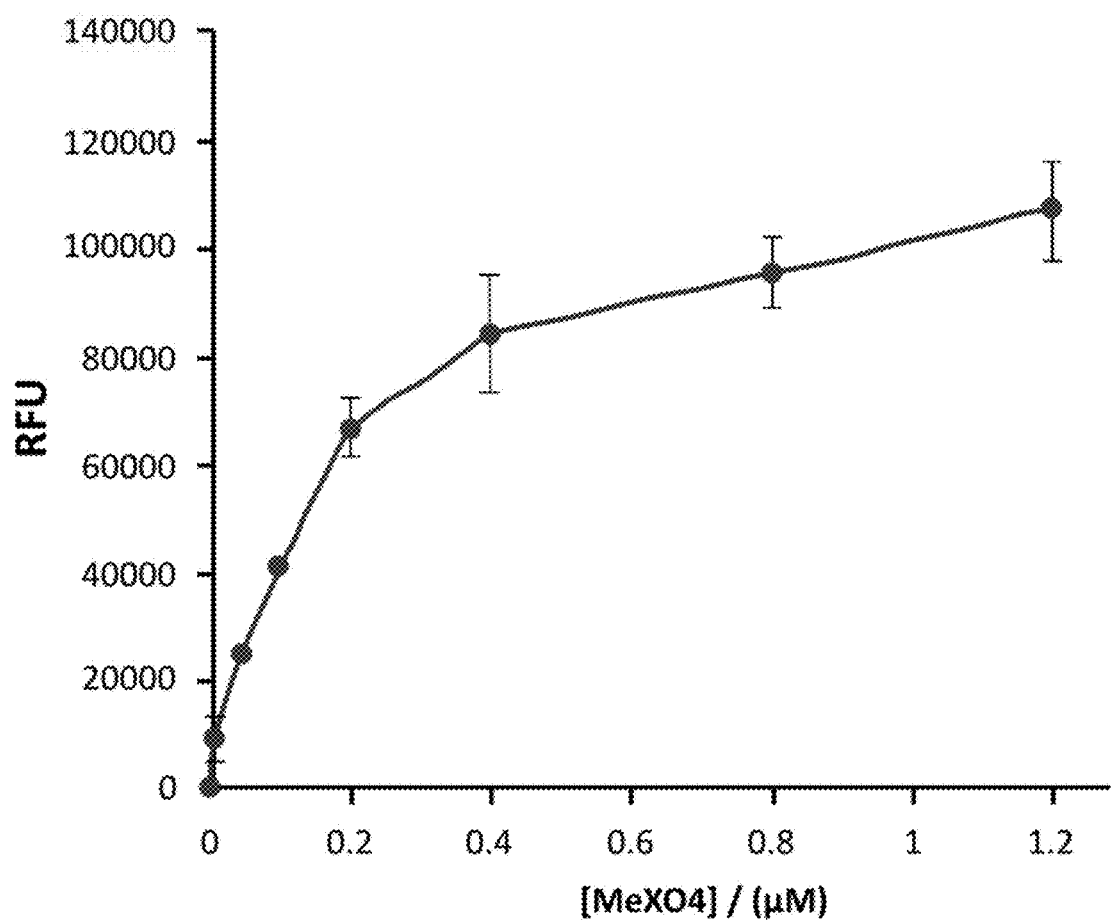
FIG. 4 is a binding profile showing the binding of MeXO4 (a previous compound) to fibrils, plotted as relative fluorescence unit (RFU) versus concentration in μM.

FIG. 14G4 shows a combination of FIGS. 14G1, 14G2, and 14G3.

FIG. 14H1-H4 are fluorescence colocalization images for a single plaque.

FIG. 14H1 (green) shows a fluorescently labeled 4G8 antibody bound to the single plaque.

FIG. 14H2 (red) shows ICG bound to the single plaque.

FIG. 14H3 (blue) shows Compound iii bound to the single plaque.

FIG. 14H4 shows a combination of FIGS. 14G1, 14G2, and 14G3.

DETAILED DESCRIPTION

In various embodiments, a liposomal composition is provided. The liposomal composition may include a membrane. The membrane may include a phospholipid-polymer-aromatic conjugate. The aromatic moiety in the phospholipid-polymer-aromatic conjugate may be represented by Structural Formula I:

—X—Ar—R$^1$-Het                (I)

or a pharmaceutically acceptable salt thereof. In the aromatic moiety in the phospholipid-polymer-aromatic conjugate represented by Structural Formula I, X may be —R$^2$—O— or —R$^2$—N(R$^3$)—. R$^1$ may be C$_2$-C$_6$ alkyl or alkenyl. R$^2$ may be a linking group including 1 to 6 carbon atoms. R$^2$ may include one of: alkylene or alkoxyalkylene. R$^3$ may be hydrogen, C$_1$-C$_6$ alkyl, or C$_1$-C$_6$ alkoxyalkyl. Ar may be a monocyclic or polycyclic group. Ar may include at least one aromatic or heteroaromatic ring. Het may be a monocyclic or polycyclic group. Het may include at least one heteroaromatic ring. The aromatic moiety in the phospholipid-polymer-aromatic conjugate represented by Formula I may further be substituted. For example, R$^2$ may be substituted with zero, one or more of: hydroxyl, C$_1$-C$_6$ alkyl, and C$_1$-C$_6$ hydroxyalkyl. Ar, Het, R$^1$, and R$^3$ other than hydrogen may be independently substituted with zero, one or more of: halogen; —OH; alkyl, —O-alkyl, aryl, —O-aryl or —(O-alkylene)$_{1-6}$ optionally substituted with —OH or halogen; —NH$_2$; —NH-alkyl; —N-dialkyl; carboxyl; sulfonyl; carbamoyl; and glycosyl.

In several embodiments, a phospholipid-polymer-aromatic conjugate is provided. The aromatic moiety in the phospholipid-polymer-aromatic conjugate may be represented by Structural Formula I:

—X—Ar—R$^1$-Het                (I)

or a pharmaceutically acceptable salt thereof, wherein the variables, e.g., X, Ar, R$^1$, Het, and the like may represent the same moieties as in Structural Formula I of the liposome composition or Structural Formula H of the compound as described herein.

In some embodiments, a compound represented by Structural Formula II is provided:

R$^5$—Ar—R$^1$-Het                (II)

or a pharmaceutically acceptable salt thereof, wherein the variables, e.g., Ar, R$^1$, Het, R$^5$ and the like may represent the same moieties as in Structural Formula I of the liposome composition or Structural Formula I of the phospholipid-polymer-aromatic conjugate as described herein.

In Structural Formula R may be hydrogen, hydroxyl, H—R$^2$—, HO—R$^2$—, H—R$^2$—N(R$^3$)—, or HO—R$^2$—N(R$^3$)—. In some embodiments R$^5$ may be hydroxyl, H—R$^2$—, HO—R$^2$—, H—R$_2$—N(R$^3$)—, or HO—R$^2$—N(R$^3$)—. R$^5$ may be H—R$^2$—, HO—R$^2$—, H—R$^2$—N(R$^3$)—, or HO—R$^2$—N(R$^3$)—. R$^5$ may be H—R$^2$— or H—R$_2$—N(R$^3$)—. R$^5$ may be HO—R$^2$— or HO—R$^2$—N(R$^3$)—. R$^5$ may be H—R$^2$— or HO—R$^2$—.

In various embodiments of Structural Formulas I and II, R$^1$ may be C$_2$ alkyl or alkenyl. For example, R$^1$ may be C$_2$-C$_6$ alkenyl. R$^1$ may be C$_2$-C$_6$ alkenyl in a trans or cis configuration, for example, trans, R$^1$ may be trans 1,2-ethenyl.

In some embodiments of Structural Formulas I and II, one, two, three, or four ring atoms of the heteroaromatic rings included by Ar and Het each independently may be one of: N, O, or S. For example, two ring atoms of the heteroaromatic ring represented by Het each may be one of: N, O, or S. Het and/or Ar may each include at least one heteroaromatic ring selected from the group consisting of: pyridine, pyrimidine, pyrazine, pyridazine, thiophene, furan, pyrrole, thiazole, oxazole, diazole, thiadiazole, oxadiazole, and triazole. Het and/or Ar may each include, for example, one of: phenyl, pyridine, pyrimidine, pyrazine, pyridazine, thiophene, furan, pyrrole, thiazole, oxazole, diazole, thiadiazole, oxadiazole, triazole, benzofuran, indole, benzothiophene, thienopyrimidine, benzooxazole, benzothiazole, benzooxadiazole, or benzothiadiazole. For example, Het may include one of: pyridine, pyrimidine, thienopyrimidine, or benzothiazole. Ar may include one of phenyl or indole.

In several embodiments of Structural Formulas I and III, Ar and Het may be independently substituted with zero, one or more of: F, Cl, Br, I, alkyl, aryl, —OH, —O-alkyl, —O-aryl, —NH$_2$, —NH-alkyl, —N-dialkyl, carboxyl, sulfonyl, carbamoyl, and glycosyl.

In various embodiments of Structural Formulas I and II, the aromatic moiety in the phospholipid-polymer-aromatic conjugate may be represented by —O—Ar—R$^1$-Het. The compound may be represented by H—O—Ar—R$^1$-Het. Het and/or Ar may be substituted by —O-alkyl. Het and/or Ar may be substituted by methoxy, Het may be monocyclic. One or two ring atoms of the heteroaromatic ring included by Het may be N.

In some embodiments of Structural Formula I, the aromatic moiety in the phospholipid-polymer-aromatic conjugate may be represented by:

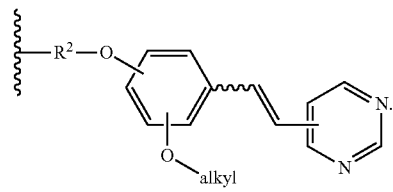

Similarly, the compound of Structural Formula it may be represented by:

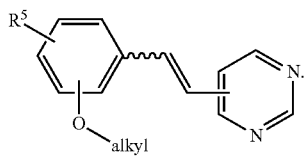

$R^5$ may be H, hydroxyl, H—$R^2$—, HO—$R^2$—, H—$R^2$—N($R^3$)—, or HO—$R^2$—N($R^3$)—.

In some embodiments, the aromatic moiety in the phospholipid-polymer-aromatic conjugate may be represented by:

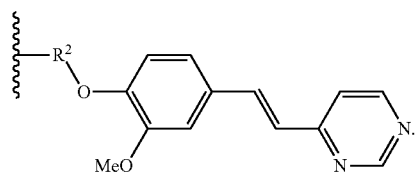

Similarly, the compound of Structural Formula II may be represented by:

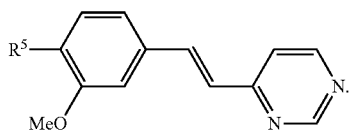

$R^5$ may be H, hydroxyl, H—$R^2$—, HO—$R^2$—, H—$R^2$—N($R^3$)—, or HO—$R^2$—N($R^3$)—. In some embodiments, $R^5$ may be hydroxyl. For example, the compound may be:

Compound i

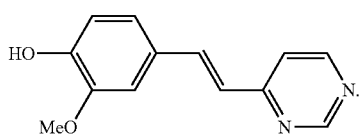

In several embodiments, the phospholipid-polymer-aromatic conjugate may be represented by:

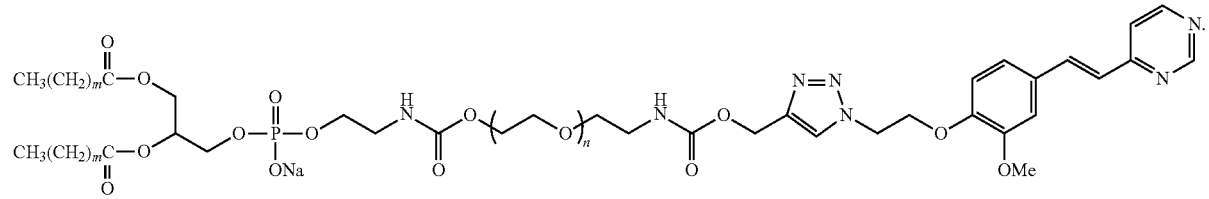

The variable n may be any integer from about 10 to about 100, for example, about 60 to about 100, about 70 to about 90, about 75 to about 85, about 77, and the like. The variable m may be one of: 12, 13, 14, 15, 16, 17, or 18. For example, n may be 77 and m may be 14. In another example, n may be 77 and m may be 16.

In various embodiments, the aromatic moiety in the phospholipid-polymer-aromatic conjugate may be represented by —$R^2$—N($R^3$)—Ar—$R^1$-Het. Ar may be unsubstituted. Ar may be monocyclic. Ar may include a carbocyclic aromatic ring, for example, Ar may be a phenyl ring. Ar may be indole. For example, Ar may be unsubstituted 1,4-phenylene or unsubstituted 1,5-indolyl. Het may be monocyclic. One or two ring atoms of the heteroaromatic ring included by Het may be N. $R^2$ may be substituted with zero, one or more —OH. $R^3$ may be $C_1$-$C_6$ alkyl substituted with zero, one or more of: —OH and alkyl optionally substituted with one or more —OH. For example, $R^3$ may be $C_1$-$C_3$ alkyl or hydroxyalkyl.

In some embodiments, the aromatic moiety in the phospholipid-polymer-aromatic conjugate may be represented by:

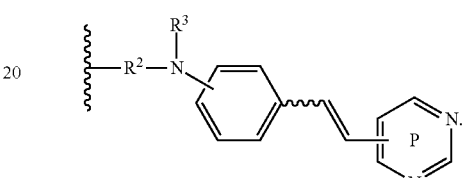

Pyrimidine P may be substituted with zero, one, or more of —OH, —O-alkyl, and —$NH_2$. For example, the aromatic moiety in the phospholipid-polymer-aromatic conjugate may be represented by:

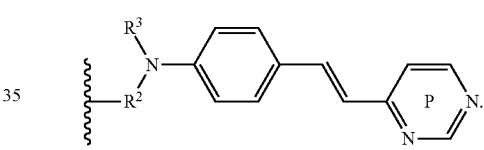

Pyrimidine P may be substituted with zero, one, or two of —OH, —OMe, and —$NH_2$. Similarly, the compound of Structural Formula II may be represented by:

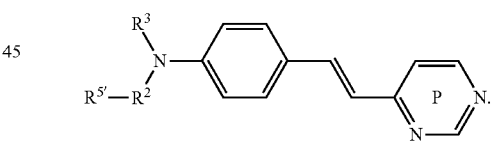

$R^5$ may be hydrogen or hydroxyl.

In several embodiments, the aromatic moiety in the phospholipid-polymer-aromatic conjugate may be represented by one of:

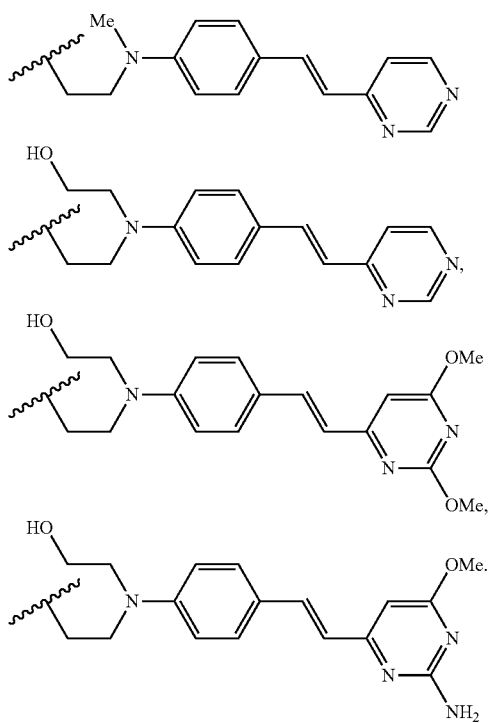
Similarly, the compound of Structural Formula II may be represented by:
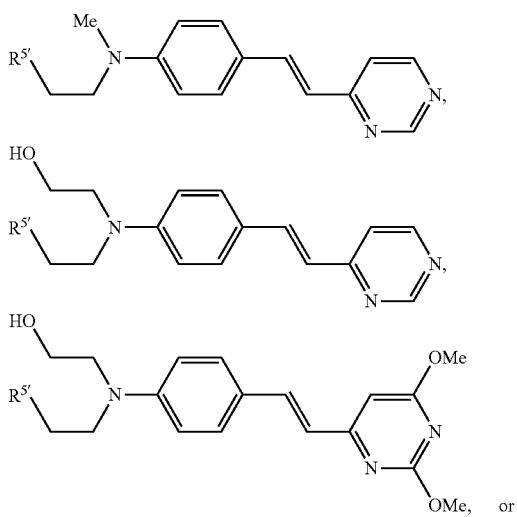
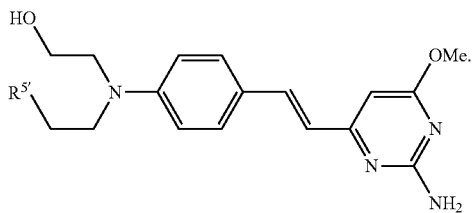
$R^{5'}$ may be hydrogen or hydroxyl. For example, the compound may be one of:
Compound ii
Compound iii
Compound xi
Compound xiii
In various embodiments, the phospholipid-polymer-aromatic conjugate may be represented by one of:
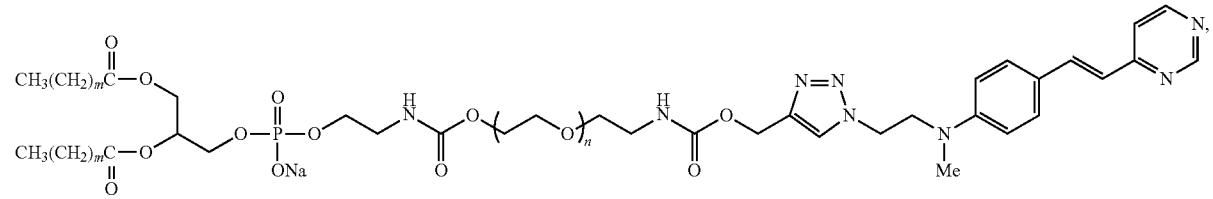

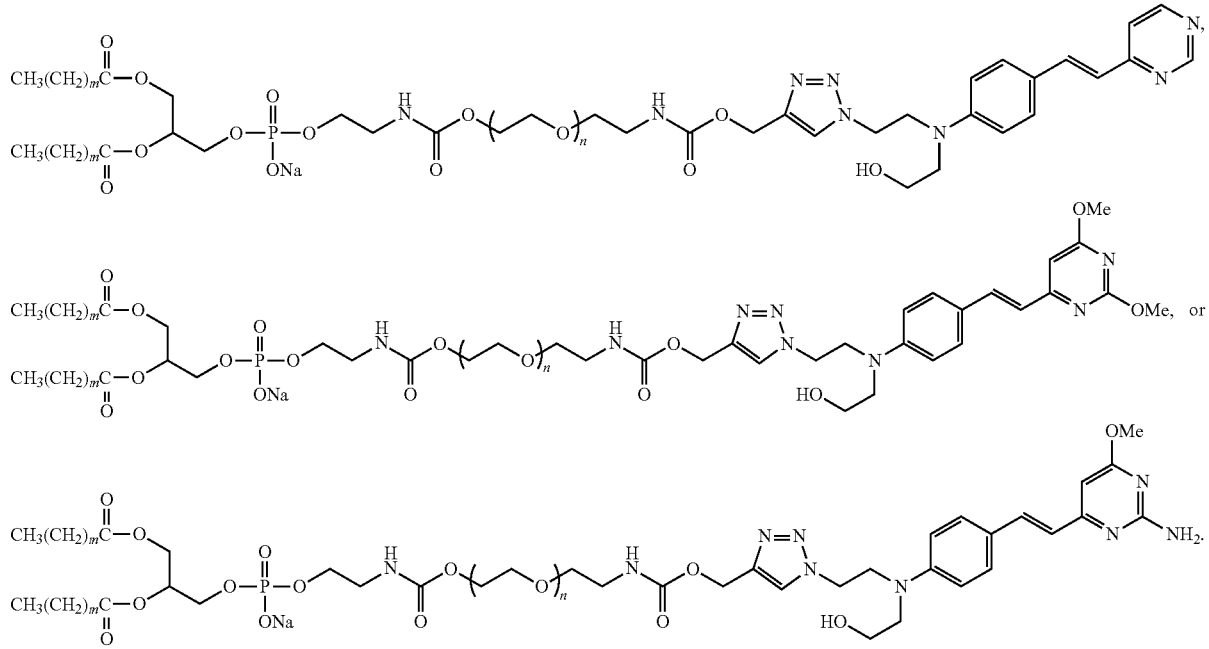

The variable n may be any integer from about 10 to about 100, for example, about 60 to about 100, about 70 to about 90, about 75 to about 85, or about 77. The variable m may be one of 12, 13, 14, 15, 16, 17, or 18. For example, n may be 77 and m may be 14. In another example, n may be 77 and m may be 16.

In some embodiments, Het may include a bicyclic heteroaromatic group. For example, one, two, three, or four ring atoms of the bicyclic heteroaromatic group included by Het each may be one of: N, O, or S. For example, the aromatic moiety in the phospholipid-polymer-aromatic conjugate may be represented by:

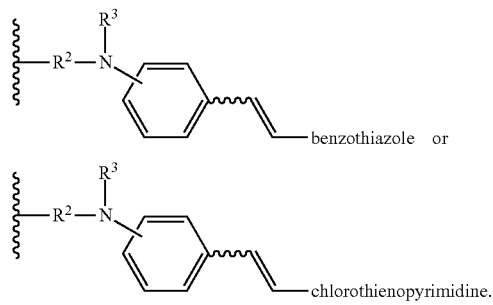

Further, for example, the aromatic moiety in the phospholipid-polymer-aromatic conjugate may be represented by:

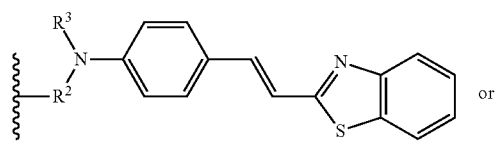

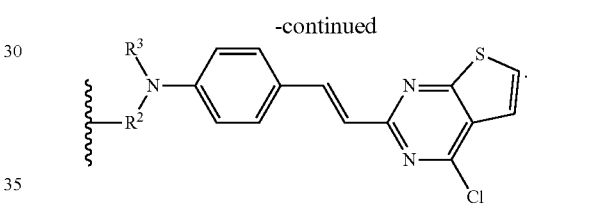

Similarly, the compound of Structural Formula II may be represented by:

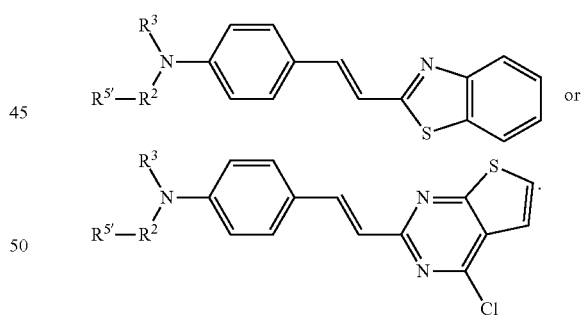

$R^{5'}$ may be hydrogen or hydroxyl.

In several embodiments, the aromatic moiety in the phospholipid-polymer-aromatic conjugate may be represented by:

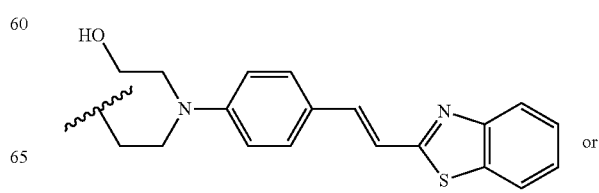

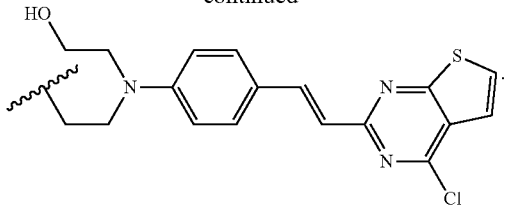

Similarly, the compound of Structural Formula II may be represented by:

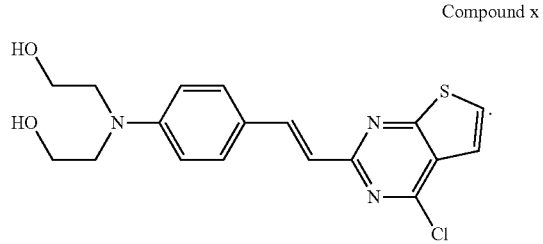

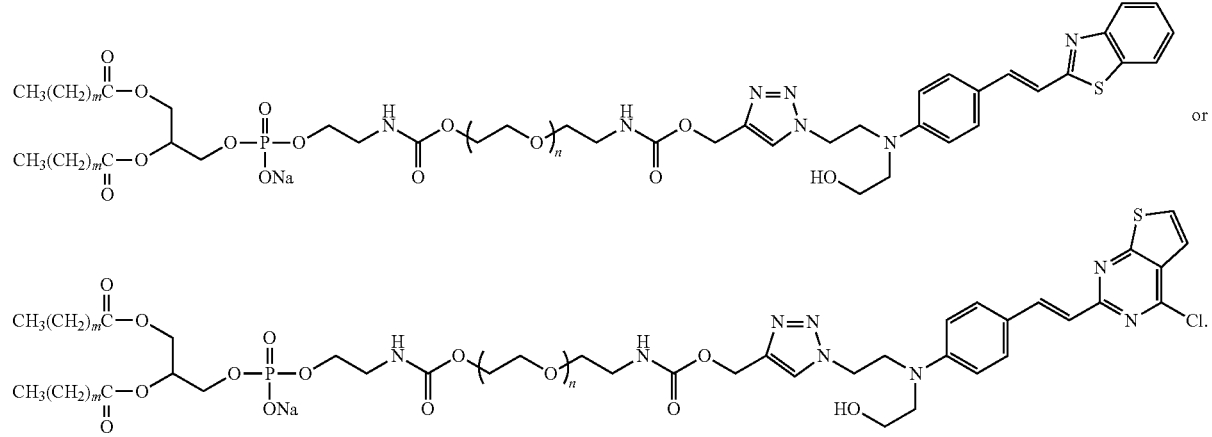

-continued

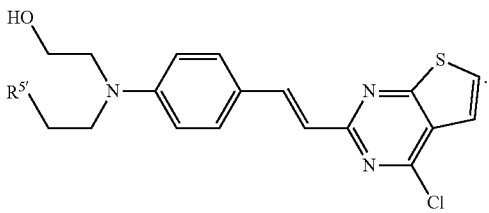

R[5'] may be hydrogen or hydroxyl. For example, the compound may be represented by:

Compound iv

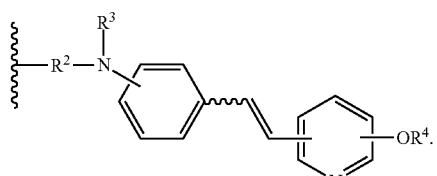

or

-continued

Compound x

In several embodiments, the phospholipid-polymer-aromatic conjugate may be represented by:

The variable n may be any integer from about 10 to about 100, for example, about 60 to about 100, about 70 to about 90, about 75 to about 85, or about 77. The variable m may be one of: 12, 13, 14, 15, 16, 17, or 18. For example, n may be 77 and m may be 14. In another example, n may be 77 and m may be 16.

In various embodiments, the aromatic moiety in the phospholipid-polymer-aromatic conjugate may be represented by:

Similarly, the compound of Structural Formula II may be represented by:

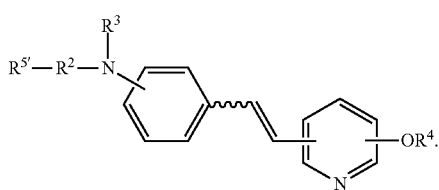

$R^{5\prime}$ may be hydrogen or hydroxyl. In the above structures, $R^4$ may be H. $R^4$ may be alkyl optionally substituted with —OH. —$OR^4$ may be —(O-alkylene)$_{1-6}$ optionally substituted with —OH.

In some embodiments, the aromatic moiety in the phospholipid-polymer-aromatic conjugate may be represented by one of:

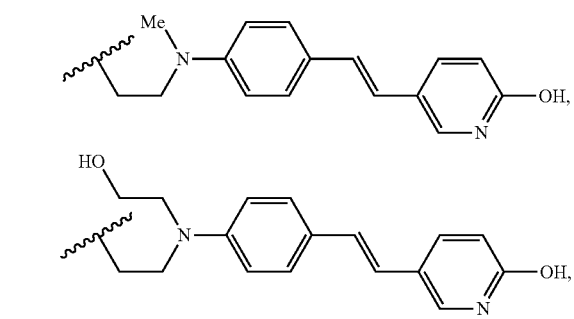

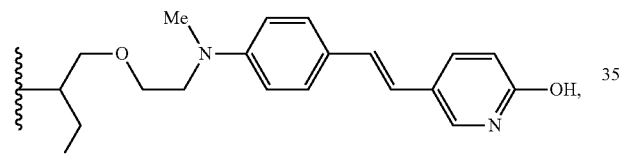

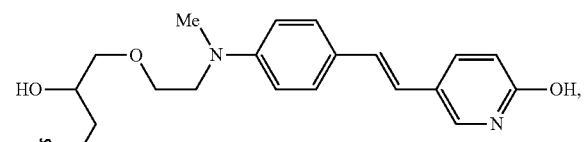

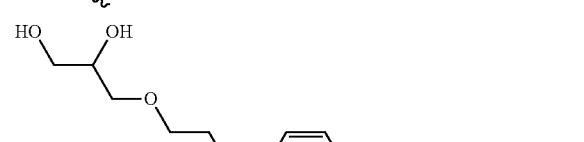

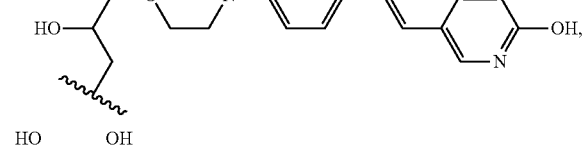

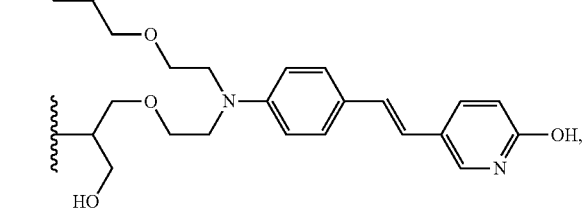

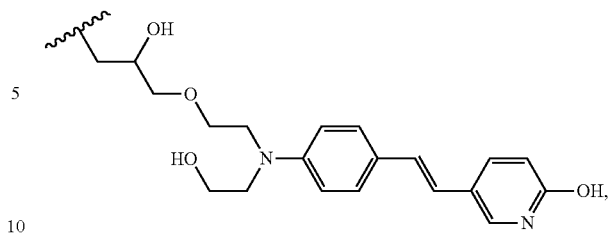

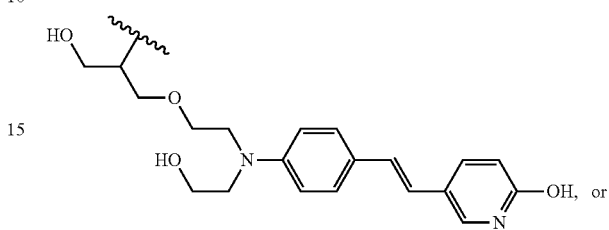

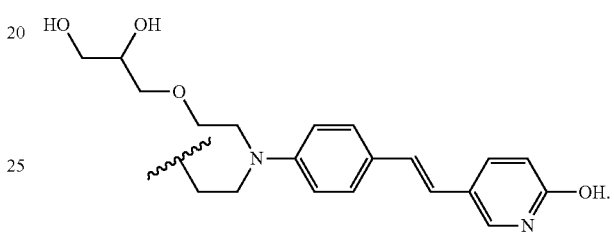

Similarly, the compound of Structural Formula II may be represented by:

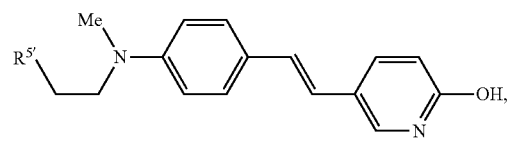

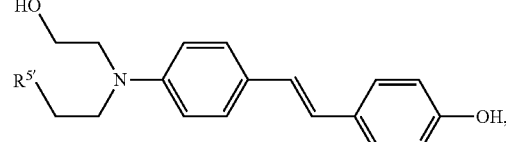

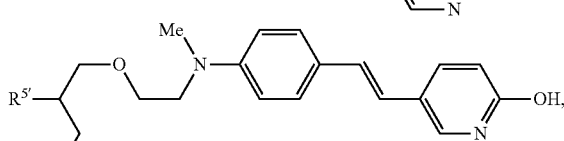

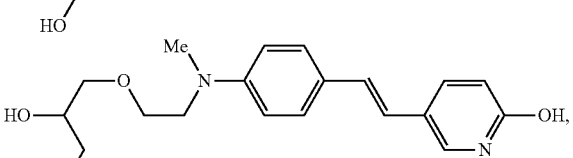

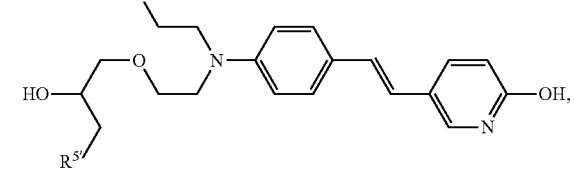

19
-continued
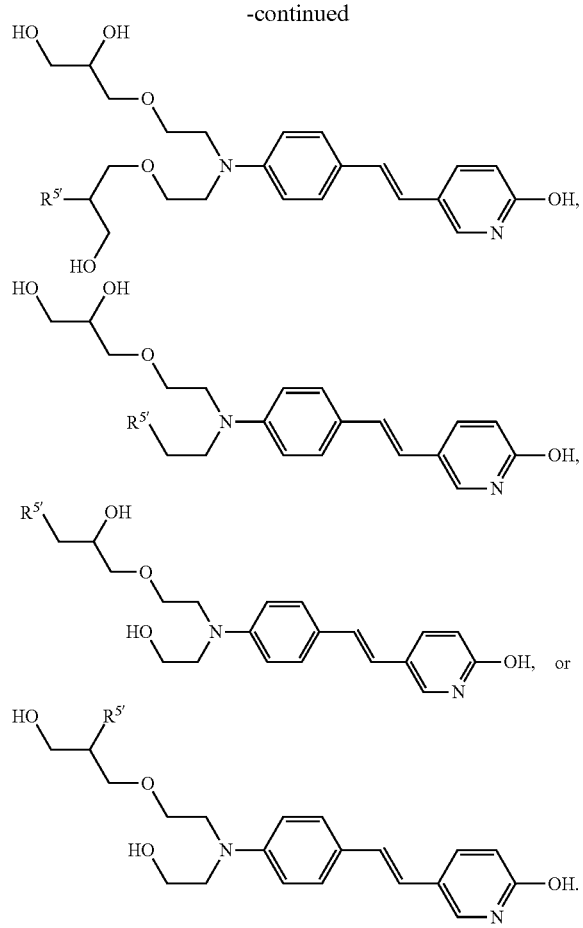
R[5'] may be hydrogen or hydroxyl. For example, the compound may be represented by one of:
Compound v
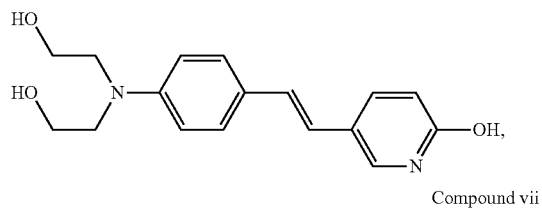
20
-continued
Compound vi
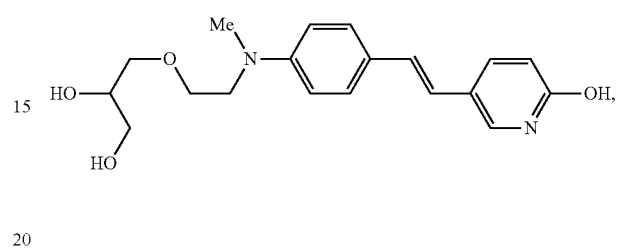
Compound vii
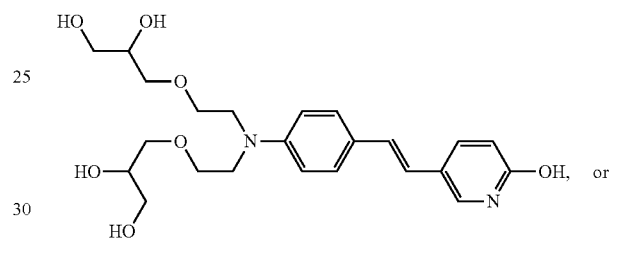
Compound viii
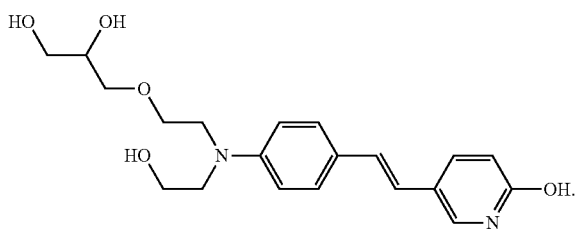
Compound ix
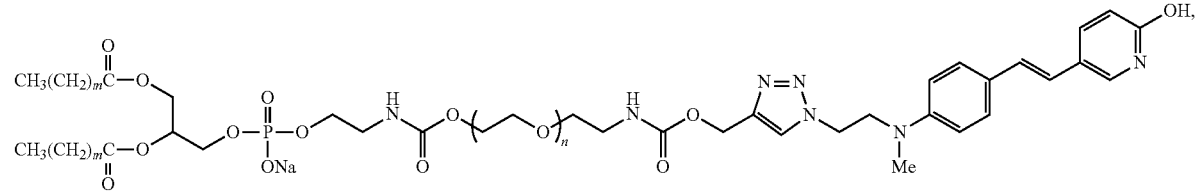
In several embodiments, the phospholipid-polymer-aromatic conjugate may be represented by one of:
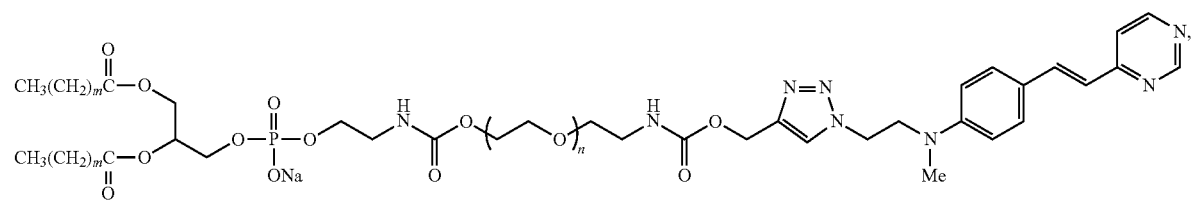

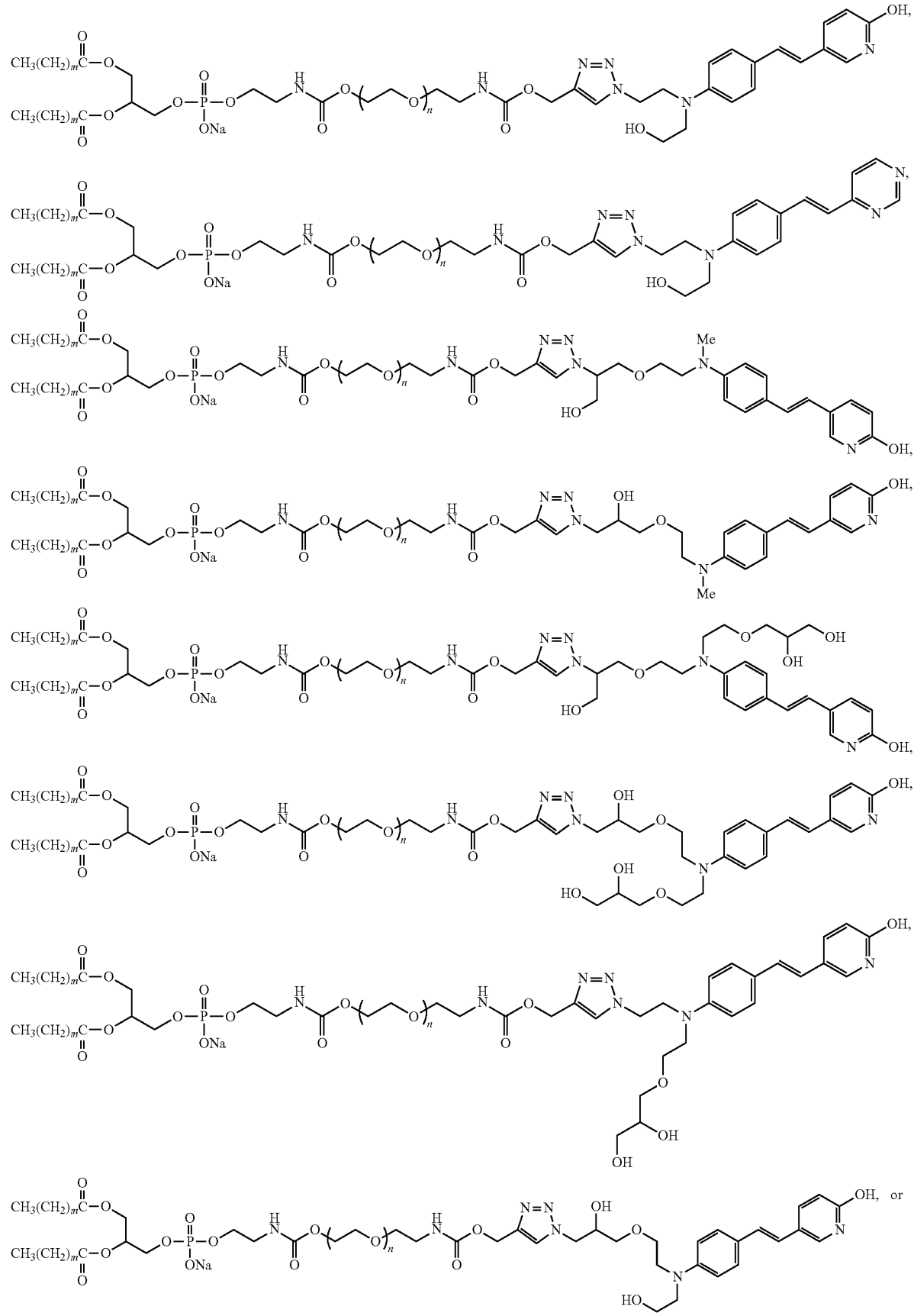

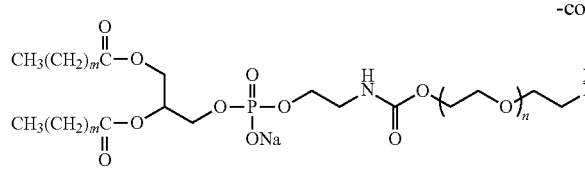

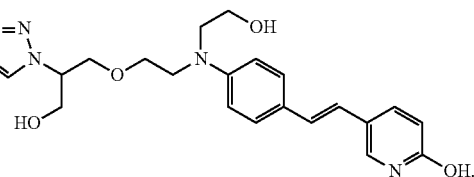

The variable in may be any integer from about 10 to about 100, for example, about 60 to about 100, about 70 to about 90, about 75 to about 85, or about 77. The variable in may be one of: 12, 13, 14, 15, 16, 17, or 18. For example, n may be 77 and in may be 14. In another example, n may be 77 and in may be 16.

In various embodiments, the aromatic moiety in the phospholipid-polymer-aromatic conjugate may be represented by:

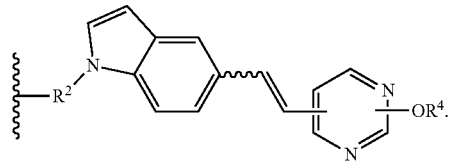

$R^4$ may be H. $R^4$ may be alkyl optionally substituted with —OH. —$OR^4$ may be —(O-alkylene)$_{1-6}$ optionally substituted with —OH. Similarly, the compound of Structural Formula II may be represented by:

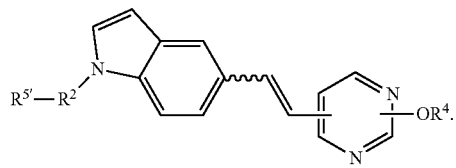

$R^{5'}$ may be hydrogen or hydroxyl. Further, for example, the aromatic moiety in the phospholipid-polymer-aromatic conjugate may be represented by:

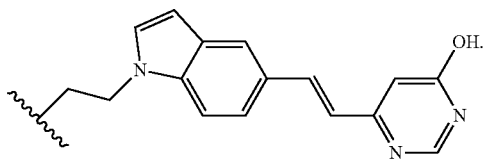 [SMILES: *CCn1ccc2cc(/C=C/c3cc(O)ncn3)ccc21]

The compound of Structural Formula II may be represented by:

Compound xii

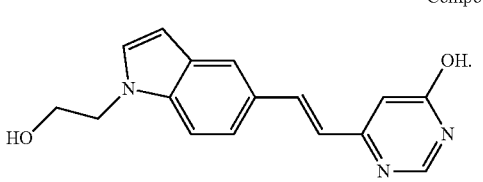

The phospholipid-polymer-aromatic conjugate may be represented by:

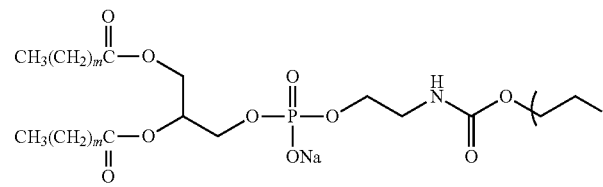

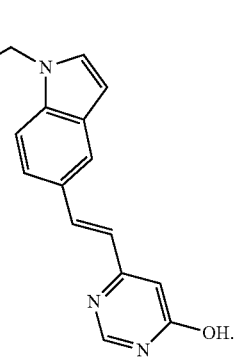

The variable n may be an integer from about 60 to about 100; and m may be one of: 12, 13, 14, 15, 16, 17, or 18.

In various embodiments, the compounds may include any one of Compounds i-xiii.

In some embodiments, the phospholipid moiety in the phospholipid-polymer-aromatic conjugate may be represented by the following structural formula:

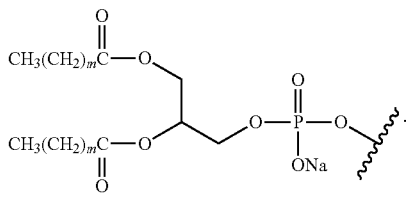

The variable m may be one of: 12, 13, 14, 15, 16, 17, or 18. For example, m may be 14 or 16. In various embodiments, the phospholipid moiety in the phospholipid-polymer-aromatic conjugate may be one of: 1,2-dipalmitoyl-sn-glycero-3-phosphocholine (DPPC), 1,2-distearoyl-sn-glycero-3-phosphoethanolamine (DSPE), 1,2-distearoyl-sn-glycero-3-phosphocholine (DSPC), or 1,2-Dipalmitoyl-sn-glycero-3-phosphoethanolamine (DPPE). Suitable phospholipids may also include those disclosed herein, and may further include those disclosed in U.S. Pat. No. 7,785,568 issued to Annapragada et al, which is incorporated by reference herein in its entirety. Suitable polymer derivatized phospholipids may include those disclosed herein, and may further include those disclosed in U.S. Pat. No. 7,785,568.

In some embodiments, the polymer moiety in the phospholipid-polymer-aromatic conjugate may include a hydrophilic polymer, e.g., a poly(alkylene oxide). The hydrophilic poly(alkylene oxide) may include between about 10 and about 100 repeat units, and having, e.g., a molecular weight ranging from 500-10,000 Daltons. The hydrophilic poly (alkylene oxide) may include, for example, poly(ethylene oxide), poly (propylene oxide) and the like. The polymer moiety in the phospholipid-polymer-aromatic conjugate may be conjugated to the phospholipid moiety via an amide or carbamate group. The polymer moiety in the phospholipid-polymer-aromatic conjugate may be conjugated to the aromatic moiety via an amide, carbamate, poly (alkylene oxide), triazole, combinations thereof, and the like. For example, the polymer moiety in the phospholipid-polymer-aromatic conjugate may be represented by one of the following structural formula:

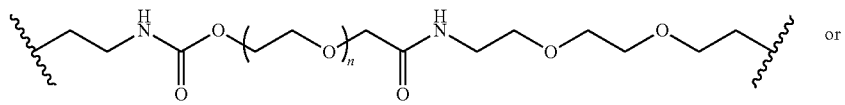 or

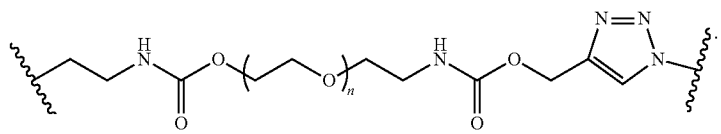.

The variable n may be any integer from about 10 to about 100, for example, about 60 to about 100, about 70 to about 90, about 75 to about 85, or about 77.

In several embodiments, the phospholipid-polymer moiety in the phospholipid-polymer-aromatic conjugate may be represented by one of the following structural formula:

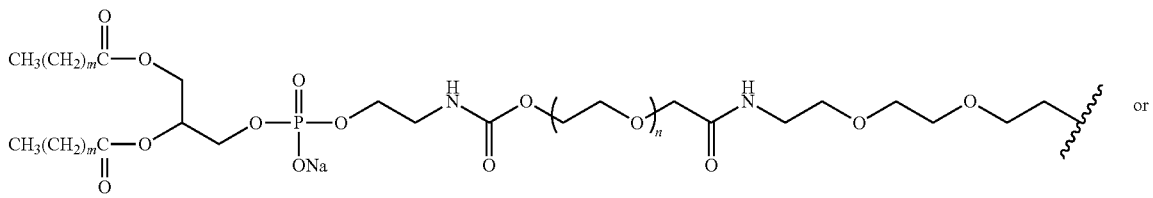 or

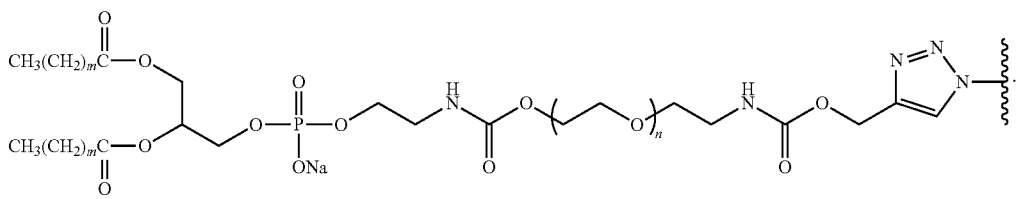

The variable n may be any integer from about 10 to about 100, for example, about 60 to about 100, about 70 to about 90, about 75 to about 85, or about 77. The variable m may be one of: 12, 13, 14, 15, 16, 17, or 18. For example, n may be 77 and m may be 14. In another example, n may be 77 and m may be 16.

In various embodiments, the liposomal composition may further include a nonradioactive magnetic resonance imaging (MRI) contrast enhancing agent that may be at least one of encapsulated by or bound to the membrane. For example, the nonradioactive magnetic resonance imaging (MRI) contrast enhancing agent may be both encapsulated by and bound to the membrane, e.g., to provide a dual contrast agent liposome. The liposomal composition may be characterized by a per-particle relaxivity in $mM^{-1}s^{-1}$ of at least about one or more of about: 100,000, 125,000, 150,000, 165,000, 180,000, 190,000, and 200,000. Detecting the liposomal formulation may include detecting using magnetic resonance imaging, for example, in a magnetic field range of between about 1 T to about 3.5 T, or about 1.5 to about 3 T. The nonradioactive MRI contrast enhancing agent may include gadolinium. For example, the nonradioactive MRI contrast enhancing agent may include (diethylenetriaminepenaacetic acid)-bis(stearylamide), gadolinium salt (Gd-DTPA-BSA). Gadolinium paramagnetic chelates such as GdDTPA, GdDOTA, GdHPDO3A, GdDTPA-BMA, and GdDTPA-BSA are known MRI contrast agents. See U.S. Pat. No. 5,676,928 issued to Klaveness et al., which is incorporated by reference herein in its entirety.

In some embodiments, the membrane may include one or more stabilizing excipients. The one or more stabilizing excipients may include a sterol, e.g., cholesterol, or a fatty acid.

In several embodiments, the membrane may include a first phospholipid. The membrane may include a second phospholipid. The second phospholipid may be derivatized with a hydrophilic polymer that may include, for example, a hydrophilic poly(alkylene oxide). The hydrophilic poly(alkylene oxide) may include between about 10 and about 100 repeat units. The hydrophilic poly(alkylene oxide) may include, for example, poly(ethylene oxide), poly (propylene oxide) and the like. As used herein, the phospholipid moieties in each of the "first phospholipid," the "second phospholipid," and in the phospholipid-polymer-aromatic conjugate are selected independently.

In various embodiments, the membrane of the liposome composition may include: DPPC; cholesterol; diethylenetriamine pentaacetic acid)-bis(stearylamide), gadolinium salt; and 1,2-distearoyl-sn-glycero-3-phosphoethanolamine-N-[methoxy (polyethylene glycol)-2000] ("DSPE-mPEG-2000"; CAS No. 147867-65-0). The phospholipid-polymer-aromatic conjugate may be represented by one of the following structural formula:

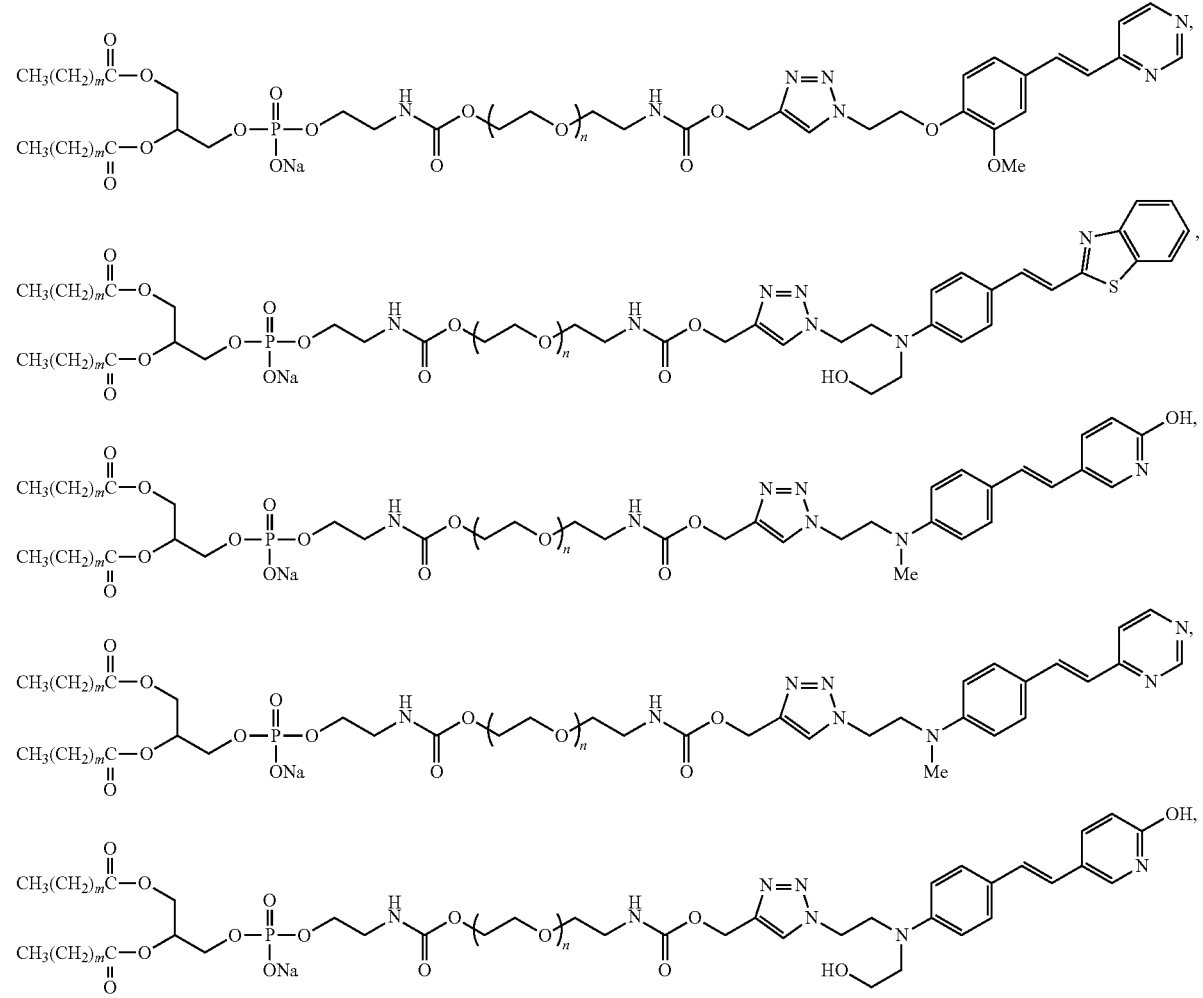

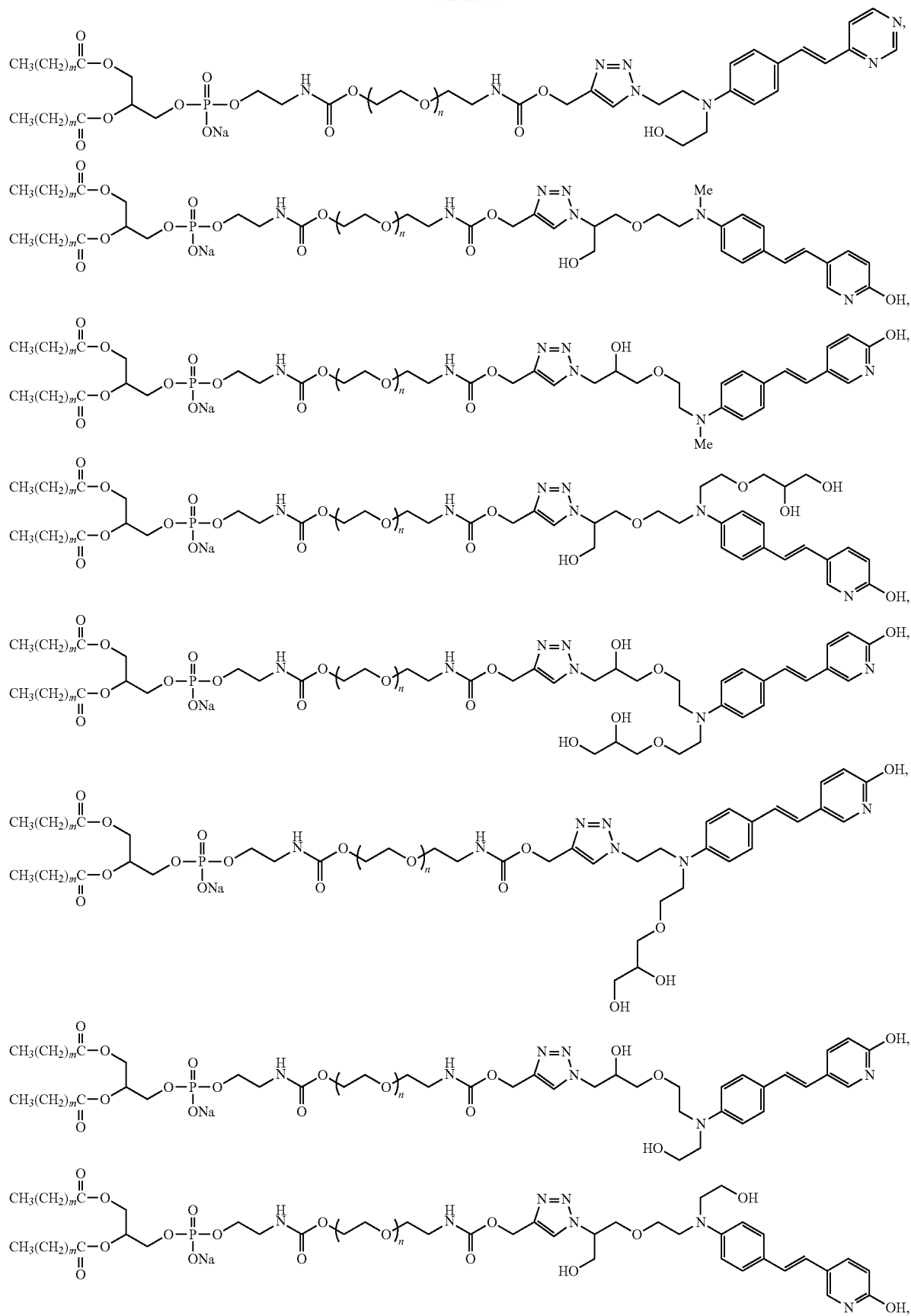

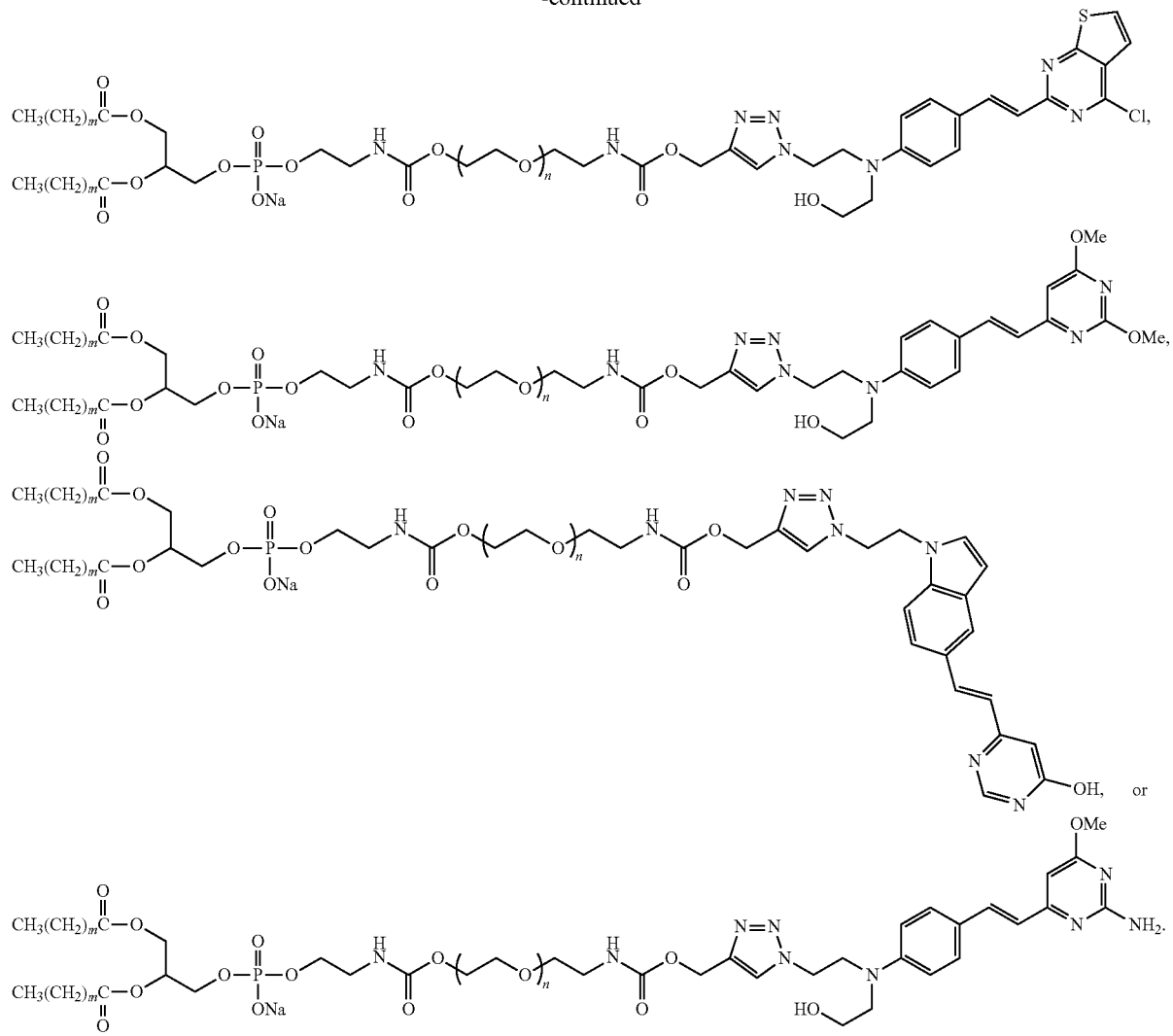

The variable n may be any integer from about 10 to about 100, for example, about 60 to about 100, about 70 to about 90, about 75 to about 85, or about 77. The variable m may be one of: 12, 13, 14, 15, 16, 17, or 18. For example, n may be 77 and m may be 14. In another example, n may be 77 and m may be 16.

In various embodiments, one or more alternative amyloid ligands in addition to the aromatic moieties and compounds described herein may include, for example, Congo red and its derivatives, Thioflavin T and its derivatives, and Chrysamine G and its derivatives. Such alternative amyloid ligands may be conjugated with a hydrophilic polymer, e.g., PEG. (having, e.g., a molecular weight ranging from 500-10,000 Da) and the like, and a lipid, e.g., DPPC, DSPE, DSPC, DPPE, and the like, to form a lipid-hydrophilic polymer-amyloid ligand conjugate. For example, the lipid-polymer-amyloid ligand conjugate may be incorporated into the liposomal composition described herein.

In various embodiments, a method for imaging amyloid deposits in a subject is provided. The method may include introducing into the subject a detectable quantity of a liposomal composition. The method may include allowing sufficient time for the liposomal composition to be associated with one or more amyloid deposits. The method may include detecting the liposomal composition associated with the one or more amyloid deposits. The liposomal composition of the method may include a membrane. A nonradioactive magnetic resonance imaging (MRI) contrast enhancing agent may be at least one of encapsulated by or bound to the membrane. The membrane may include a phospholipid-polymer-aromatic conjugate. The aromatic moiety in the phospholipid-polymer-aromatic conjugate may be represented by Structural Formula I:

or a pharmaceutically acceptable salt thereof. In the aromatic moiety in the phospholipid-polymer-aromatic conjugate represented by Structural Formula I, X may be —$R^2$—O— or —$R^2$—N($R^3$)—. $R^1$ may be $C_2$-$C_6$ alkyl or alkenyl. $R^2$ may be a linking group including 1 to 6 carbon atoms. $R^2$ may include one of: alkylene or alkoxyalkylene. $R^3$ may be hydrogen, $C_1$-$C_6$ alkyl, or $C_1$-$C_6$ alkoxyalkyl. Ar may be a monocyclic or polycyclic group. Ar may include at least one aromatic or heteroaromatic ring. Het may be a monocyclic or polycyclic group. Het may include at least one heteroaromatic ring. The aromatic moiety in the phospholipid-polymer-aromatic conjugate represented by Formula I may further be substituted. For example, $R^2$ may be substituted with zero, one or more of: hydroxyl, alkyl, $C_1$-$C_6$ alkyl, and $C_1$-$C_6$ hydroxyalkyl. Ar, Het, $R^1$, and $R^3$ other than hydrogen may be independently substituted with zero, one or more of halogen; —OH; alkyl, aryl, —O-aryl or —(O-alkylene)$_{1-6}$ optionally substituted with —OH or halogen; —NH$_2$; —NH-alkyl; —N-dialkyl; carboxyl; sulfonyl; carbamoyl; and glycosyl.

In various embodiments, the liposomal composition and the phospholipid-polymer-aromatic conjugate used in the method may include any values described herein for the liposomal composition and the phospholipid-polymer-aromatic conjugate.

In some embodiments, the detecting may include detecting using magnetic resonance imaging. In another example, the detecting may include detecting by fluorescence imaging (FI). The detecting may include detecting by SPECT imaging and/or PET imaging, and the non-radioactive contrast enhancing agent may be replaced with a radioactive contrast enhancing agent. The radioactive contrast enhancing agent may include, for example, those agents deemed appropriate for use with SPECT imaging and/or PET imaging in the National Institute of Health's Molecular Imaging and Contrast Agent Database ("MICAD"). Any other suitable type of imaging methodology known by those skilled in the art is contemplated, including, but not limited to, PET imaging.

In various embodiments, the method may include diagnosing the patient with Alzheimer's disease according to detecting the liposomal composition associated with the one or more amyloid deposits.

In some embodiments, the method may include identifying the patient as potentially having Alzheimer's disease according to detecting the liposomal composition associated with the one or more amyloid deposits. The method may include subjecting the patient to an analysis for tau neurofibrillary tangles, for example, a PET analysis for tau neurofibrillary tangles. The method may include, upon determining the presence of tau neurofibrillary tangles in conjunction with detecting the liposomal composition associated with the one or more amyloid deposits, diagnosing the patent with Alzheimer's disease.

In various embodiments, the liposomal composition and the phospholipid-polymer-aromatic conjugate used in the method may include any values described herein for the liposomal composition and the phospholipid-polymer-aromatic conjugate.

In various embodiments, a kit for imaging amyloid deposits in a subject is provided. The kit may include any liposomal composition described herein. The instructions may direct a user to introduce into the subject a detectable quantity of the liposomal composition. The instructions may direct the user to allow sufficient time for the liposomal composition to be associated with one or more amyloid deposits. The instructions may direct the user to detect the liposomal composition associated with the one or more amyloid deposits. The liposomal composition of the kit may include a membrane. A nonradioactive magnetic resonance imaging (MRI) contrast enhancing agent may be at least one of encapsulated by or bound to the membrane. The membrane may include a phospholipid-polymer-aromatic conjugate. The aromatic moiety in the phospholipid-polymer-aromatic conjugate may be represented by Structural Formula I:

—X—Ar—$R^1$-Het  (I)

or a pharmaceutically acceptable salt thereof. In the aromatic moiety in the phospholipid-polymer-aromatic conjugate represented by Structural Formula I, X may be —$R^2$—O— or —$R^2$—N($R^3$)—. $R^1$ may be $C_2$-$C_6$ alkyl or alkenyl. $R^2$ may be a linking group including 1 to 6 carbon atom. $R^2$ may include one of: alkylene or alkoxyalkylene. $R^3$ may be hydrogen, $C_1$-$C_6$ alkyl, or $C_1$-$C_6$ alkoxyalkyl. Ar may be a monocyclic or polycyclic group. Ar may include at least one aromatic or heteroaromatic ring. Het may be a monocyclic or polycyclic group. Het may include at least one heteroaromatic ring. The aromatic moiety in the phospholipid-polymer-aromatic conjugate represented by Formula I may further be substituted. For example, $R^2$ may be substituted with zero, one or more of: hydroxyl, $C_1$-$C_6$ alkyl, and $C_1$-$C_6$ hydroxyalkyl. Ar, Het, $R^1$, and $R^3$ other than hydrogen may be independently substituted with zero, one or more of: halogen; —OH; alkyl, —O-alkyl, aryl, —O-aryl or —(O-alkylene)$_{1-6}$ optionally substituted with —OH or halogen; —NH$_2$; —NH-alkyl; —N-dialkyl; carboxyl; sulfonyl; carbamoyl; and glycosyl.

In various embodiments, the instructions may direct a user to carry out any of the method steps described herein. For example, the instructions array direct a user to diagnose the patient with Alzheimer's disease according to detecting the liposomal composition associated with the one or more amyloid deposits.

In some embodiments, the instructions may direct a user to identify the patient as potentially having Alzheimer's disease according to detecting the liposomal composition associated with the one or more amyloid deposits. The instructions may direct, the user to subject the patient to an analysis for tau neurofibrillary tangles, for example, a PET analysis for tau neurofibrillary tangles. The instructions may direct the user to diagnose the patent with Alzheimer's disease upon determining the presence of tau neurofibrillary tangles in conjunction with detecting the liposomal composition associated with the one or more amyloid deposits.

EXAMPLES

Certain embodiments are described below in the form of examples. It is impossible to depict every potential application of the invention. Thus, while the embodiments are described in considerable detail, it is not the intention to restrict or in any way thrift the scope of the appended claims to such detail, or to any particular embodiment.

General: All reagents were obtained from Sigma-Aldrich (St. Louis, Mo.) and used without further purification. Proton nuclear magnetic resonances ($^1$H NMR) spectra were recorded at 600 MHz on a Bruker 600 NMR spectrometer (Bruker, Billerica, Mass.). Carbon nuclear magnetic resonances ($^{13}$C NMR) spectra were recorded at 150 MHz on a Broker 600 NMR spectrometer. Chemical shifts are reported in parts per million (ppm) from an internal standard acetone (2.05 ppm), chloroform (7.26 ppm), or dimethylsulfoxide (2.50 ppm) for $^1$H NMR; and from an internal standard of either residual acetone (206.26 ppm), chloroform (77.00 ppm), or dimethylsulfoxide (39.52 ppm) for $^{13}$C NMR. NMR peak multiplicities are denoted as follows: s (singlet), d (doublet), t (triplet), q (quartet), bs (broad singlet), dd (doublet of doublet), tt (triplet of triplet), ddd (doublet of doublet of doublet), and m (multiples). Coupling constants (J) are given in hertz (Hz). High resolution mass spectra (HRMS) were obtained from The Ohio State University Mass Spectrometry and Proteomics Facility, Columbus Ohio; HRMS and matrix-assisted laser desorption/ionization (MALDI) spectra were also obtained from Mass Spectrometry Unit of the BioScience Research Collaborative at Rice University, Houston, Tex. Thin layer chromatography (TLC)

was performed on silica gel 60 F254 plates (EMD Chemical Inc., Gibbstown, N.J.) and components were visualized by ultraviolet light (254 nm) and/or phosphomolybdic acid, 20 wt % solution in ethanol, SiliFlash silica gel (230-400 mesh) was used for all column chromatography.

Figure 1B:
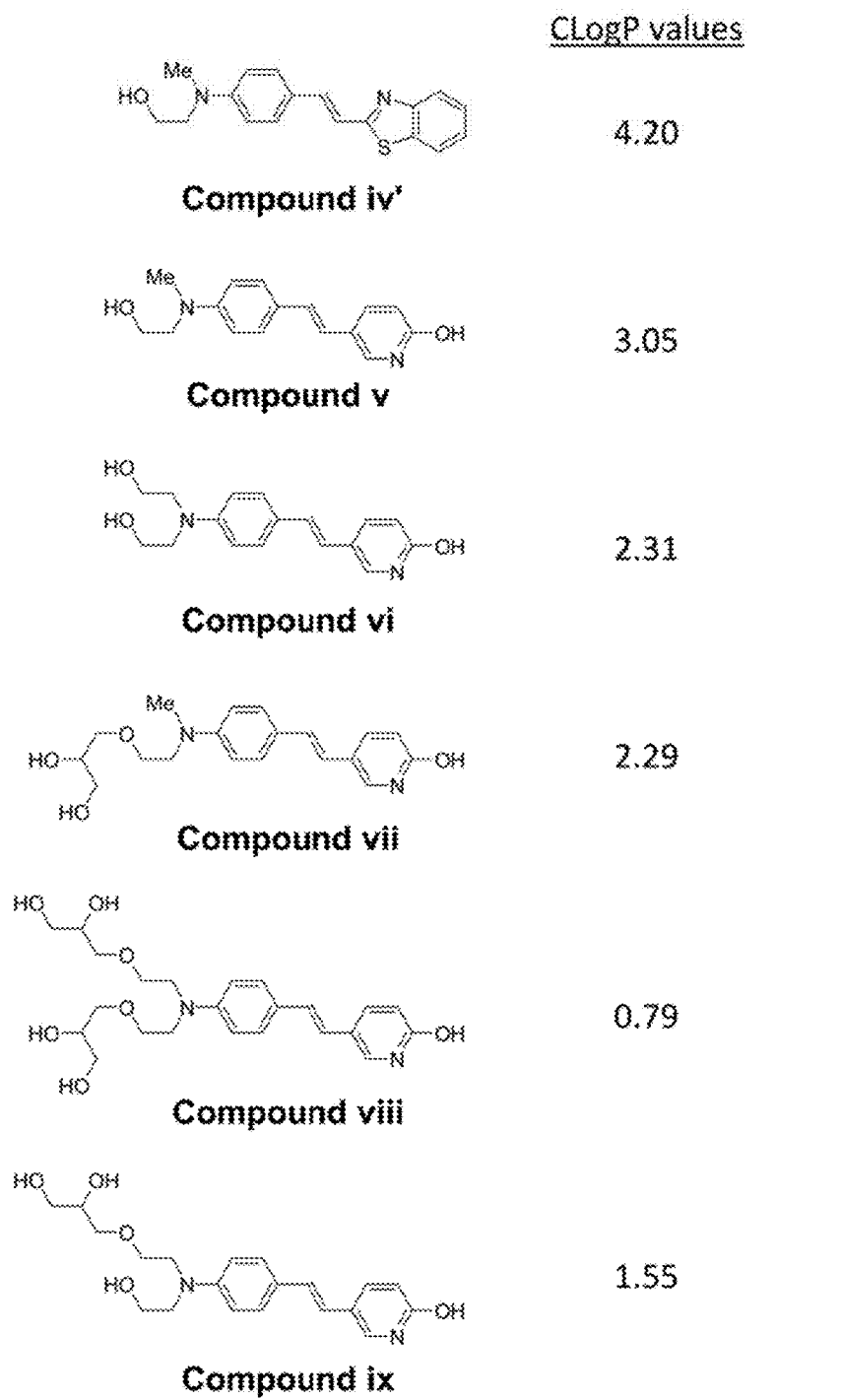
FIG. 1B is a table showing C Log P values and structures for various compounds.

The following methods ma be used or adapted to synthesize Compounds i-xiii as depicted in FIGS. 1A, 1B, and 1C.

Example 1A

Preparation of Compound i

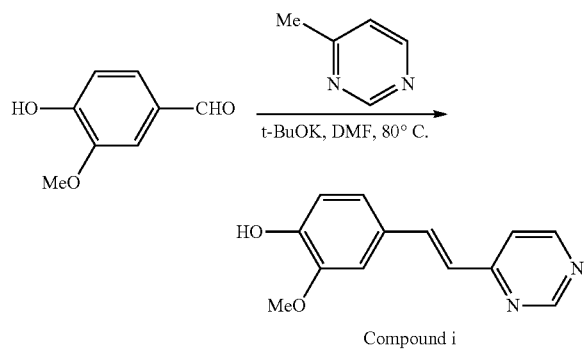

Compound i was prepared by reacting 4-hydroxy-3-methoxybenzaldehyde (466 mg, 3.06 mmol) with 4-methylpyrimidine (140 μL, 1.53 mmol) and potassium tert-butoxide (687 mg, 6.12 mmol) in N,N-dimethyl formamide (24 mL). The reaction mixture was filtered through celite and Compound i was isolated by silica gel chromatography using an ethyl acetate/methanol/hexane solvent mixture. (E)-2-methoxy-4-[2-(pyrimidin-4-yl)vinyl]phenol (Compound i): $^1$H NMR (DMSO-d6, 600 MHz) δ 9.51 (bs, OH), 9.08 (d, J=1.2 Hz, 1H), 8.70 (d, J=5.4 Hz, 1H), 7.86 (d, J=16.2 Hz, 1H), 7.54 (dd, J=5.4, 1.2 Hz, 1H) 7.35 (d, J=1.5, Hz, 1H), 7.15 (dd, J=8.0, 1.5 Hz, 1H), 7.12 (d, J=16.2 Hz, 1H), 6.83 (d, J=8.0 Hz, 1H), 3.89 (s, 3H); $^{13}$C NMR (DMSO-d6, 150 MHz) δ 162.16, 158.38, 157.39, 148.46, 147.93, 137.25, 126.98, 122.53, 122.21, 118.48, 115.60, 110.71, 55.62; FIRMS clcd for C13H12N2O2+m/z (M+H)+ 229.0972, found 229.0981.

Prophetic Example 1B

Preparation of Alkoxylated Derivatives

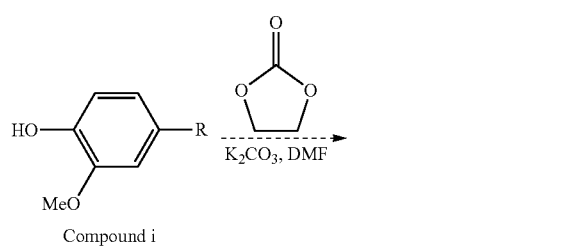

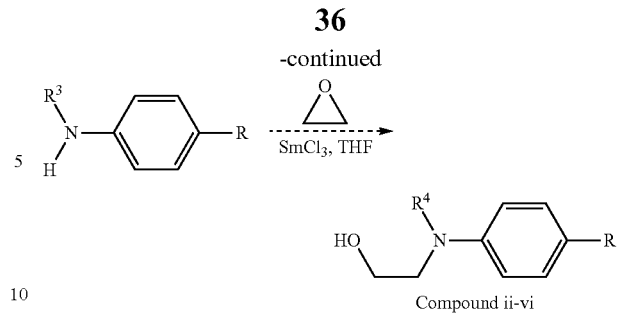

Various O- and N-hydroxyethyl compounds and derivatives may be prepared as follows. For example, Compound i may be treated with ethylene carbonate to produce the corresponding all oxylated derivative. Further, for example, Compounds ii, iv, and v may be prepared by reacting the corresponding aniline derivative with ethylene oxide, where $R^3=R^4$=alkyl, e.g., methyl. The reaction may include the addition of an acid, or Lewis acid. The reaction may include reaction temperatures above ambient temperature. The preparation of dialkoxylated compounds, such as Compounds iii and vi may include 2 equiv of epoxide, where, e.g., $R^3$=H and $R^4$ may be a second hydroxyethyl group ($CH_2CH_2OH$). Alternatively, either O- or N-hydroxyethyl compounds or derivatives may be prepared by an alkylation with a β-hydroxyhalide, such as 2-bromoethanol (not illustrated). The O- and N-hydroxyethyl compounds may be used as substrates for the corresponding glycerol derivatives as described in Example 7.

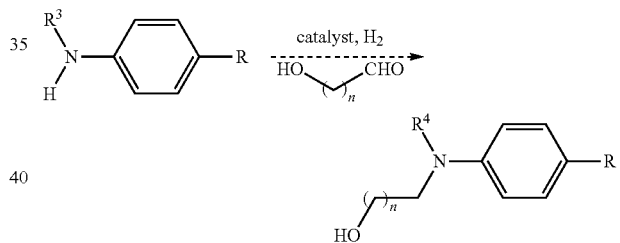

N-hydroxyethyl Compounds may alternatively be prepared by reductive amination with 2-hydroxyethanal (glycolaldehyde) in the presence of hydrogen and a catalyst, such as Pd/C. Homologated derivatives may readily be prepared under similar conditions with an appropriate hydroxyaldehyde such as 3-hydroxypropanal (n=2), 4-hydroxylbutanal (n=3), 5-hydroxypentanal (n=4), or 6-hydroxyhexanal (n=5).

Example 2

Preparation of Compound ii

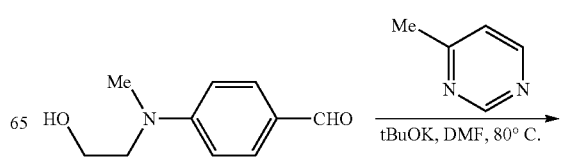

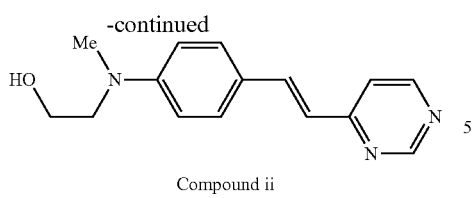

Compound ii

NMR (DMSO-d6, 150 MHz) δ 165.23, 159.17, 157.76, 149.72, 139.99, 130.84, 125.87, 121.64, 119.42, 113.66, 51.36, 50.08; HRMS clcd for C16H19N3O2+m/z (M+H)+ 286.1550, found 286.1546.

In one example, Compound ii was prepared by reacting N-methyl-N-(2-hydroxyethyl)-4-aminobenzaldehyde (200 mg, 1.12 mmol) with 4-methylprimidine (112 μL, 1.23 mmol) and potassium tert-butoxide (376 mg, 3.35 mmol) in N,N-dimethyl formamide (10 mL) for 4 hours at 80° C. The resulting mixture was cooled to ambient temperature, filtered through celite and concentrated. Silica gel chromatography using an ethyl acetate/methanol/hexane solvent gradient yielded Compound ii (E-isomer) (184 mg, 0.72 mmol, 64%), Z-isomer (18 mg, 0.07 mmol, 6%), and E/Z-isomer mixture (39 mg, 0.15 mmol, 14%). (E)-2-{methyl[4-(2-(pyrimidin-4-yl)vinyl)phenyl]amino}ethanol (Compound ii): ¹H NMR (CDCl3, 600 MHz) δ 8.91 (d, J=1.2 Hz, 1H), 8.45 (d, J=5.4 Hz, 1H), 7.70 (d, J=15.6 Hz, 1H), 7.41 (d, J=6.6 Hz, 2H), 7.26 (dd, J=6.6, 1.2 Hz, 1H), 6.75 (d, J=15.6 Hz, 1H), 6.67 (d, 6.6 Hz, 2H), 3.69 (t, J=6.6 Hz, 2H), 3.46 (t, J=6.6 Hz, 2H), 3.98 (s, 3H); ¹³C NMR (DMSO-d6, 150 MHz) δ 163.80, 157.60, 155.80, 150.59, 139.19, 129.54, 123.21, 119.48, 117.83, 115.13, 111.91, 59.13, 54.35, 38.82; HRMS clod for C15H17N3O+m/z (M+H)+ 256.1444, found 256.1372.

Example 3

Preparation of Compound iii

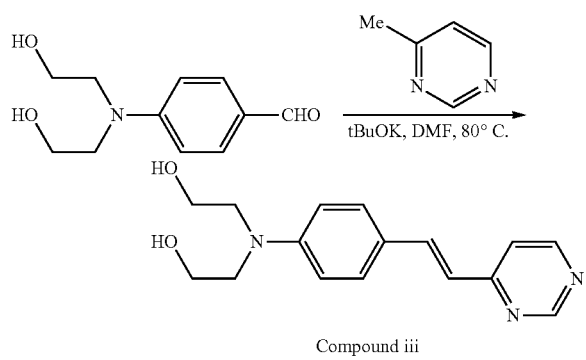

Compound iii

In one example, Compound iii was prepared by reacting 4-(bis(hydroxyethyl)amino)benzaldehyde (234 mg, 1.12 mmol) with of -4-methylpyrimidine (112 μL, 1.23 mmol) and of potassium tert-butoxide (376 mg, 3.35 mmol) in N,N-dimethyl formamide (10 mL) for 12 hours at 80° C. The resulting mixture was cooled to ambient temperature and filtered through celite and concentrated. Compound iii was isolated as the major component of a mixture by silica gel chromatography using an ethyl acetate/methanol/hexane solvent system, (E)-2,2'-{[4-(2-(pyrimidin-4-yl)vinyl)phenyl]azanediyl}diethanol (Compound iii): ¹H NMR (MeOD, 600 MHz) δ 9.02 (d, J=1.2 Hz, 1H), 8.61 (d, J=5.4 Hz, 1H), 7.88 (d, J=15.6 Hz, 1H), 7.58 (d J==8.7 Hz, 2H), 7.53 (dd, J=6.0, 1.2 Hz, 1H), 6.98 (d, J=15.6 Hz, 1H), 6.88 (d, J=8.7 Hz, 2H), 3.71 (t, J=6.0 Hz, 4H), 3.57 (t. J=6.0 Hz, 4H); ¹³C

Example 4

Preparation of Azides: Compound A

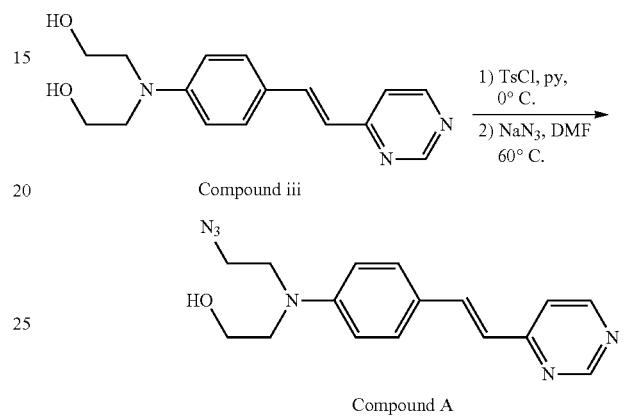

Compound A

Compound A was prepared by adding 4-toluenesulfonyl chloride (301 mg, 1.58 mmol) to a solution of Compound iii (300 mg, 1.05 mmol) in pyridine (10 mL) at 0° C. and the mixture was allowed to warm to room temperature overnight. The pyridine was removed under reduced pressure and N,N-dimethyl formamide (15 mL) was added to the crude tosylate residue. Sodium azide (410 mg, 6.31 mmol) was added to the solution and the resulting mixture was heated at 60° C. overnight. The N,N-dimethyl formamide solvent was removed under reduced pressure and the resulting slurry was diluted with ethyl acetate and washed brine (15 mL). The aqueous layer was back extracted three times with ethyl acetate. The combined organic layers were dried over anhydrous MgSO4, filtered, and concentrated. Compound A (1.22 mg, 0.40 mmol, 38%) and the undesired di-azido product (1.23 mg, 037 mmol, 35%) were isolated by silica gel chromatography using an ethyl acetate/methanol/hexane (9.5:9.5:1) solvent mixture. The procedures described in Examples 4A and 4B nay be applied to other hydroxy alkyl compounds such as Compounds ii, iv, v, or vi, to produce the corresponding azides.

Example 5

Preparation of Compound iv

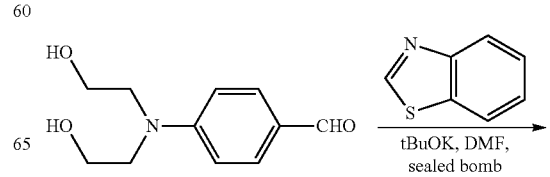

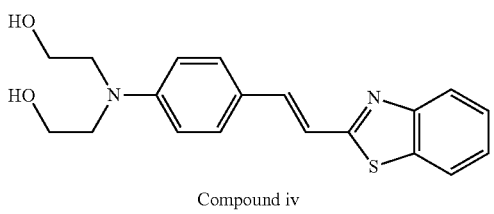

Compound iv

In one example, Compound iv was prepared by reacting 4-(bis(hydroxylethyl)amino)benzaldehyde (250 mg, 1.20 mmol) with benzothiazole (178 mg, 1.32 mmol) and potassium tert-butoxide (404 mg, 3.6 mmol) in N,N-dimethyl formamide (10 mL) for 5 hours in a sealed bomb. The reaction mixture was filtered through celite. Compound iv (89 mg, 0.26 mmol, 22%) was isolated by silica gel chromatography using an ethyl acetate/methanol/hexane solvent mixture.

Example 6

Preparation of Compounds v, vi, vii, viii, and ix

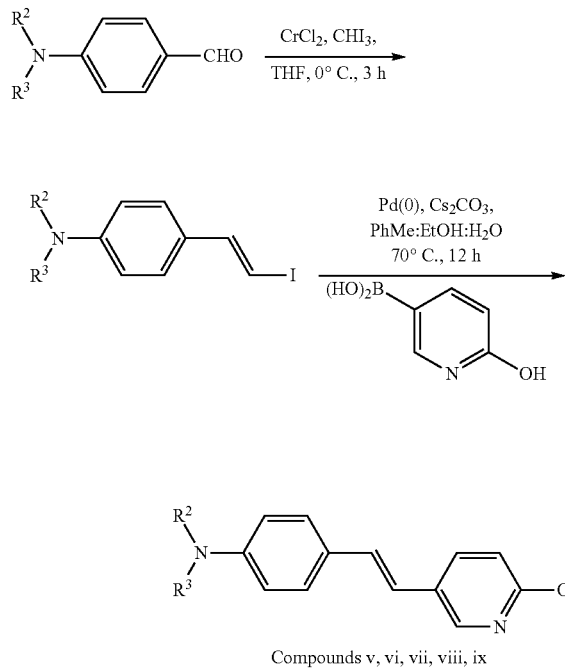

Compounds v, vi, vii, viii, ix

Compounds v, vi, vii, and viii may be readily prepared by first reacting the corresponding 4-aminobenzaldehyde under standard Takai conditions (e.g., triiodomethane (iodoform), chromium dichloride, in tetrahydrofuran for 3 h at 0° C.) to afford the corresponding vinyl iodide. Reaction of the vinyl iodide with (6-hydroxypyridin-3-yl)boronic acid under Suzuki conditions (e.g., Pd(0) catalyst, cesium carbonate, toluene/ethanol/water (4:4:1), 12 h, 70° C.), followed by silica gel chromatography using an ethyl acetate/methanol/hexane solvent mixture may produce Compounds v, vi, vii, and viii.

Prophetic Example 7

Syntheses of Glycerol Derivatives

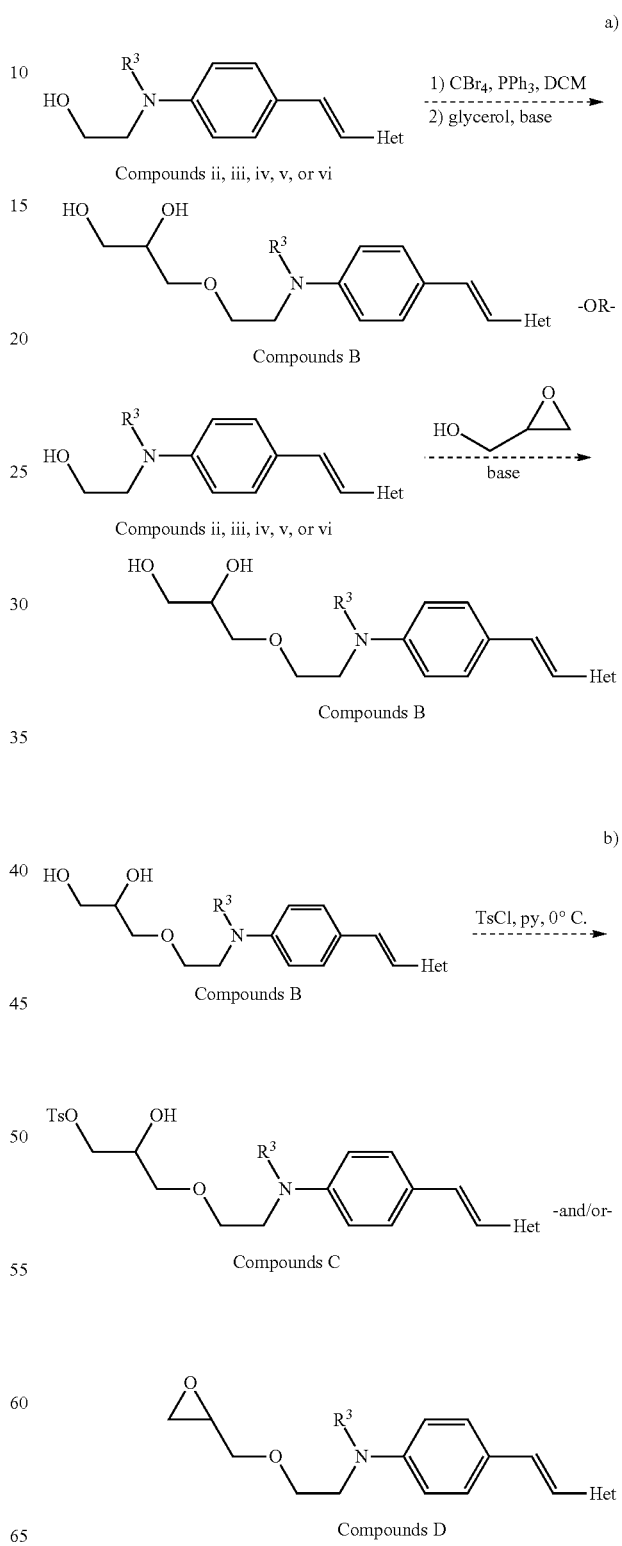

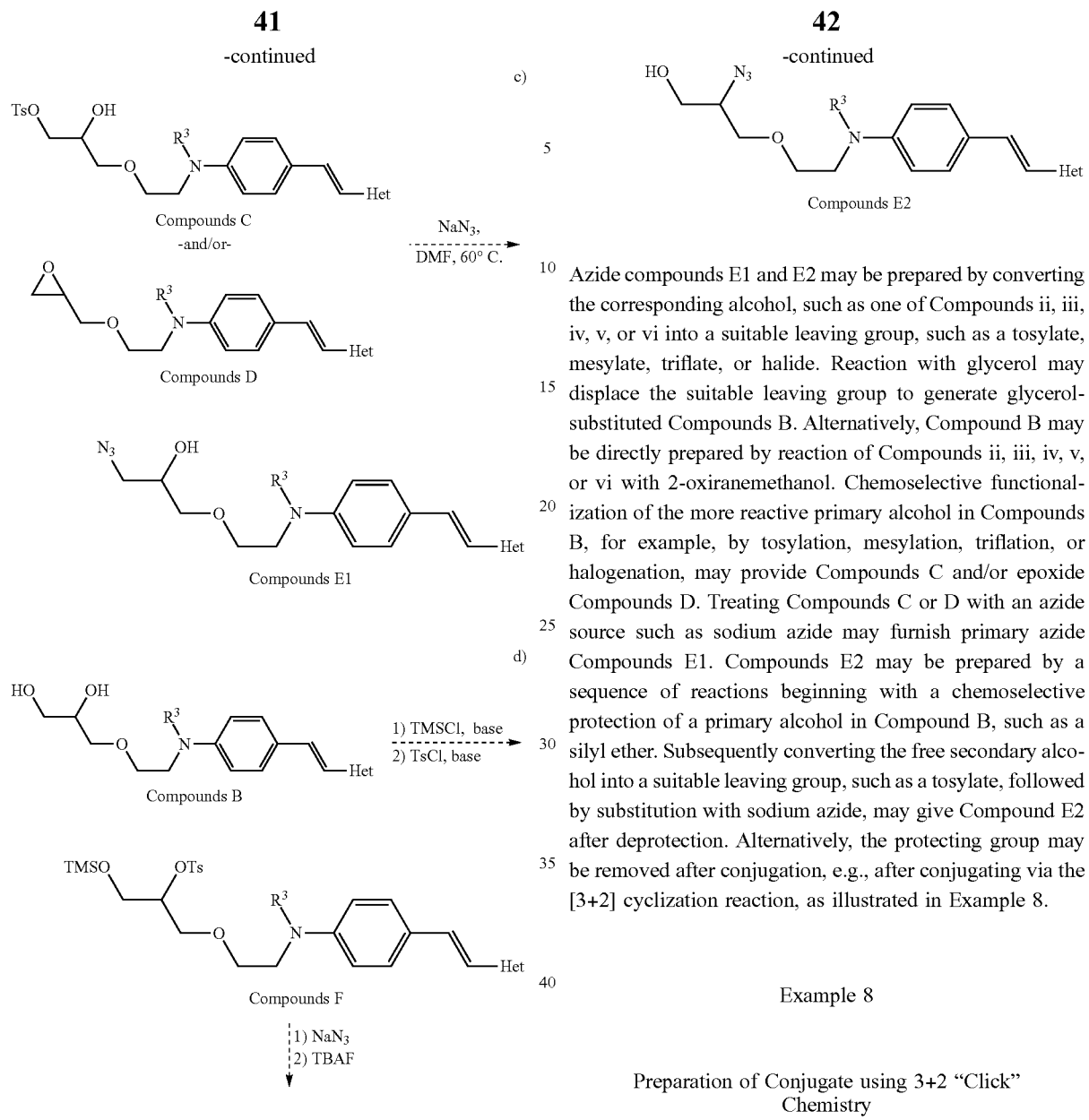

Azide compounds E1 and E2 may be prepared by converting the corresponding alcohol, such as one of Compounds ii, iii, iv, v, or vi into a suitable leaving group, such as a tosylate, mesylate, triflate, or halide. Reaction with glycerol may displace the suitable leaving group to generate glycerol-substituted Compounds B. Alternatively, Compound B may be directly prepared by reaction of Compounds ii, iii, iv, v, or vi with 2-oxiranemethanol. Chemoselective functionalization of the more reactive primary alcohol in Compounds B, for example, by tosylation, mesylation, triflation, or halogenation, may provide Compounds C and/or epoxide Compounds D. Treating Compounds C or D with an azide source such as sodium azide may furnish primary azide Compounds E1. Compounds E2 may be prepared by a sequence of reactions beginning with a chemoselective protection of a primary alcohol in Compound B, such as a silyl ether. Subsequently converting the free secondary alcohol into a suitable leaving group, such as a tosylate, followed by substitution with sodium azide, may give Compound E2 after deprotection. Alternatively, the protecting group may be removed after conjugation, e.g., after conjugating via the [3+2] cyclization reaction, as illustrated in Example 8.

Example 8

Preparation of Conjugate using 3+2 "Click" Chemistry

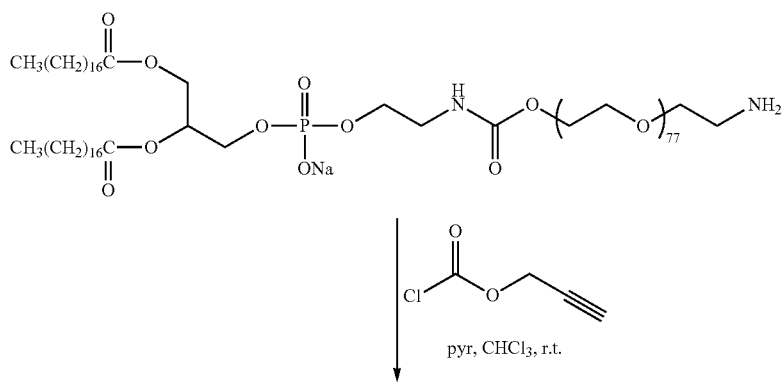

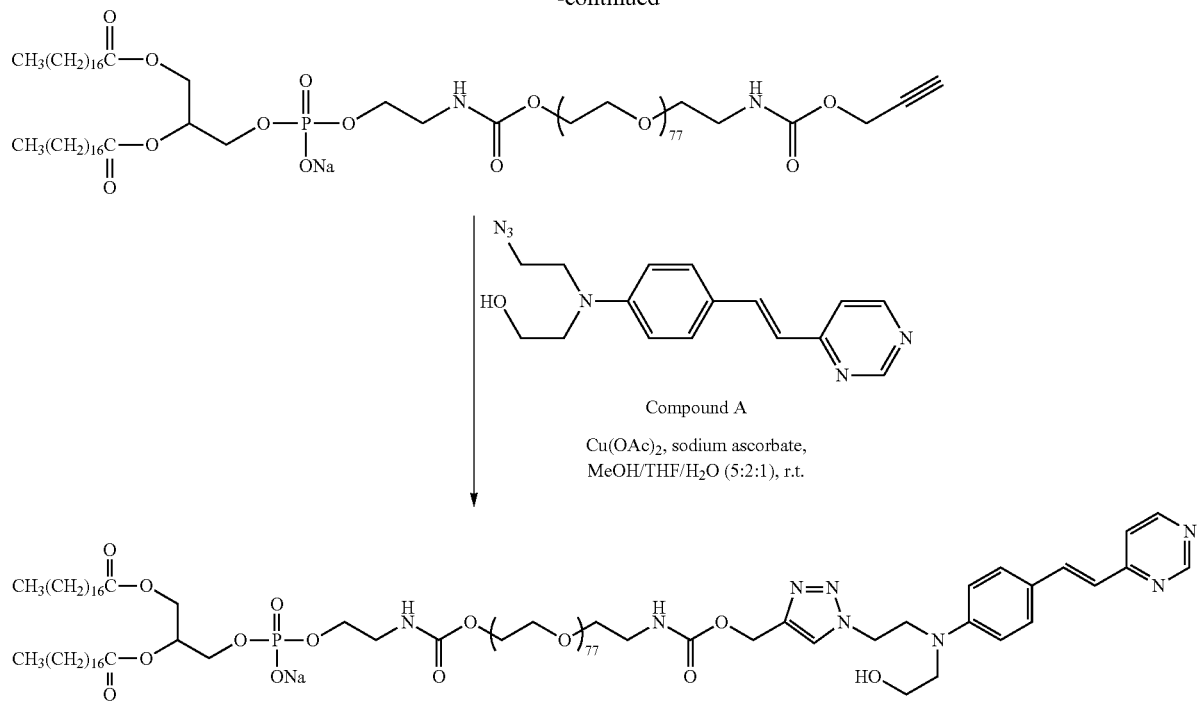

To a solution of DSPE-PEG$_{34K}$-NH$_2$ (1.0 g, 0.24 mmol), pyridine (5 mL, 62.1 mmol), and chloroform (5 mL) was added propargyl chloroformate (50 μL, 0.51 mmol). The resulting mixture was allowed to stir at ambient temperature overnight. The chloroform was removed under reduced pressure and the resulting residue was diluted with a 1:4 EtOH:H$_2$O solution (20 mL). The solution containing the crude carbamate was loaded into a 2000 MWCO dialysis bag and dialyzed against MES buffer (50 mM, 5 L) for 12 h and twice against water (5 L) for 12 h each. The solution was freeze-dried and the product (1.08 g, quant.) was obtained as a grey powder, the molecular weight of which was confirmed by MALDI.

Subsequently, the product (600 mg, 0.1.4 mmol) was added to Compound A (84 mg, 0.27 mmol) in methanol (10 mL) followed by the addition of THF (3 ML) and water (2 mL). Sodium ascorbate (27 mg, 0.14 mmol) and copper(II) acetate (2.7 mg. 0.014 mmol) were subsequently added and the resulting mixture was stirred at ambient temperature overnight. The solvents were removed under reduced pressure and the resulting residue was diluted with a 1:4 EtOH:H$_2$O solution (20 mL). The solution containing the crude triazole was loaded into a 2000 MWCO dialysis bag and dialyzed against MES buffer (50 mM, 5 L) and twice against water (5 L) for 12 h each. The solution was freeze-dried and the corresponding conjugate (565 mg, 0.12 mmol, 87%) was obtained as a colorless powder.

Example 9

Compounds are Hydrophilic Compared to Prior Compounds

FIGS. 1A, 1B, and 1C show C Log P values and structures fix various compounds in table form, including Compounds i-xiii, and known compounds MeXO4, SB-13 and Florbetapir. C Log P is the log of the partition coefficient for relative concentrations of the compound in octanol vs water as Log[Conc., octanol/Conc. Water]. Lower C Log P values correspond to greater hydrophilicity. While MeXO4 exhibits high affinity for amyloid plaques, we reasoned that the stilbene structures in SB-13 and the clinically used Florbetapir may provide sensitivity and specificity in binding. We further reasoned that benzothiazole or pyrimidyl moieties may generate analogues with lower C Log Ps and increased H-bonding potential, compared to known compounds. In addition, capping the nitrogen with hydroxyethyl group(s) could further increase the hydrophilicity and increase the potential for the ligand to remain floating in an aqueous medium external to the liposome instead of inserting into the lipid bilayer of the liposome. Accordingly, Compounds such as i-xiii were therefore devised with side-chain modifications generally expected to increase the hydrophilicity of the stilbene core to enhance a ligand's ability to be presented on a liposome surface without destabilizing the bilayer. Compounds i-xiii are each more hydrophilic than previous compound MeXO4 by several orders of magnitude. Without wishing to be bound by theory, it is believed that higher hydrophilicity may facilitate interaction and binding with amyloid beta fibrils, for example, by increasing the presence of the corresponding compounds in the hydrophilic environment outside of the liposomes in a configuration available for binding, by increasing binding interactions with amyloid beta fibrils, and the like.

Nonionic groups such as hydroxy and methoxy were selected to promote hydrophilicity without increasing the ionic character, out of concern that increased ionic character may reduce BBB permeability. Compounds i, ii, and iii had the three lowest C Log P values (1.56, 1.80, and 1.06, respectively). Spectrofluorometric testing showed that compounds ii and iii both had absorption and emission maxima at 404 nm and 550 nm, while compound i exhibited an absorption maximum at 346 nm without a visible emission maximum. Compounds ii and iii may be used for ease of detection by fluorescence and relatively low C Log P values.

Example 10

Synthesis of Aβ Fibrils

Aβ fibrils were synthesized according to the method of Klunk et al. Ann Neurol, 2004; 55: 306-19, the entire teachings of which are incorporated herein by reference. Briefly, Aβ$_{(1-40)}$ peptide (rPeptide, Bogart, Ga.) was dissolved in phospho-buffered saline, pH 7.4 to a final concentration of 433 μg/mL (100 μM). The solution was stirred using a magnetic stir bar at 700 rpm for 4 h at room temperature to drive the formation of fibrils. The stock solution was aliquoted and stored at −80° C. for future use. The stock solutions were stirred thoroughly before removing aliquots for binding assays to maintain a homogenous suspension of fibrils. The stock solutions were stirred thoroughly prior to removing aliquots for binding assays, to insure a homogenous suspension of fibrils.

Example 11

Binding Assays of Compound ii, Compound iii, and Conjugate of DSPE-PEG-Compound iii Binding assay: The binding affinity of the compounds or compound-labeled liposomes with the amyloid fibrils was measured by following methods. Ligand-labeled liposomes, ligand stock solutions, and Chrysamine G fix competition assays were diluted with 10 mM pH 7.4 to 500 nM. Fibril stock solution was mixed with a stock solution of the compound or the compound-labeled liposomes in a 200 μL reaction mix to give a final concentration of fibrils (20 μM) with test compounds varying from 0.0625-20 μM. The binding mixture was incubated at room temperature for 1 h. Subsequently, the incubated binding mixture was centrifuged for 20 min at 16,400 rpm to separate the fibrils. The fibril precipitate was washed twice with Tris-HCl. Fluorescence was then measured in a Filter Max F-5 multi-mode plate reader (Molecular Devices, Sunnyvale, Calif.), using excitation and emission wavelengths of 405 nm and 535 nm, respectively. Competitive binding assays used 20 μM of fibrils, 1.0 μM test compounds and varying amounts of the non-fluorescent competitor, Chrysamine G and incubated for 1 h.

FIG. 2 is a binding profile showing the binding of Compound ii to fibrils, plotted as relative fluorescence unit (RFU) versus concentration in μM. FIG. 3 is a binding profile showing the binding of Compound iii to fibrils, plotted as relative fluorescence unit (RFU) versus concentration in μM.

FIG. 4 is a binding profile showing the binding of MeXO4 (a previous compound) to fibrils, plotted as relative fluorescence unit (RFU) versus concentration in μM. The synthesis, conjugation, liposomal formulation, and binding using prior compound MeXO4 and other related compounds, which procedures may be used with the present compounds, conjugates and liposome compositions, are described in Annapragada, et al., U.S. patent application Ser. No. 13/441,816, the entire contents of which are incorporated herein by reference.

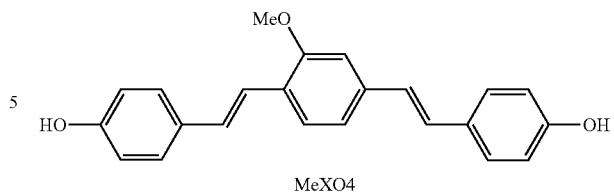

MeXO4

As shown in FIGS. 2-4, Compounds ii and iii showed much higher binding compared to prior compound MeXO4. For example, at a concentration of 1 μM, Compound ii bound at 35 m RFU, Compound iii bound at 400 k RFU, whereas previous compound MeXO4 bound at less than 100 k RFU.

Figure 5A:
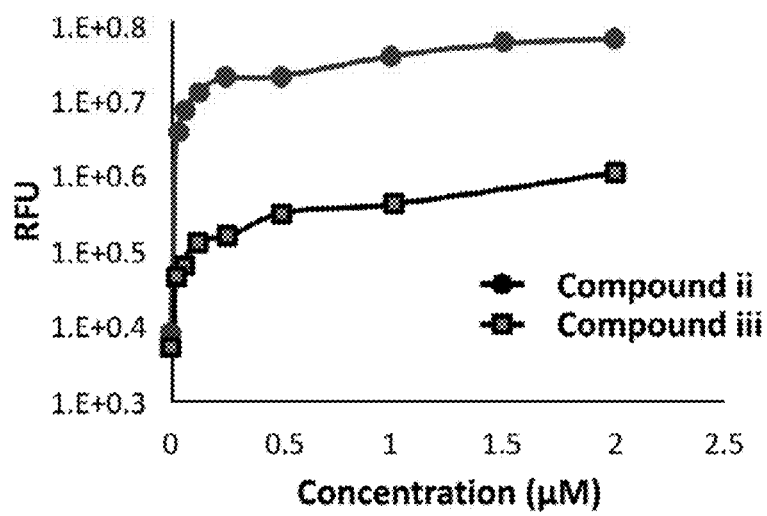
FIG. 5A is a graph showing that Compounds ii and iii bind to amyloid fibrils plotted as relative fluorescence unit (RFU) versus concentration in μM.
Figure 5B:
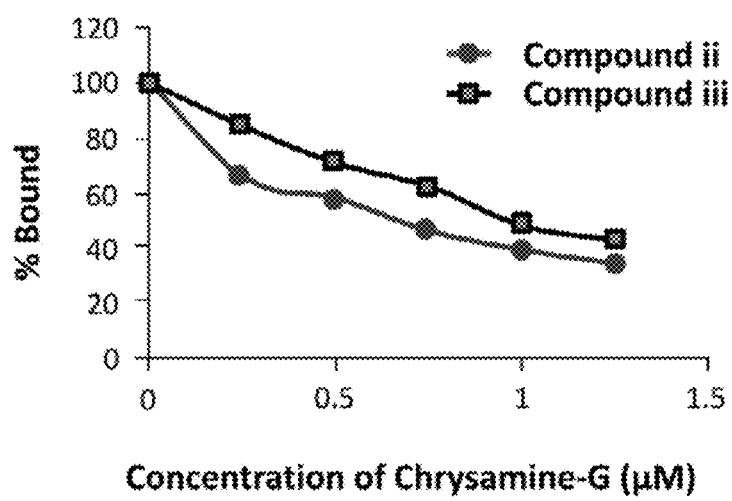
FIG. 5B is a competitive binding profile showing the binding of Compounds ii and iii, each bound stably to fibrils in suspension in competition with Chrysamine-G, plotted as % bound versus concentration of Chrysamine-G to μM.

FIGS. 5A-D illustrate aspects of the binding of Compounds ii and ii. FIG. 5A is a graph showing that Compounds ii and iii bind to amyloid fibrils plotted as relative fluorescence unit (RFU) versus concentration in μM, FIG. 5B is a competitive binding profile showing the binding of Compounds ii and iii, each bound stably to fibrils in suspension in competition with Chrysamine-G, plotted as % bound versus concentration of Chrysamine-G in μM, consistent with specificity to the Thioflavin binding site. This shows that Compounds ii and iii are indeed capable of binding to amyloid plaques, even being relatively hydrophilic.

Figure 5C:
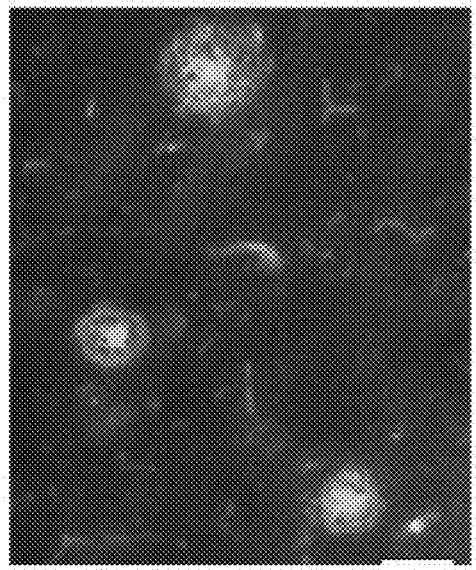
FIG. 5C is a fluorescent microscopy image showing that Compound iii specifically stains amyloid plaques in a section of human brain tissue from the frontal cortex of an AD autopsy case.

FIG. 5C is a fluorescent microscopy image showing that Compound iii specifically stains amyloid plaques in a section of human brain tissue from the frontal cortex of an AD autopsy case.

Figure 5D:
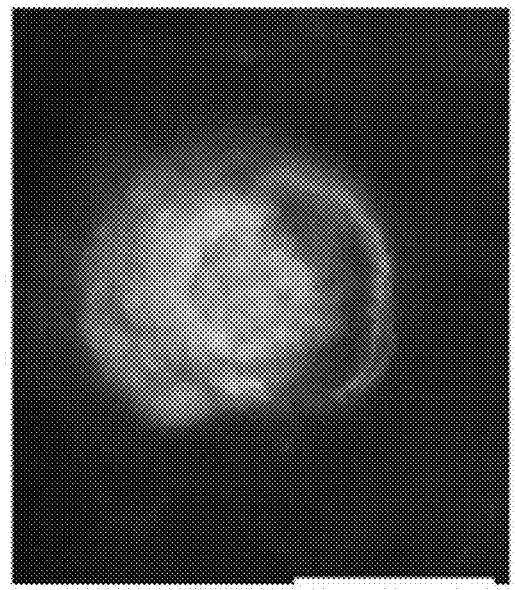
FIG. 5D is a fluorescent microscopy image showing that Compound iii labels cerebral amyloid angiopathy in aged dog brain tissue.

FIG. 5D is a fluorescent microscopy image showing that Compound iii labels cerebral amyloid angiopathy in aged dog brain tissue. Images were collected on an Olympus BX-51 epifluorescent microscope using the broadpass filter. Green labeling represents Compound iii while yellow represents nonspecific autofluorescence, Scale bars represent 50 μm in length.

Compound iii solutions in PBS were incubated with frontal cortex tissue obtained from autopsy of an 88 year old AD patient (the University of Kentucky Institutional Review Board approved the use of human tissue for the study; informed consent was obtained prior to autopsy) and a 12.3 year old canine. Both the human and canine tissues had Alzheimer's amyloid pathology confirmed from previous studies. 50 μm thick free-floating sections were mounted on slides and allowed to dry overnight. Slides were then washed in PBS (3×5 min) and incubated in Compound iii solution (1 mM) for 2 hours and then again washed 3×5 min in PBS, and coverslipped in Vectashield mounting medium with DAN (Vector Laboratories, Burlingame, Calif.). Sections were imaged on an Olympus BX-51 microscope with a broadpass filter (Olympus Corporation of the Americas, Center Valley, Pa.).

Figure 6:
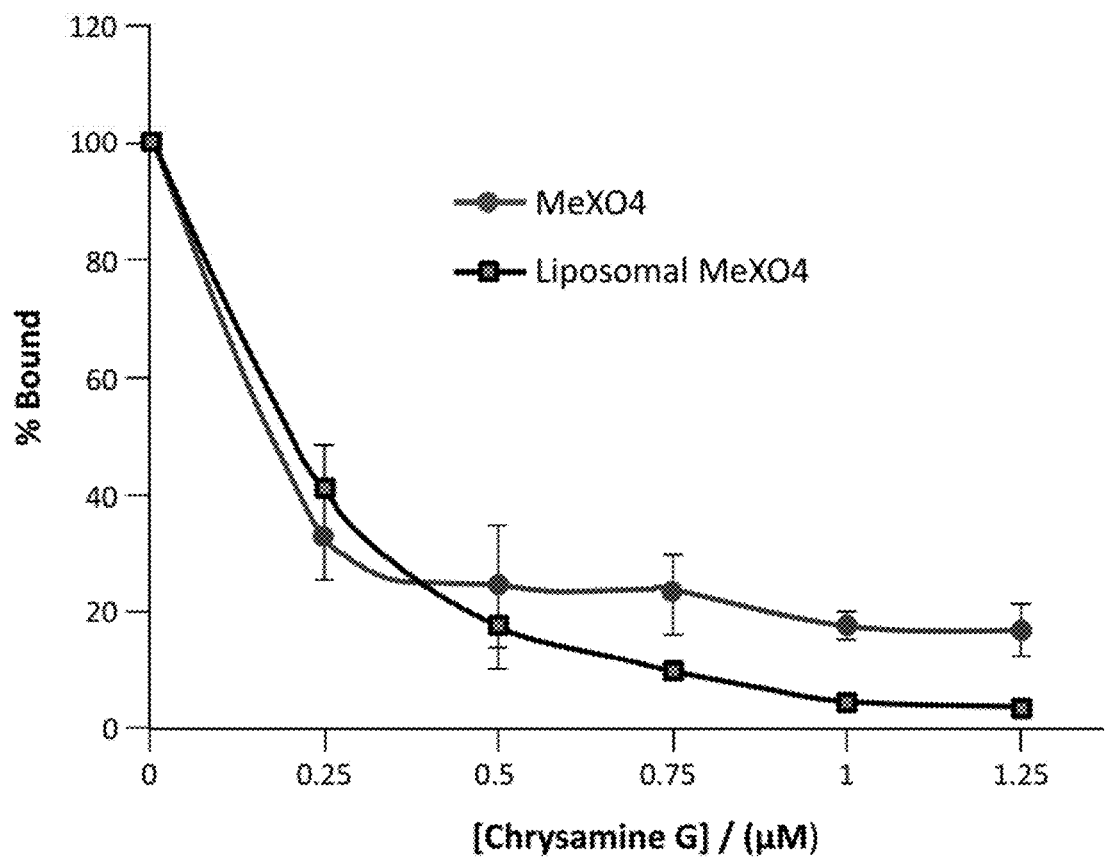
FIG. 6 is a competitive binding profile showing the binding of previous compound MeXO4 and liposomal MeXO4, each to fibrils in competition with Chrysamine-G, plotted as % bound versus concentration of Chrysamine-G in μM.

FIG. 6 is a competitive binding profile showing the binding of previous compound. MeXO4 and liposomal MeXO4, each to fibrils in competition with Chrysamine-G, plotted as % bound versus concentration of Chrysamine-G in μM. As shown in FIGS. 5A, 5B, and 6, Compounds ii and iii show much higher competitive binding versus Chrysamine-G compared to prior compound MeXO4 or liposomal MeXO4. For example, at a Chrysamine-G concentration of 1 μM, Compound ii was about 45% bound and Compound iii was about 55% bound. By contrast, prior compound MeXO4 was about 20% bound and liposomal MeXO4 was about 5% bound.

Figure 7A:
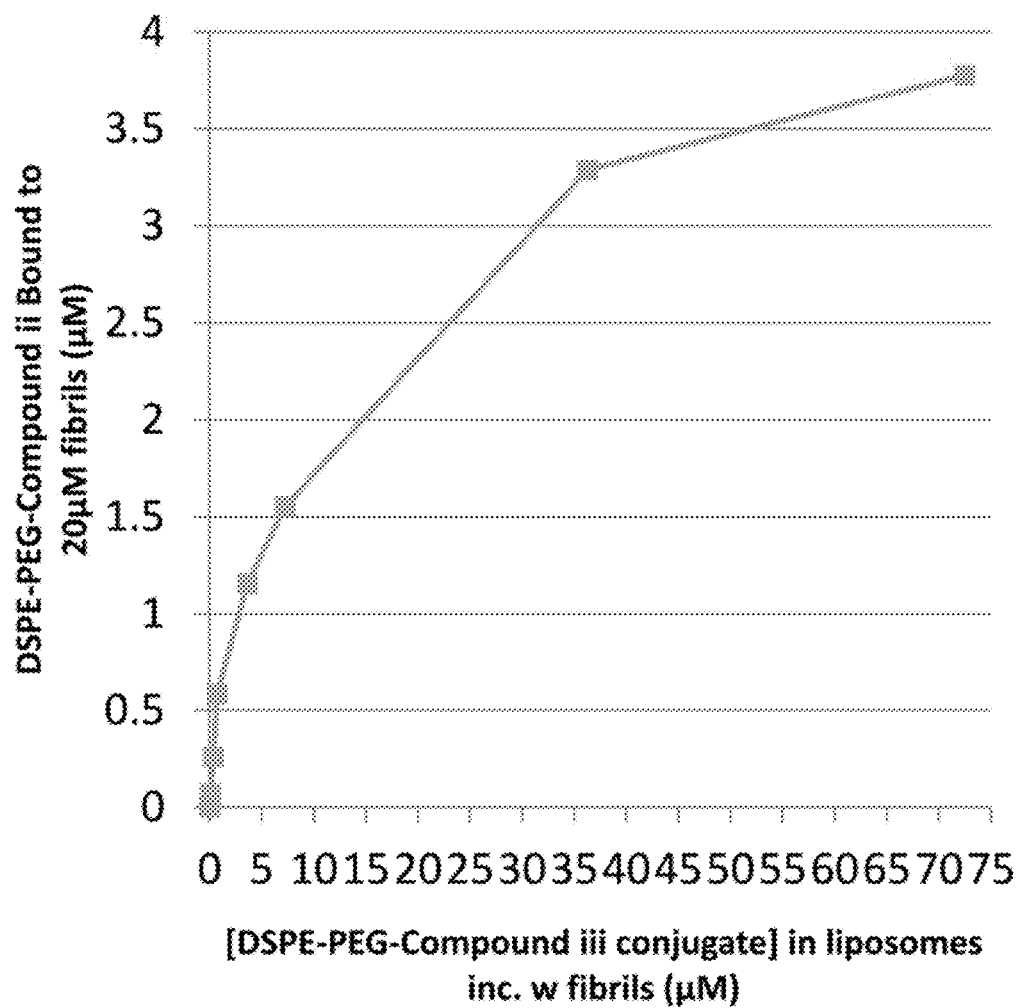
FIG. 7A is a graph of compound-labeled liposome binding profiles, showing the amount of the conjugate of DSPE-PEG-Compound iii bound to 20 μM fibrils, plotted versus the concentration of DSPE-PEG-Compound iii in the liposome compositions.

FIG. 7A is a graph of compound-labeled liposome binding profiles, showing the amount of the conjugate of DSPE-PEG-Compound iii bound to 20 µM fibrils, plotted versus the concentration of DSPE-PEG-Compound iii in the liposome compositions.

Figure 7B:
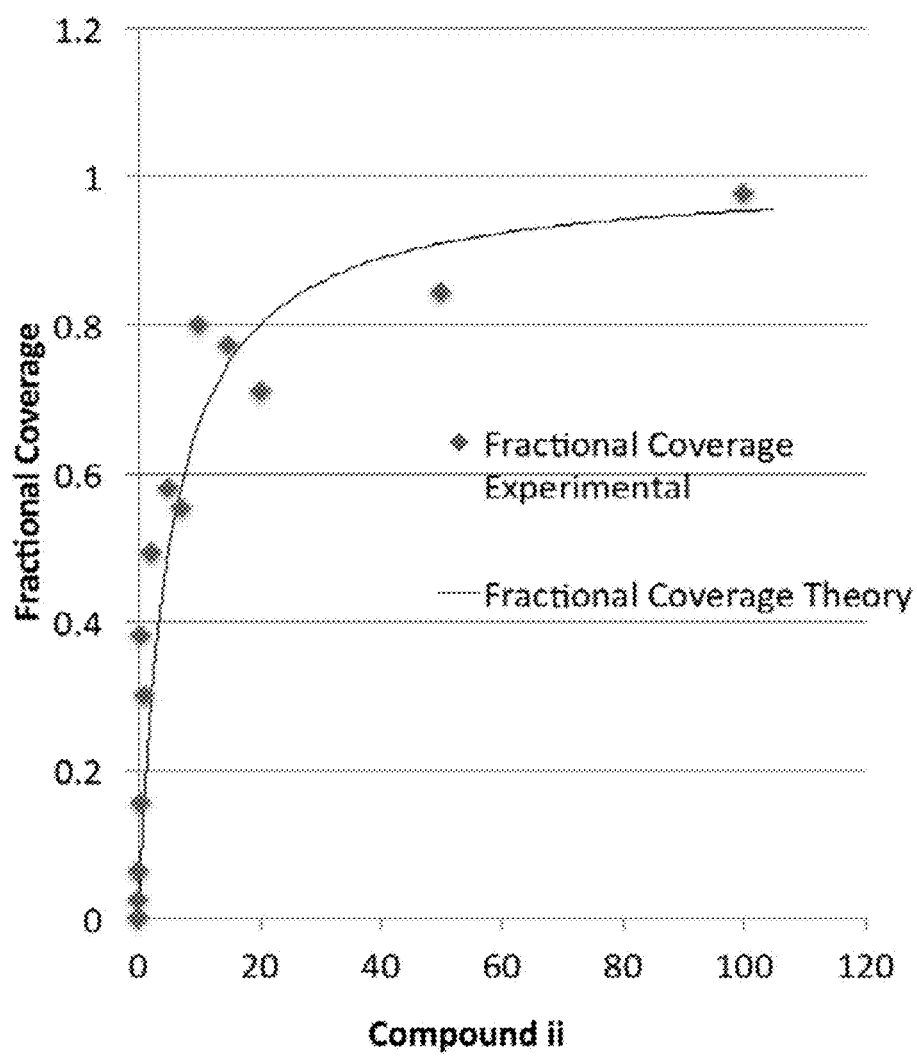
FIG. 7B is a graph showing fibril binding data and a calculated fit for estimation of the binding constant for Compound ii to fibrils at $K_d$=5.0 μM.
Figure 7C:
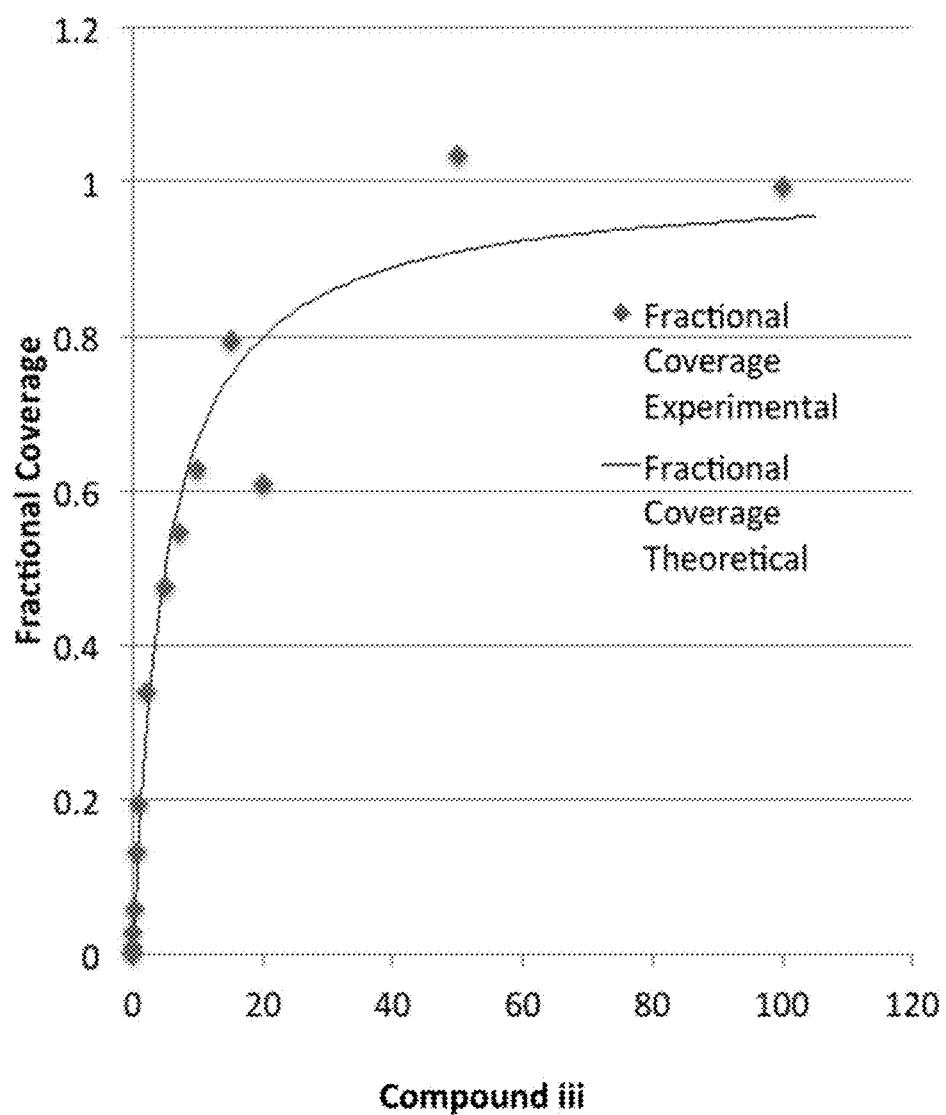
FIG. 7C is a graph showing fibril binding data and a calculated fit for estimation of the binding constant for Compound iii to fibrils at $K_d$=5.0 μM.
Figure 7D:
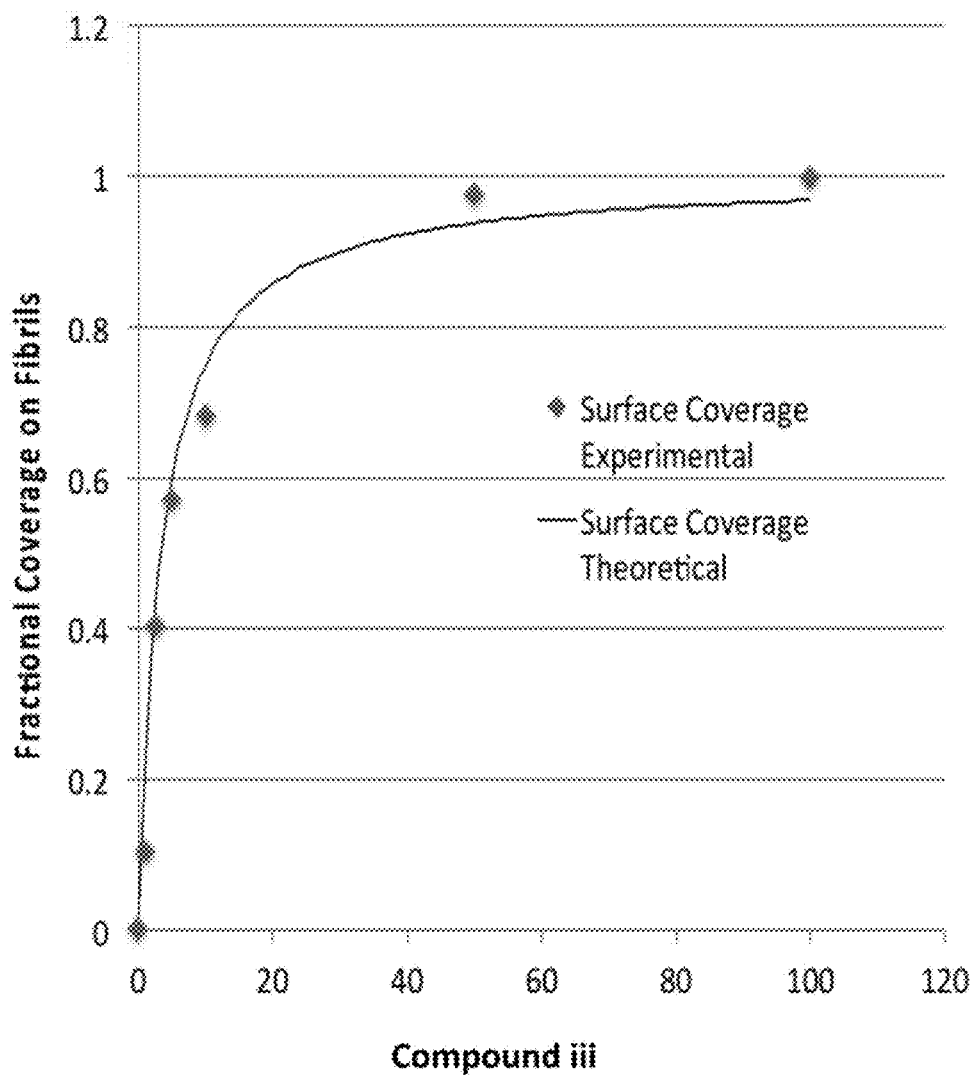
FIG. 7D is a graph showing fibril binding data and a calculated fit for estimation of the binding constant for liposomes bearing DSPE-PEG-Compound iii to fibrils at $K_d$=3.3 μM.

FIG. 7B is a graph showing fibril binding data and a calculated fit for estimation of the binding constant far Compound ii to fibrils at $K_d$=5.0 µM. FIG. 7C is a graph showing fibril binding data and a calculated fit for estimation of the binding constant for Compound iii to fibrils at $K_d$=5.0 µM. FIG. 7D is a graph showing fibril binding data and a calculated fit for estimation of the binding constant for liposomes bearing DSPE-PEG-Compound iii to fibrils at $K_d$=3.3 µM. Binding to fibrils was quantified by measuring the fluorescence of the respective binding agent to washed fibrils. The data was fitted to a monolayer binding equation; $K_d$=1/$K_b$.

Example 12

Hydrophilic Ligands Facilitate Stable Liposomes

To measure particle size, periodic samples from the extrusion process and a final sample after diafiltration were diluted in PBS and measured on a goniometer based dynamic light scattering system (BI-90, Brookhaven Instruments Corporation, Holtsville, N.Y.) attached to an autocorrelation system. A 532 nm solid, state laser was used as the light source, and the concentration of the sample adjusted until discriminated detection with a photomultiplier tube at 90° yielded ~100 kcounts per second (kcps). Correlation functions were measured using an exponentially spaced set of correlator bins, insuring at least 10 channels capturing the initial exponential drop of the correlation function, and 10 channels capturing the long term decay. Correlation functions were averaged for 2 minutes for each sample, using a dust-discrimination algorithm that eliminated correlation function slices that showed long term correlation functions significantly higher than baseline, indicating contamination with large particle sizes characteristic of dust. The resulting averaged correlation functions were analyzed using the CONTIN algorithm, and the volume averaged distributions used to estimate a mean size and standard deviation. All distributions were practically unimodal (>=99% of volume in the main peak).

Stability of the preparations was measured in PBS and reconstituted bovine plasma (RBP). An aliquot of the preparation was diluted 10× with either PBS or RBP and 200 µL of the diluted material placed in a dialysis bag, which was in turn placed in 200 mL PBS and slowly stirred for 24 hours. Samples of the external buffer were taken periodically during the 24 hour period and assayed for Gd content by ICP-AES. Leakage in bovine plasma was <5% in both buffer and bovine plasma.

FIG. 8 is a table showing the mean diameters and polydispersity indices of liposomes prepared with one of the MeXO4 targeting ligand, Compound iii, or PEGylated liposomes with no ligand. All liposomes included bis-stearyl-amide-DTPA-Gd in the bilayer, Gd-BOPTA (Gadobenate dimeglumine) in the liposome core interior, DPPC (55%), and cholesterol (40%). The liposomes were prepared by extrusion through track-etch membranes, including 5 extrusion passes through 400/200 nm membranes and 5 extrusion passes through 100 nm membranes targeted to give a mean diameter around 100-150 nm and a low polydispersity index, e.g., as demonstrated by the PEGylated liposomes with no ligand.

Figure 9B:
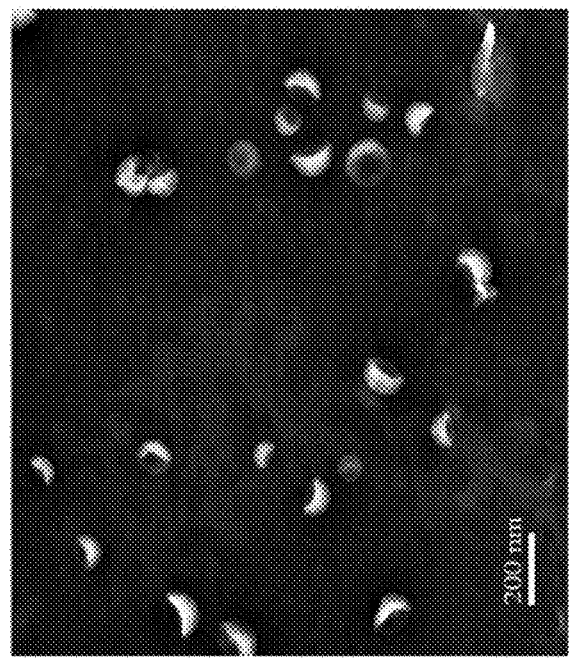
FIG. 9B shows negative stain TEM images of liposomes bearing untargeted liposomes (identical bilayer structure, with no MeXO4).
Figure 9A:
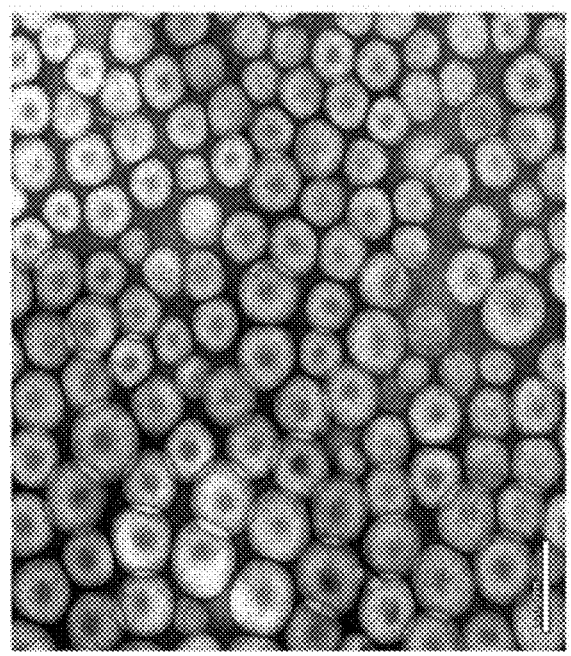
FIG. 9A shows negative stain TEM images of liposomes bearing DSPE-PEG-XO4 in the bilayer.

The MeXO4 liposomes however, exhibit a larger diameter and polydispersity, consistent with interference of the MeXO4 ligand with the bilayer as confirmed by negative stain electron microscopy (see also FIG. 9A). The replacement of the XO4 ligand with Compound iii resulted in liposomes of less than about 150 nm in diameter, with a low polydispersity. On incubation with reconstituted bovine plasma at 37° C. for 24 hours (plasma leak test), the Gd remained practically 100% associated with the particles, confirming that the modified ligand yielded a stable bilayer. Hydrophobic ligands like MeXO4 are believed to re-enter the bilayer and compromise its integrity, as reflected in the larger diameter of the resulting particles. A more hydrophilic ligand like Compound iii better maintains bilayer integrity and particle size post-extrusion.

Preparation of liposomes: 1,2-dihexadecanoyl-sn-glycero-3-phosphocholine (DPPC) and cholesterol were purchased from Lipoid Inc., Newark N.J., USA. DSPE-PEG3400-Compound iii was prepared as described above 1,2-distearoyl-sn-glycero-3-phosphoethanolamine-N-[methoxy(polyethylene glycol)-2000] (DSPE-MPEG2000) was purchased from Cordell Pharma, Liestahl, Switzerland. DPPC, cholesterol, DSPE-MPEG2000, bis-stearylamine-DTPA-Gd (BSA-DTPA-Gd), and DSPE-PEG3400-Compound iii at molar proportions DPPC:BSA-DTPA-Gd:cholesterol:DSPE-MPEG2000:DSPE-PEG3400-Compound iii:: 31:25:40:2:2) were dissolved in ethanol to achieve a total concentration of 150 mM. A 65 µM solution of ICG was made in 500 mM of gadobenate dimeglumine. The ethanolic solution of lipids was hydrated with a ten-fold excess of the IGG/gadobenate dimeglumine solution at 65° C. for 30 minutes, allowing multilamellar liposomes to form. The mixture was then extruded in a 10 mL Lipex extruder (Northern Lipids Inc., Burnaby, Canada) using a 200 nm poly-carbonate track-etch filter (10 passes) followed by a 100 nm polycarbonate filter (10 passes). The suspension was then diafiltered using a MICROKROS® (Spectrum Laboratories. Inc., Rancho Dominguez, Calif.) cross-flow diafiltration cartridge (500 kD cutof), exchanging the external buffer for phosphate buffered saline (PBS, pH 7.2) for 15 volume exchanges.

ICG content was measured by near-IR fluorescence (excitation 780 nm/emission 820 nm) in the diafiltrate at every volume exchange, and after the first volume exchange, practically no ICG was detected. The vast majority of the ICG lost from the retentate was present in the first volume exchange. Of the starting ICG, ~95% was estimated to remain associated with the liposomes.

Phosphorus and Gd content of the diafiltered product were measured using Inductively Coupled Plasma-Atomic Emission Spectrometry (ICP-AES). Of the starting Gd, practically 100% remained associated with the liposomes.

Interference of the MeXO4 ligand with the bilayer was confirmed by negative stain electron microscopy. FIG. 9A shows negative stain TEM images of liposomes bearing DSPE-PEG-XO4 in the bilayer. FIG. 98 shows negative stain TEM images of liposomes bearing untargeted liposomes (identical bilayer structure, with no MeXO4). The negative stain used was 1% uranyl acetate. Note the involuted and incomplete spheroids in the left hand image, consistent with the MeXO4 ligand interfering with and disrupting the bilayer. By contrast, the absence of MeXO4 and presence of Compound iii leads to consistent spheroidal structures typical of liposomes.

Replacement of the MeXO4 ligand with Compound iii resulted in liposomes that were once again close to 100 nm in diameter, with a low polydispersity. Moreover, after incubation with reconstituted bovine plasma at 37° C., for 24 hours, the Gd remained practically 100% associated with the particles, confirming that the modified ligand yielded a stable bilayer.

Example 13

Example Liposomes Demonstrate High Gd Molar Relaxivity at Low Field Strengths

Figure 10A:
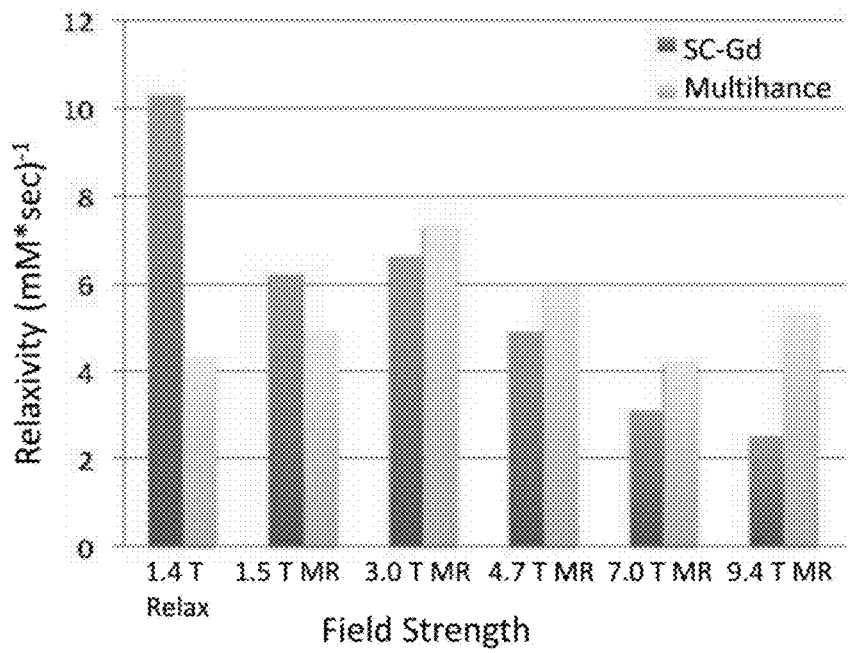
FIG. 10A is a bar graph showing the example liposomes high Gd molar relaxivity at low field strength compared to a free Gd chelate.
Figure 10B:
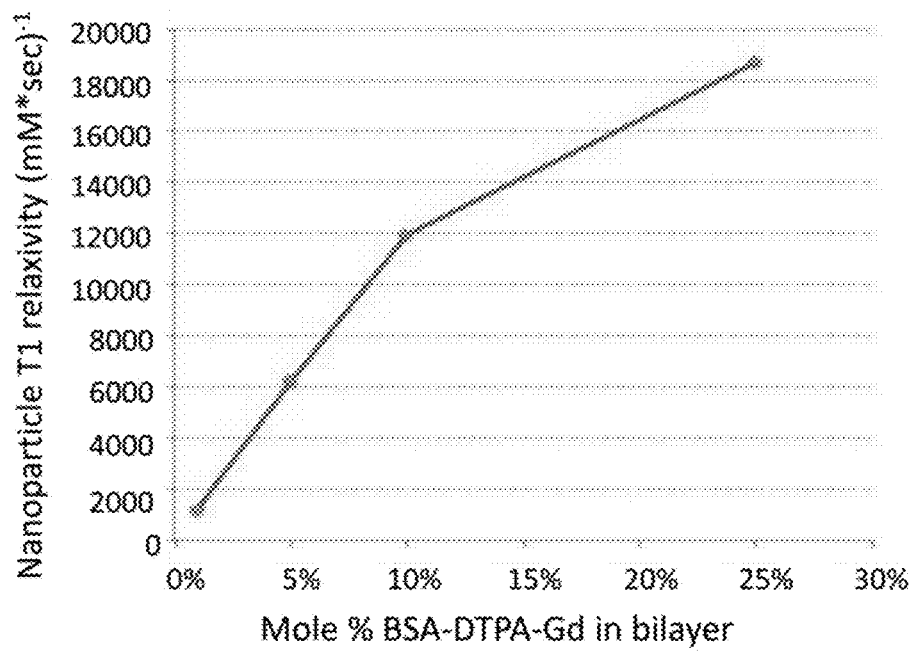
FIG. 10B is a graph showing the resulting particles have extremely high relaxivity on a per-particle basis.

Liposomes were prepared decorated with surface Gd chelates on the surface of the lipid bilayer (Gd chelates conjugated to a lipid anchor BSA-DTPA-Gd such that bis-stearyl chains insert into the bilayer of the liposomes). These liposomes demonstrated high Gd molar relaxivity at low field strengths as shown in FIG. 10A. In FIG. 10A, the example liposomes are compared to a free Gd chelate (GadobenateDimelglumine, MULTIHANCE™, Bracco Imaging, Monroe Township, N.J.) at lower field strengths, but the difference erodes at higher field strengths to the point where at 9.4 T, the free chelate is more relaxive than the surface presentation At higher field strengths however, this enhancement of relaxivity is reduced, and at the highest field strength tested (9.4 T) the surface Gd is less relaxive than the free chelate. Taking advantage of the relaxivity enhancement at low field strengths, we tested formulations with up to 25% of the liposome bilayer consisting of BSA-DTPA-Gd. The liposomes were stable, exhibiting no measurable loss of Gd upon storage under refrigerated conditions for up to 8 weeks. The resulting particles have extremely high relaxivity on a per-particle basis, as shown in FIG. 10B. On a particle basis, a relaxivity of ~190,000 $mM^{-1}s^{-1}$ was achieved at 1T.

1.5, 3, 4.7, 7 and 9.4T measurements were made on individual MRI instruments. 1.4 T measurement as made on a Bruker Minispec MQ60 relaxometer (Bruker, Billerica Mass.). 1T measurements were made on an Aspect M2 permanent magnet MRI instrument (Aspect Imaging, Shoham Israel). T1 measurements on the relaxometer were performed at 37° C. whereas measurements on MRI instruments were performed at standard temperature (1.8-20° C.).

All animal experiments conducted at the Baylor College of Medicine ere approved by the Baylor institutional Animal Care and Use Committee. All animal experiments at MD Anderson Cancer Center were approved by the MDA Institutional Animal Care and Use Committee. All studies were in conformance with the NC3RS-ARRIVE criteria. Tg2576 mice were purchased from Taconic Biosciences, Inc., Hudson, N.Y. TetO/APP mice were a kind gift of Dr. Joanna Jankowsky at Baylor College of Medicine. All APP− control animals were age-matched non-transgenic littermates of APP+ animals in this study. All TG2576 mice were imaged on a 1.0 T Bruker icon system (Bruker Instruments, Billerica, Mass.) at MD Anderson Cancer Center. All TetO/APP mice were imaged on an 1.0 T Aspect M2 system (Aspect Imaging, Shoham, Israel). Note that these two scanner instruments are built on identical hardware, both manufactured by Aspect Imaging. Only the software interface is different. All imaging parameters were identical on the two instruments.

Anesthesia was induced in an isoflurane inhalation box using 5% isoflurane in air. Mice were then placed on a custom fabricated sled with integral face-cone for continued anesthesia delivery by inhalation (1.5-3% isoflurane in air) and transferred to the magnet cavity. A pre-contrast image of the brain was acquired using a 2D multi-slice spin echo sequence with the following parameters: TE=32 ms, TR=770 ms, slice thickness=1.2 mm, FOV=30×30 mm, matrix=156×156, 24 slices A-P, and NEX=2. Mice were then allowed to awaken and returned to their cages. 24 hours following the pre-contrast image, APP+ and APP− mice in the test group were injected with Compound iii targeted liposomes (150 mM total lipid concentration, 37.5 mM total Gd concentration, injection volume 4 μL/g body weight, 0.15 mmol Gd/kg), while APP+ mice in the control group were injected with untargeted (i.e. no Compound iii present) liposomes with identical parameters. 4 days after injection, the mice were anesthetized and imaged again using an identical sequence. The half-life of the PEGylated liposomes prepared in this study was about 18 to 24 hours, and the 4-day interval was chosen to facilitate clearance of the unbound agent from the bloodstream, in order to reduce background signal.

Samples with Gd concentrations from 0.25 to 1.0 mM were prepared by diluting liposomal preparations in PBS. T1 relaxation measurements were then performed on a 60 Hz Bruker minispec MQ benchtop relaxometer (Bruker Instruments, Billerica, Mass.). Longitudinal relaxation times (T1) were obtained using an inversion recovery sequence. A plot of relaxation rate (1/T1) against Gd concentration yielded a straight line with slope defined as the T1 relaxivity (r1). For relaxivity measurements at higher field strengths (1.5 T to 9.4 T), the same samples were imaged on corresponding MRI instruments using T1-weighted fast spoiled gradient echo (FSPGR) sequence. The slope of 1/T1 versus concentration plot was used to estimate the relaxivity at each field strength.

Example 14

Example Liposomes Image Amyloid Plaques By MRI in Mice

Dual-Gd liposomes, targeted to amyloid plaques using the Compound iii ligand were therefore tested for their ability to image amyloid plaques in mice. The dual-Gd/Compound iii liposomes were injected intravenously into mice, and scanned 4-days later using a T1-weighted spin echo sequence (TE=32 ms, TR=770 ms) on a 1 T MRI scanner. The dual-Gd/Compound iii liposomes resulted in signal enhancement, in patterns characteristic of amyloid deposition, in two distinct strains of amyloid bearing mice (1.5 month old TetO/APPswe-ind and 9 month old Tg2576). Pre-injection scans of the same mice and amyloid-negative mice similarly injected, as well as amyloid positive mice injected with an untargeted version of the same particles (i.e. no Compound iii) yielded no signal in comparison. The 4-day delay was designed to allow unbound liposomes to clear from the circulation. PEGylated liposomes have a circulation half life of about 24 hours, and past experience suggested the 4-day delay was sufficient for near complete elimination of liposomes from the blood pool.

Histology: Immediately after the 4-day post images were acquired, the mice were sacrificially perfused with saline followed by 10% formalin, the brain was excised and submerged in 10% formalin for 24 hours, then transferred to 30% sucrose and refrigerated until the brain sank (usually about 72 hours). Whole brain NIR imaging was performed at this stage. The brain was then embedded in OCT solution and stored at −80° C. prior to serial sectioning. Sections were cut at 30 μm thickness, washed in tris-buffered saline with 0.2% tween. For amyloid antibody staining, sections were incubated in 5% normal donkey serum for 1 hour, followed by incubation with anti-amyloid β antibody (4G8, from Sigma-Aldrich, St. Louis, Mo.) in 3% NDS at 4° C. overnight. Sections were then washed, and incubated with a FITC or Cy5-tagged dylight649 anti-mouse IgG secondary antibody, mounted and coverslipped using Vectashield mounting medium (Vector Laboratories, Burlingame Calif.) and imaged using the appropriate filter set.

Exemplary images from this study are shown in FIGS. 11A-F. T1 weighted MR imaging of amyloid plaques in mouse models, pre- and 4 days post i.v. injection of nanoparticle MR agent. A 2D Spin-echo sequence, (TE=32 ms, TR=770 ms, slice thickness=1.2 mm, FOV=30×30 mm, matrix=156×156, and NEX=2) was used. Coronal 2D slices of the brain through the cortex and hippocampus are shown. FIG. 11A depicts results for a TetO/APPswe-ind mouse, 15 months old, wherein APP production was suppressed until 6 weeks of age by doxycycline in diet. FIG. 11B depicts results fix a pre-injection scan of the mouse of FIG. 11A. FIGS. 11C, D depict results for a Tg2576 mouse (APPswe) 9 months old and a pre-injection scan of the same mouse, respectively. FIG. 11E depicts results for a Tg2576 mouse injected with untargeted (non-amyloid-binding) particles. FIG. 11F depicts results for a non-transgenic sibling of the mouse of FIG. 11E, injected with amyloid-targeted particles. Total signal was mapped to a "rainbow" color map using Osirix software (available online at http://www.osirix-viewer.com/). The range from the predominant blue background to green foreground represents a >2× signal increase. The range from green to yellow indicates a further 2× increase, 9 month old Tg2576 mice showed a very different pattern of labeling (pial, hippocampal and some signal in the ventricles) compared to older TetO/APP mice, (extensive cortical and hippocampal signal with no ventricular signal) suggesting slow clearance from the CSF in the Tg2576 example. 6/6 animals in each group were consistent with these images, with the exception of the Tg2576 APP+ animals, of which 2/6 showed this enhancement pattern. The remaining 4/6 showed no enhancement, and were indistinguishable from the non-transgenic sibling animals. Immunohistochemistry using the 4G8 antibody to Aβ, however, revealed that the 4 animals that showed no enhancement also did not have significant amyloid pathology in the brain.

There was therefore complete correspondence between the presence of amyloid deposits and positive MRI signal, as summarized in table form in FIG. 12. FIG. 12 shows amyloid pathology score by immunohistochemistry using the 4G8 antibody, imaging agent used. (Compound iii targeted or control untargeted) and individual measures of nanoparticle presence in mouse brain. Semi-quantitative scoring of Aβ plaques as by a four-tie scale of 0 (none), 1 (sparse), 2 (moderate) and 3 (severe/frequent). Presence of positive signal for ICG, ligand, and MRI was denoted by an "X" and absence by a "–". There was a near 100% correlation between the immunohistochemistry results and each of the measures of nanoparticle presence. APP+ mice of either strain (TetO/APPswe, or Tg2576) treated with the targeted agent showed positive signal in MRI, immunohistochemistry and fluorescent markers of nanoparticle presence, while APP+ mice of either strain treated with untargeted agent showed no signal, and APP– mice showed no signal regardless of treatment. The data is consistent with the targeted agent being able to access and bind amyloid plaques, while being cleared in the absence of binding, and with no binding occurring in the absence of the targeting ligand.

FIGS. 13A-13Z represent 13 pairs of MRI images representative of the data summarized in FIG. 12. For each pair of images, the right hand image is pre-contrast, and the left hand image is 3-4 days post contrast. All image pairs were arranged at the same window level and width to provide similar or identical color maps. Each image pair is identified by a mouse (strain (TetO/APP or Tg2576), genotype (APP+ or APP–), and the treatment (Compound iii-targeted particles, or untargeted particles).

Example 15

Example Liposomes Image Amyloid Plaques By IR Fluorescence in Mice

The liposomes also contained ~0.6 mole % Indocyanine Green (ICG) in the bilayer, for near-infrared imaging. FIGS. 14A-H4 show results from near infrared imaging of mouse brains post mortem. Confocal imaging of brain sections from Tg2576 mice revealed enhanced ICG signal in the cortex and hippocampus of the transgenic mice, showing greater localization in the APP+ brain (FIG. 14A) when compared to the non-transgenic controls (FIG. 14B). At high magnification, FIG. 14E revealed the characteristic punctuate structure of amyloid deposits corresponding to FIG. 14A; FIG. 14F corresponds to the controls of FIG. 14B.

The whole brains of TetO/APP+ mice showed greater near infrared fluorescence (FIG. 14C) than their APP– sibling controls (FIG. 14D). Uniformly increased ICG signal localized in the APP-positive brain (FIG. 14C), compared to overall lower signal in the APP-negative brain (FIG. 14D) with occasional hotspots corresponding to vascular leak locations.

Using a fluorescently labeled 4G8 antibody to amyloid plaque, colocalization of the antibody (green, FIG. 14G1), ICG (red) and Compound iii (blue) was demonstrated for a cluster of 3 plaques (FIGS. 13G1-G4) and for an individual plaque (FIGS. 13H1-H4). As in the case of the MRI signal, the fluorescence signal was also consistent with the immunohistochemical measure of amyloid pathology presence, as summarized in FIG. 12. These results confirm that Compound iii targeted Dual-Gd liposomes can penetrate the BBB, seek out the amyloid plaques and generate sufficient signal enhance for detection using MRI at clinical field strength.

Discussion

Synthetic efforts focused on the three compounds in FIGS. 1A-1B with the lowest C Log P values (Compound ii, Compound i and Compound iii). Synthesis and purification were efficient, with overall yields around 90%. Compound ii and Compound iii were tested for amyloid fibril binding and specificity, and yielded very similar results, suggesting that amyloid binding ability is not significantly affected by the relatively high hydrophilicity of these molecules. In fact, compared to similar studies performed with MeXO4 the present molecules appear to bind amyloid fibrils much stronger than MeXO4, with only about 60% of the bound species displaced by Chrysamine G, compared to >80% for MeXO4. Compound iii was chosen as the lead candidate based on its lower C Log P value and marginally higher amyloid binding ability.

The hydrophilicity of Compound iii led to the formation of stable liposomes, without bilayer compromise, as indicated in FIG. 8. Liposomes with saturated lipid and cholesterol in the bilayer, when extruded through 100 nm membranes, result in liposomes with diameter around 100 nm. Particle sizes considerably larger than 100 nm are associated with bilayer destabilization, vesicle fusion, and the formation of multi-lamellar structures, as demonstrated with MeXO4 liposomes in FIG. 8 and FIG. 9. The relatively hydrophobic MeXO4 ligand, when tethered onto a liposome surface by a flexible PEG tether, may is believed to partition into the bilayer, accounting for the compromise in bilayer stability s demonstrated with MeXO4 liposomes in FIG. 8 and FIG. 9A. Upon replacement of the MeXO4 ligand with the more hydrophilic Compound iii ligand, any propensity for the ligand to partition into the bilayer was eliminated or reduced, accounting for the retained bilayer integrity demonstrated by the data in in FIG. 8 observed for Compound targeted liposomes.

The ability of Compound iii to bind amyloid pathology was tested using human brain tissue obtained from autopsy of an 88 year old human AD patient, Compound iii clearly stains the human tissue in a focal pattern consistent with the staining of amyloid plaques (FIG. 5C). Aged canines are a natural model of beta-amyloid deposition and incubation of a section of frontal cortex from a 12.3 year old beagle in Compound iii also showed CAA labeling (FIG. 5D).

To build a nanoparticle with sufficient T1 signal to allow visualization of amyloid plaques, we adopted the Dual-Gel presentation previously demonstrated to induce enhanced Gd relaxivity. The conjugation of Gd chelates to a bis-stearyl a aide anchor inserted into the bilayer may retard rotational correlation of the Gd atom, thereby increasing the rotational correlation time $\tau_R$. Increased rotational correlation times of Gd chelates may lead to a peak in T1 relaxivity at low field strengths, around 1 T, while this enhancement may be greatly reduced, and eventually may be reversed at higher field strengths >7 T. This is consistent with the behavior observed (FIG. 10A). The T1 relaxivity of liposomal surface Gd (on a Gd molar basis) was 2.5× higher than that of a free molecular chelate at 1.4 T and 1.5 T, but at higher fields, the free molecular chelate exhibited a higher relaxivity. Accordingly, relaxivity and in vivo imaging were tested at low (1 T) field strength.

When a targeted liposome (such as the Compound iii targeted liposome considered here) may bind to a molecular target (such as the beta sheet structure of an amyloid plaque), each molecular target may be associated with an entire liposome, and the corresponding signal in the MR image array be attributable to the entire liposome. The relaxivity on a liposome molar basis may therefore be linearly related to the signal associated with the molecular target. The relaxivity of surface Gd liposomes was therefore measured on a liposome molar basis, as a function of increasing Gd chelate concentration in the liposome bilayer. The results in FIG. 10B show an expected linear dependence of relaxivity on the number of Gd chelates in the bilayer. At 25% of the bilayer molecules bearing a Gd chelate the T1 relaxivity on a per-particle basis was estimated to be around 190,000 mM-1 s-1. For ~120 nm diameter particles, this may correspond to roughly 48,000 Gd chelates per particle, of which half may be on the outer leaflet of the liposome bilayer, and half may be on the inner leaflet. Assuming that the inner leaflet Gd is not substantially active for T1 relaxation while the outer leaflet chelates are, this suggests a molar relaxivity on a per-Gd basis of roughly 8 mM-1 s-1, of the same order as that measured using the 1.4 T relaxometer (FIG. 10A).

Upon injection administration into the bloodstream, the Compound targeted liposomes appeared to avidly cross the blood brain barrier and bind to amyloid plaques (FIGS. 11A-F). Such permeability of the blood brain barrier was consistent with past observations of the ability of MeXO4 targeted liposomes to cross the BBB and label amyloid plaques in the APP/PSEN1 mouse model of AD. Also, past observations demonstrated the ability of untargeted liposomes to cross the BBB in the TetO/APP model of AD, and demonstrated significant leakage across the BBB in age-dependent and amyloid-dependent manners. While all mice tested showed leaks in the choroid plexus, older mice (>14 months of age) showed significantly higher leak along major blood vessels, while APP+ mice showed greater leak in the cerebral cortex. The TetO/APP mice in the present study were all >14 months old and showed more widespread signal in the brain, while the Tg2576 mice were all 9-10 months old and showed less signal, concentrated around pial and cortical vessels. Further, while 6/6 TetO/APP mice showed clear signal in the brain, consistent with localization of the targeted agent, only 2/6 Tg2576 animals showed clear brain signal. Immunohistochemically, however, the same 2/6 Tg2576 animals exhibited amyloid pathology, while the remaining 4/6 did not.

Confirmation of the localization of the particles to amyloid plaques comes from the data in FIGS. 14A-H4. Whole brain near-IR images visualizing the indocyanine label (FIGS. 14C-D) were consistent with increased localization in APP+ brains compared to APP− brains. Slices through the cortex and hippocampus of APP+ and APP− mice (FIGS. 14A-B) showed significant localization in the APP+ brain, with the maximum intensity observed in the cerebral cortex and portions of the hippocampus. Significant staining was also observed in the thalamus, and was consistent with thalamic signal in the MR image (FIG. 14C) of the same mouse. Under high magnification (FIGS. 14E4) of the cerebral cortex, the ICG signal in the APP+ mouse brain was seen to be both punctuate, consistent with labeling of focal plaques, and along blood vessel walls, consistent with labeling of CAA.

Detailed histological examination of individual focal plaques (FIGS. 14G1-H4) the cerebral cortex reveal that the ligand targeted particles appeared to label both the dense and diffuse sections of the plaque. FIGS. 14G1-H4, the 4G8 antibody, visualized with FITC is labeled green, the ICG is labeled red, while the Compound iii ligand is labeled blue. FIGS. 14G1-G4 show a field with 3 focal plaques visible. Also in the field is a more diffuse surrounding amyloid deposition pattern. The 4G8 antibody labels both these entities. The focal plaques appeared to have a relatively uniform amyloid density at the center, and higher density in the periphery, consistent with numerous other observations of plaques in mice using antibody and thioflavin-S staining. The ICG and Compound iii labels (red and blue respectively) are well correlated with each other and with the antibody label, demonstrating a low density of binding in the center of the plaques and high density nodules in the periphery, leaving little doubt that the liposomal particles bind intact to the plaques, and label both the high density focal plaques as well as lower density diffuse plaques.

Some differences were noted in the MRI signal patterns between the TetO/APP and TG2576 mice, with the former showing signal in the cerebral cortex, hippocampus, and striatum, consistent with preferential amyloid deposition in these areas due to heterogeneous activity of the CaMkIIα promoter. A more complete deposition pattern was observed in the Tg2576 mice, consistent with more uniform plaque deposition. The Tg2576 mice also showed strong ventricular signal that may be due to the continued presence of the agent in the cerebrospinal fluid, the likely transport medium for the extravasated liposomes.

Liposomes penetrate the BBB in mouse models of amyloid deposition and Alzheimer's disease as collectively demonstrated previously and herein across 3 different mouse models, APP/PSEN1, TetO/APPP, and Tg2576. This BBB penetration does not require any active transport mechanism because previous work demonstrated that simple PEGylated liposomes are readily transported through the BBB. Retention of liposomes at the sites of amyloid deposition, for extended periods of time, however, depends on binding to a molecular target. The use of MeXO4 as the binding ligand in our previous work demonstrated binding to amyloid plaques and visualization ex vivo by microscopy. As demonstrated using Compound iii herein, the use of a novel targeting ligands leads to liposomes with improved, bilayer integrity, and the consequent encapsulation of large amounts of Gd chelates. These Gd chelates, presented on the surface of the liposome, were hyper-relaxive at low (~1 T) field strengths, and provided per-particle relaxivity of ~190,000 $mM^{-1} s^{-1}$, sufficient to enable their visualization in vivo using T1-weighted MRI. Thus, amyloid plaques in two different mouse models (Tg2576 and TetO/APP) were visualized.

The present methods, ligands, conjugates and liposomes are believed to readily facilitate crossing the BBB in humans. It is known from MRI studies performed in AD and MCI patients that the BBB indeed compromised and the extent of compromise is independent of amyloid burden. Also, a recent study using DCE-MRI confirmed that the BBB in the aging human hippocampus breaks down and becomes permeable. Confirmation that the agent binds amyloid pathology other than in a mouse overexpression model is demonstrated herein by testing binding to amyloid deposits in dog brain and human brain slices in vitro. Accordingly, the present methods, ligands, conjugates and liposomes may function in humans.

The present application demonstrates MRI imaging of amyloid plaques in rodent models at clinically acceptable field strengths, which is believed to extend to analysis of plaques and diagnosis of AD in humans. The described MRI imaging may offer a number of substantial benefits over current non-invasive imaging technologies, such as PET imaging, including increased availability, reduced cost, and enhanced resolution. The availability of know approved PET agents for the imaging of amyloid plaques may be limited and restricted to large academic medical centers. By contrast, the work described herein may offer worldwide availability. Moreover, T1 agents may be extremely attractive because of their positive signal, leading to increased confidence in signal interpretation. The work described herein is targeted fix use in low field (1-3 T) scanners consistent with state-of-the-art MRI scanners for human imaging.

In addition to analyzing amyloid plaque, the work herein may be used in conjunction with a secondary marker, such as identification of neurofibrillary Tau tangles, to diagnose AD.

To the extent that the terra "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When "only A or B but not both" is intended, then the term "only A or B but not both" will be employed. Thus, use of the term "or" herein is the inclusive and not the exclusive use. As used in the specification and the claims, the singular forms "a," "an," and "the" include the plural. Finally, where the term "about" used in conjunction with a number, it is intended to include ±10% of the number. For example, "about 10" may mean from 9 to 11.

In general, "substituted" refers to an organic group as defined, below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified, in some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy heterocyelyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN), and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tort-butyl, neopentyl, isopentyl, and 2,2-dimethylpropyl groups. Representative substituted alkyl groups may be substituted one or more tunes with substituents such as those listed above and include, without limitation, haloalkyl trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Exemplary monocyclic cycloalkyl groups include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments, the number of ring carbon atoms ranges from 3 to 5, 3 to 6, or 3 to 7. Bi- and tricyclic ring systems include both bridged cycloalkyl groups and fused rings such as, but not limited to, bicyclo[2.11]hexane, adamantyl, decalinyl, and the like. Substituted cycloalkyl groups may be substituted one or more times with non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclic groups include aromatic (also referred to as heteroaryl) and non-aromatic ring compounds containing 3 or more ring members of which one or more is a heteroatom such as, but not limited to, N, O, and S. In some embodiments, the heterocyclyl group contains 1, 2, 3 or 4 heteroatoms. In some embodiments, heterocyclic groups include mono-, bi- and tricyclic rings having 3 to 16 ring members, whereas other such groups have 3 to 6, 3 to 10, 3 to 12, or 3 to 14 ring members. Heterocyclic groups encompass aromatic, partially unsaturated and saturated ring systems, such as, for example, imidazolyl, imidazolinyl and imidazolidinyl groups. The phrase "heterocyclic group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocyclic groups that have other groups, such as alkyl, oxo or halo groups, bonded to one of the ring members. Rather, these are referred to as "substituted heterocyclic groups". Heterocyclic groups include, but are not limited to, aziridinyl, azetidinyl, pyrrolidinyl, pyrazolidinyl, thiazolidinyl, tetrahydrothiophenyl, tetrahydrofuranyl, dioxolyl, furanyl, thiophenyl, pyrrolyl, pyrrolinyl, imdazolyl, trridazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazoyl, tetrahydrobenzmidazoyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclic groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazoyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Although the phrase "heteroaryl groups" includes fused ring compounds, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

Heteroaralkyl groups are alkyl groups as defined above in which a hydrogen or carbon bond of an alkyl group is replaced with a bond to a heteroaryl group as defined above. Substituted heteroaralkyl groups may be substituted at the alkyl, the heteroaryl or both the alkyl and heteroaryl portions of the group. Representative substituted heteroaralkyl groups may be substituted one or more tunes with substituents such as those listed above.

Groups described herein having two or more points of attachment (i.e., divalent, trivalent, or polyvalent) within the compound of the technology are designated by use of the suffix, "ene." For example, divalent alkyl groups are alkylene groups, divalent aryl groups are arylene groups, divalent heteroaryl groups are heteroarylene groups, and so forth. Substituted groups having a single point of attachment to the compound of the technology are not referred to using the "ene" designation. Thus, for example, chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Examples of linear alkoxy groups include, but are not limited to, methoxy, ethoxy, propoxy, butoxy, pentoxy, hexoxy, and the like. Examples of branched alkoxy groups include, but are not limited to, isopropoxy, sec-butoxy, tort-butoxy, isopentoxy, isohexoxy, and the like. Examples of cycloalkoxy groups include, but are not limited to, cyclopropyloxy, cyclobutyloxy, cyclopentyloxy, cyclohexyloxy, and the like. Representative substituted alkoxy groups may be substituted one or more times with substituents such as those listed above.

The to term "amine" (or "amino"), as used herein, refers to NR$^a$R$^b$ groups, wherein R$^a$ and R$^b$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is NH$_2$, methylamino, dimethylamino, ethylamino, diethylamino, propylamino, isopropylamino, phenylamino, or benzylamino. The term "alkylamino" is defined as NR$^c$R$^d$, wherein at least one of and R$^d$ is alkyl and the other is alkyl or hydrogen. The term "arylamino" is defined as NR$^e$R$^f$, wherein at least one of R$^e$ and R$^f$ is aryl and the other is aryl or hydrogen.

The term "halogen" or "halo," as used herein, refers to bromine, chlorine, fluorine, or iodine. In some embodiments, the halogen is fluorine. In other embodiments, the halogen is chlorine or bromine.

As stated above, while the present application has been illustrated by the description of embodiments, and while the embodiments have been described in considerable detail, it is not the intention to restrict or in any way limit the scope of the appended claims to such detail. Additional advantages and modifications will readily appear to those skilled in the art, having the benefit of this application. Therefore, the application, in its broader aspects, is not limited to the specific details and illustrative examples shown. Departures may be made from such details and examples without departing from the spirit or scope of the general inventive concept.

The invention claimed is:

1. A liposomal composition, comprising:
a membrane, comprising:
a phospholipid-polymer-aromatic conjugate, the aromatic moiety in the phospholipid-polymer-aromatic conjugate comprising:

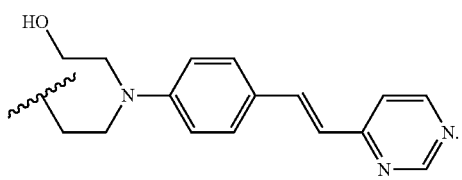 [SMILES: *CCN(CCO)c1ccc(/C=C/c2ccncn2)cc1]

2. The liposomal composition of claim 1, further comprising a nonradioactive magnetic resonance imaging (MRI) contrast enhancing agent that is at least one of encapsulated by or bound to the membrane.

3. The liposomal composition of claim 1, the membrane further comprising a first phospholipid and a second phospholipid, the second phospholipid being derivatized with a hydrophilic polymer.

4. The liposomal composition of claim 1, the membrane further comprising:
a phospholipid;
cholesterol;
a nonradioactive MM contrast enhancing agent comprising gadolinium; and
1,2-distearoyl-sn-glycero-3-phosphoethanolamine-N-[methoxy(polyethylene glycol)-2000].

5. The liposomal composition of claim 1, the phospholipid-polymer moiety in the phospholipid-polymer-aromatic conjugate being represented by the following structural formula:

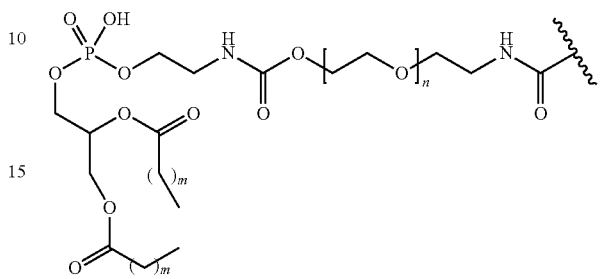

or a salt thereof, wherein m is one of 12, 13, 14, 15, 16, 17, or 18, and wherein n is an integer between 60 and 100.

6. The liposomal composition of claim 5, wherein m is 16.

7. The liposomal composition of claim 5, wherein n is an integer between 70 and 90.

8. The liposomal composition of claim 5, wherein n is 79.

9. A kit for imaging amyloid deposits in a patient, the kit comprising: a liposomal composition, the liposomal composition comprising:
a membrane, comprising:
a phospholipid-polymer-aromatic conjugate, the aromatic moiety in the phospholipid-polymer-aromatic conjugate comprising:

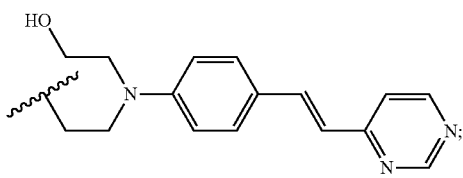

a nonradioactive magnetic resonance imaging (MM) contrast enhancing agent at least one of encapsulated by or bound to the membrane; and
instructions, the instructions directing a user to:
introduce into the patient a detectable quantity of the liposomal composition;
allow sufficient time for the liposomal composition to be associated with one or more amyloid deposits; and
detect the liposomal composition associated with the one or more amyloid deposits.

10. The kit of claim 9, the phospholipid-polymer moiety in the phospholipid-polymer-aromatic conjugate being represented by the following structural formula:

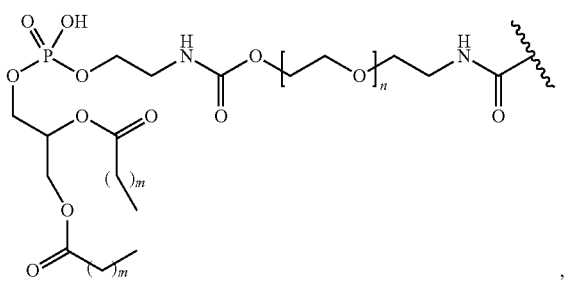

or a salt thereof, wherein m is one of 12, 13, 14, 15, 16, 17, or 18, and wherein n is an integer between 60 and 100.

11. The kit of claim 10, wherein m is 16.

12. The kit of claim 10, wherein n is an integer between 70 and 90.

13. The kit of claim 10, the membrane further comprising:
a phospholipid;
cholesterol; and
1,2-distearoyl-sn-glycero-3-phosphoethanolamine-N-[methoxy(polyethylene glycol)-2000].

14. A method for imaging amyloid deposits in a patient, the method comprising:
introducing into the patient a detectable quantity of a liposomal composition, the liposomal composition comprising:
a membrane, comprising:
a phospholipid-polymer-aromatic conjugate, the aromatic moiety in the phospholipid-polymer-aromatic conjugate comprising:

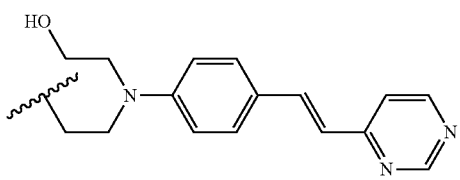 [SMILES: *CCN(CCO)c1ccc(/C=C/c2ccncn2)cc1]

a nonradioactive magnetic resonance imaging (MM) contrast enhancing agent at least one of encapsulated by or bound to the membrane;
allowing sufficient time for the liposomal composition to be associated with one or more amyloid deposits; and
detecting the liposomal composition associated with the one or more amyloid deposits.

15. The method of claim 14, the detecting comprising detecting using magnetic resonance imaging.

16. The method of claim 14, the MRI contrast enhancing agent comprising gadolinium.

17. The method of claim 16, the liposomal composition characterized by per-particle relaxivity in mM-1 s-1 at 1 T of at least about: 190,000.

18. The method of claim 14, the membrane further comprising:
a phospholipid;
cholesterol;
a nonradioactive MRI contrast enhancing agent comprising gadolinium; and
1,2-distearoyl-sn-glycero-3-phosphoethanolamine-N-[methoxy(polyethylene glycol)-2000].

19. The method of claim 14, further comprising diagnosing the patient with Alzheimer's disease according to detecting the liposomal composition associated with the one or more amyloid deposits.

20. The method of claim 14, further comprising:
identifying the patient as potentially having Alzheimer's disease according to detecting the liposomal composition associated with the one or more amyloid deposits;
subjecting the patient to an analysis for tau neurofibrillary tangles; and
upon determining the presence of tau neurofibrillary tangles in conjunction with detecting the liposomal composition associated with the one or more amyloid deposits, diagnosing the patent with Alzheimer's disease.

* * * * *